US010639611B2

(12) United States Patent
Behabtu et al.

(10) Patent No.: US 10,639,611 B2
(45) Date of Patent: *May 5, 2020

(54) POLYSACCHARIDE COMPOSITIONS FOR ABSORBING AQUEOUS LIQUID

(71) Applicant: DUPONT INDUSTRIAL BIOSCIENCES USA, LLC, Wilmington, DE (US)

(72) Inventors: Natnael Behabtu, Wilmington, DE (US); Rakesh Nambiar, West Chester, PA (US)

(73) Assignee: DUPONT INDUSTRIAL BIOSCIENCES USA, LLC, Wilmington, DE (US)

(*) Notice: Subject to any disclaimer, the term of this patent is extended or adjusted under 35 U.S.C. 154(b) by 0 days.

This patent is subject to a terminal disclaimer.

(21) Appl. No.: 15/952,401

(22) Filed: Apr. 13, 2018

(65) Prior Publication Data

US 2018/0229214 A1    Aug. 16, 2018

Related U.S. Application Data

(63) Continuation of application No. 14/965,961, filed on Dec. 11, 2015, now Pat. No. 9,968,910.

(60) Provisional application No. 62/095,423, filed on Dec. 22, 2014.

(51) Int. Cl.

| B01J 20/24 | (2006.01) |
|---|---|
| C08B 37/00 | (2006.01) |
| C12P 19/04 | (2006.01) |
| C08L 5/00 | (2006.01) |
| C12P 19/18 | (2006.01) |
| A61K 47/36 | (2006.01) |

(52) U.S. Cl.
CPC ............ *B01J 20/24* (2013.01); *A61K 47/36* (2013.01); *C08B 37/0009* (2013.01); *C08L 5/00* (2013.01); *C12P 19/04* (2013.01); *C12P 19/18* (2013.01)

(58) Field of Classification Search
None
See application file for complete search history.

(56) References Cited

U.S. PATENT DOCUMENTS

| 5,019,292 A | 5/1991 | Baeck et al. |
|---|---|---|
| 5,145,906 A | 9/1992 | Chambers et al. |
| 5,338,766 A | 8/1994 | Phan et al. |
| 5,702,942 A | 12/1997 | Leathers et al. |
| 5,786,196 A | 7/1998 | Cote et al. |
| 5,789,209 A | 8/1998 | Leathers et al. |
| 5,952,205 A | 9/1999 | Catani et al. |
| 6,124,391 A | 9/2000 | Sun et al. |
| 6,242,225 B1 | 6/2001 | Catani et al. |
| 6,525,106 B1 | 2/2003 | Des Marais et al. |
| 6,579,840 B1 | 6/2003 | Heltovics |
| 6,660,502 B2 | 12/2003 | Catani et al. |
| 7,000,000 B1 | 2/2006 | O'Brien |
| 7,009,020 B2 | 3/2006 | Doane et al. |
| 7,012,053 B1 | 3/2006 | Barnabas et al. |
| 7,056,880 B2 | 6/2006 | Wang et al. |
| 7,365,190 B2 | 4/2008 | Couture et al. |
| 7,534,759 B2 | 5/2009 | Wahl et al. |
| 7,576,048 B2 | 8/2009 | Gray et al. |
| 8,541,041 B2 | 9/2013 | Pilling |
| 9,169,506 B2* | 10/2015 | Caimi ............... C08B 37/0009 |
| 9,926,541 B2* | 3/2018 | Paullin .................. C12P 19/18 |
| 9,968,910 B2* | 5/2018 | Behabtu ................. B01J 20/24 |
| 2005/0059633 A1* | 3/2005 | Van Geel-Schuten ...................... C12N 9/1051 514/54 |
| 2006/0127328 A1 | 6/2006 | Monsan et al. |
| 2006/0134417 A1 | 6/2006 | Takaha et al. |
| 2013/0244288 A1 | 9/2013 | O'Brien et al. |
| 2014/0087431 A1 | 3/2014 | Payne et al. |
| 2014/0179913 A1 | 6/2014 | Paullin et al. |
| 2015/0232785 A1 | 8/2015 | Paullin et al. |
| 2015/0232819 A1 | 8/2015 | Paullin et al. |
| 2018/0265646 A1* | 9/2018 | Nam ..................... C08J 3/075 |

FOREIGN PATENT DOCUMENTS

| CN | 1283633 A | 2/2001 |
|---|---|---|
| WO | 2003008618 A2 | 1/2003 |
| WO | 2009109407 A2 | 9/2009 |
| WO | 2010129839 A1 | 11/2010 |

OTHER PUBLICATIONS

McCabe et al. Infect. Immun. Dec. 1985 vol. 50 No. 3 771-777 (Year: 1985).*
Accession Q9LCH3. Oct. 1, 2000. (Year: 2000).*
Accession E9DPB1. Apr. 5, 2011. (Year: 2011).*
Accession Q55264. Nov. 1, 1996. (Year: 1996).*
Accession M4JBT9. May 29, 2013. (Year: 2013).*
Accession F3SJ66. Jun. 28, 2011. (Year: 2011).*
Declaration of Yefim B. Brun Under 37 C.F.R. 1.132 Filed in U.S. Appl. No. 14/619,174, Nov. 30, 2016.
Smith, PhD, Building the Biorefinery: Chemicals From Agricultural Resources, ADM Research, Undated, pp. 1-38.
Fujiwara et al., Genbank Accession No. BAA95201.1, Glucosyltransferase (*Streptococcus oralis*), May 2, 2008.
Abo et al., Peptide Sequences for Sucrose Splittng and Glucan Binding Within *Streptococcus sobrinus* Glucosyltransferase (Water-Insoluble Glucan Synthetase), Journal of Bacteriology, vol. 173, No. 3 (1991), pp. 989-996.
Andre et al., Sucrose-Utilizing Transglucosidases for Biocatalysis, Top Curr Chem, vol. 294 (2010), pp. 25-48.

(Continued)

*Primary Examiner* — Christian L Fronda

(57) ABSTRACT

Compositions are disclosed herein comprising poly alpha-1,3-glucan or poly alpha-1,3-1,6-glucan polymer having an open-cell pore structure with an average pore size of about 100 nm to about 3000 nm in diameter. Such polymers have enhanced aqueous liquid absorption capacity, and can be comprised in various products having aqueous liquid absorption function. Methods of preparing glucan polymers of the compositions provided herein are also disclosed.

20 Claims, 2 Drawing Sheets

Figure 1:
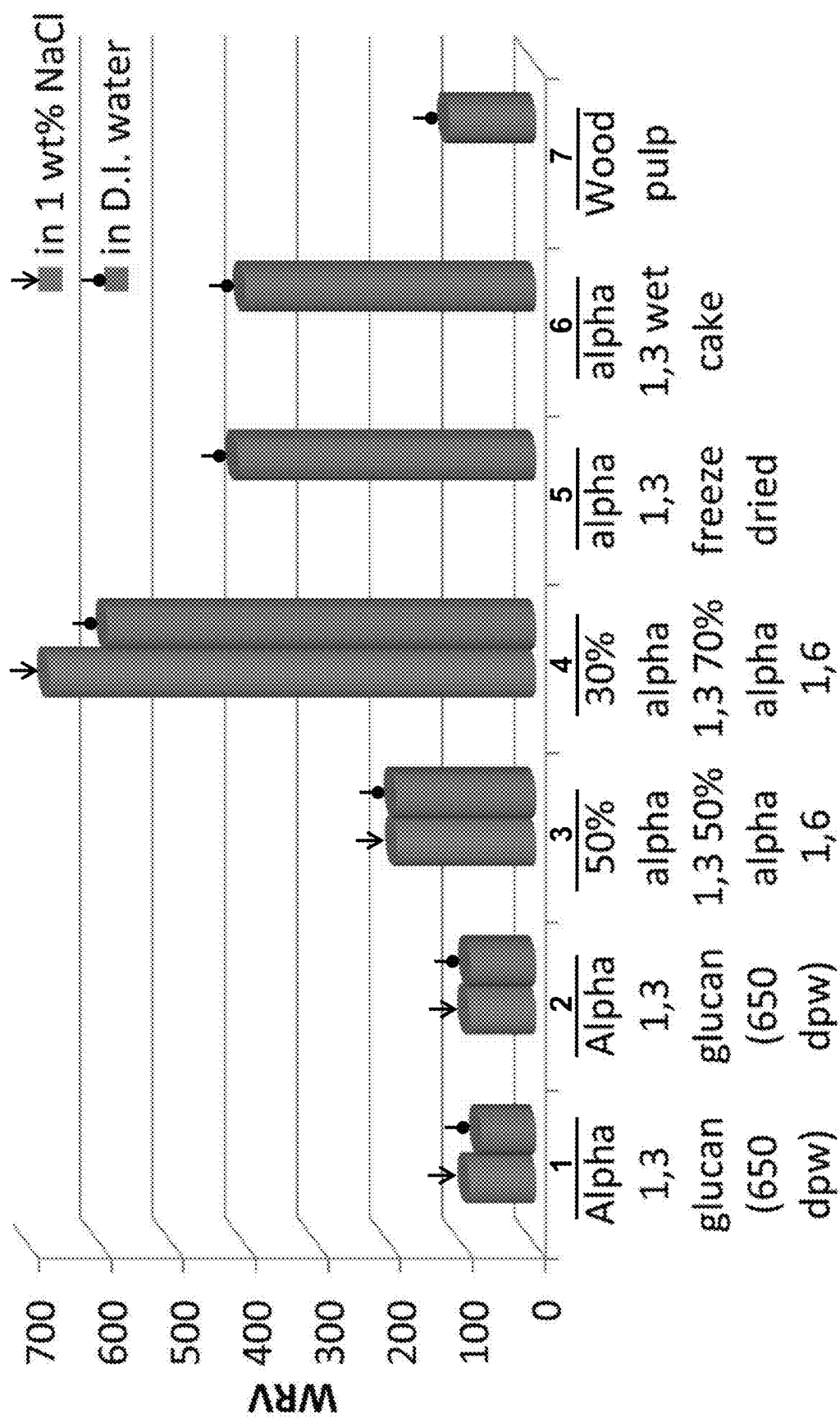

Specification includes a Sequence Listing.

(56) References Cited

OTHER PUBLICATIONS

Bao et al., Chemical Modifications of the (1→3)-α-D-Glucan From Spores of Ganoderma Lucidum and Investigation of Their Physicochemical Properties and Immunological Activity, Carbohydrate Research, vol. 336 (2001), pp. 127-140.
Cantarel et al., The Carbohydrate-Active Enzymes Database (CAZY): An Expert Resource for Glycogenomics, Nucleic Acids Research, vol. 37 (2009), Database Issue D233-D238.
Cote et al., Isolation and Partial Characterization of an Extracellular Glucansucrase From Leuconostoc Mesenteroides NRRL B-1355 That Synthesizes an Alternating (1→6), (1→3)-α-D-Glucan, Carbohydrate Research, vol. 101 (1982), pp. 57-74.
Cote et al., Some Structural Features of an Insoluble α-D-Glucan From a Mutant Strain of Leuconostoc Mesenteroides NRRL B-1355, Journal of Industrial Microbiology & Biotechnology, Voll. 23 (1999), pp. 656-660.
Fujiwara et al., Purification, Characterization, and Molecular Analysis of the Gene Encoding Glucosyltransferase From *Streptococcus oralis*, Infection and Immunity, vol. 65, No. 5 (2000), pp. 2475-2483.
Hamada et al., Interaction of Glucosyltransferase From *Streptococcus mutans* With Various Glucans, Journal of General Microbiology, vol. 116 (1980), pp. 51-59.
Hellmuth et al., Engineering the Glucansucrase GTFR Enzyme Reaction and Glycosidic Bond Specificity: Toward Tailor-Made Polymer and Oligosaccharide Products, Biochemistry, vol. 47 (2008), pp. 6678-6684.
Jeanes et al., Characterization and Classification of Dextrans From Ninety-Six Strains of Bacteria (Contribution From the Starch and Dextrose Section, Northern Utilization Research Branch), vol. 76, Oct. 20, 1954, pp. 5041-5052.
Joucla et al., Construction of a Fully Active Truncated Alternansucrase Partially Deleted of Its Carboxy-Terminal Domain, FEBS Letters, vol. 580 (2006), pp. 763-768.
Konishi et al., Structure and Enzymatic Properties of Genetically Truncated Forms of the Water-Insoluble Glucan-Synthesizing Glucosyltransferase From *Streptococcus sobrinus*, J. Biochem., vol. 126 (1999), pp. 287-295.
Kiho et al., (1→3)-α-D-Glucan From an Alkaline Extract of Agrocybe Cylindracea, and Antitumor Activity of Its O-(Carboxy-Methyl)ated Derivatives, Carbohydrate Research, vol. 189 (1989), pp. 273-279.
Maruyama et al., Comparative Genomic Analyses of *Streptococcus mutans* Provide Insights Into Chromosomal Shuffling and Species-Specific Content, BMC Genomics, vol. 10, No. 358 (2009), pp. 1-21.
Misaki et al., Structure of the Dextran of Leuconosoc Mesenteroides B-1355, Carbohydrate Research, vol. 84 (1980), pp. 273-285.
Monchois et al., Glucansucrases: Mechanism of Action and Structure-Function Relationships, FEMS Microbiology Reviews, vol. 23 (1999), pp. 131-151.
Monchois et al., Isolation of an Active Catalytic Core of *Streptococcus downei* MFE28 GTF-I Glucosyltransferase, Journal of Bacteriology, vol. 181, No. 7 (1999), pp. 2290-2292.
Monchois et al., Cloning and Sequencing of a Gene Coding for a Novel Dextransucrase From Leuconostoc Mesenteroides NRRL B-1299 Synthesizing Only α(1-6) and α(1-3) Linkages, Gene, vol. 182 (1996), pp. 23-32.
Sannino et al., Biodegradable Cellulose-Based Hydrogels: Design and Applications, Materials, vol. 2 (2009), pp. 353-373.
Shida et al., A (1→3)-α-D-Glucan Isolated From the Fruit Bodies of Lentinus Edodes, Carbohydrate Research, vol. 60 (1978), pp. 117-127.
Shimotsuura et al., Biochemical and Molecular Characterization of a Novel Type of Mutanase From *Paenibacillus* Sp. Strain RM1: Identification of Its Mutan-Binding Domain, Essential for Degradation of *Streptococcus mutans* Biofiloms, Applied and Environmental Microbiology, vol. 74, No. 9 (2008), pp. 2759-2765.
Simpson et al., Four Glucosyltransferases, GTFJ, GTFK, GTFL and GTFM, From *Streptococcus salivarius* ATCC 25975, Microbiology, vol. 141 (1995), pp. 1451-1460.
Simpson et al., *Streptococcus salivarius* ATCC 25975 Possesses at Least Two Genes Coding for Primer-Independent Glucosyltransferases, Infection and Immunity, vol. 63, No. 2 (1995), pp. 609-621.
Swistowska et al., Heterologous Hyper-Expression of a Glucansucrase-Type Glycosyltransferase Gene, Appl. Microbiol. Biotechnol, vol. 79 (2008), pp. 255-261.
Tsumori et al., Purification and Properties of Extracellular Glucosyltransferase Synthesizing 1,6-, 1,3-α-D-Glucan From *Streptococcus mutans* Serotype A, Journal of General Microbiology, vol. 131 (1985), pp. 3347-3353.

* cited by examiner

POLYSACCHARIDE COMPOSITIONS FOR ABSORBING AQUEOUS LIQUID

This application is a continuation of application Ser. No. 14/965,961 (filed Dec. 11, 2015), which claims the benefit of U.S. Provisional Application No. 62/095,423 (filed Dec. 22, 2014). Both of these prior applications are incorporated herein by reference in their entirety.

FIELD OF INVENTION

The present disclosure is in the field of polysaccharides. Specifically, the disclosure pertains to poly alpha-1,3-glucan and poly alpha-1,3-1,6-glucan compositions having enhanced aqueous liquid absorption ability.

REFERENCE TO SEQUENCE LISTING SUBMITTED ELECTRONICALLY

The official copy of the sequence listing is submitted electronically via EFS-Web as an ASCII formatted sequence listing with a file named 20151211 CL6319USNP_SequenceListing.txt created on Dec. 3, 2015, and having a size of 82 kilobytes and is filed concurrently with the specification. The sequence listing contained in this ASCII-formatted document is part of the specification and is herein incorporated by reference in its entirety.

BACKGROUND

Driven by a desire to find new structural polysaccharides using enzymatic syntheses or genetic engineering of microorganisms, researchers have discovered polysaccharides that are biodegradable and can be made economically from renewably sourced feedstocks. One such polysaccharide is poly alpha-1,3-glucan, a glucan polymer characterized by having alpha-1,3-glycosidic linkages.

Poly alpha-1,3-glucan has been isolated by contacting an aqueous solution of sucrose with a glucosyltransferase (gtf) enzyme isolated from *Streptococcus salivarius* (Simpson et al., *Microbiology* 141:1451-1460, 1995). U.S. Pat. No. 7,000,000 disclosed the preparation of a polysaccharide fiber using an *S. salivarius* gtfJ enzyme. At least 50% of the hexose units within the polymer of this fiber were linked via alpha-1,3-glycosidic linkages. The disclosed polymer formed a liquid crystalline solution when it was dissolved above a critical concentration in a solvent or in a mixture comprising a solvent. From this solution continuous, strong, cotton-like fibers, highly suitable for use in textiles, were spun and used.

Development of new glucan polysaccharide compositions is desirable given their potential utility in various applications, such as in aqueous liquid absorption.

SUMMARY OF INVENTION

In one embodiment, the present disclosure concerns a composition comprising a polymer selected from the group consisting of poly alpha-1,3-glucan and poly alpha-1,3-1,6-glucan, wherein the polymer comprises an open-cell pore structure with an average pore size of about 100 nm to about 3000 nm in diameter, and wherein the polymer can absorb aqueous liquid.

In another embodiment, the poly alpha-1,3-glucan or poly alpha-1,3-1,6-glucan polymer is a product of an enzymatic reaction comprising water, sucrose and a glucosyltransferase enzyme. In another embodiment, the polymer is not completely dried after its production in the reaction. In another embodiment, the polymer is freeze-dried after its production in the reaction, and the freeze-drying is the first time the polymer is dried. The polymer that is freeze-dried is poly alpha-1,3-glucan in another embodiment.

In another embodiment, the polymer has a water retention value (WRV) of at least about 150.

In another embodiment, the poly alpha-1,3-glucan has at least 50% alpha-1,3 glucosidic linkages and a degree of polymerization of at least 100.

In another embodiment, the poly alpha-1,3-1,6-glucan has (i) at least 30% alpha-1,3 glucosidic linkages, (ii) at least 30% alpha-1,6 glucosidic linkages, and (iii) a degree of polymerization of at least 1000, and, optionally, the alpha-1,3 linkages and alpha-1,6 linkages do not consecutively alternate with each other.

In another embodiment, the composition is a personal care product, household product, medical product, or industrial product.

Another embodiment of the present disclosure concerns a method for preparing a polymer selected from the group consisting of poly alpha-1,3-glucan and poly alpha-1,3-1,6-glucan. This method comprises: (a) contacting at least water, sucrose, and a glucosyltransferase enzyme, whereby poly alpha-1,3-glucan or poly alpha-1,3-1,6-glucan polymer is produced; (b) washing the polymer produced in step (a) to prepare a wet cake comprising polymer and residual water; and (c) removing the residual water from the wet cake such that the structure of the polymer is not substantially changed; wherein the polymer resulting from step (c) comprises an open-cell pore structure with an average pore size of about 100 nm to about 3000 nm in diameter, and wherein the polymer can absorb aqueous liquid.

In another embodiment, step (c) of preparing poly alpha-1,3-1,6-glucan or poly alpha-1,3-1,6-glucan is performed by freeze-drying the wet cake. The polymer that is freeze-dried is poly alpha-1,3-glucan in another embodiment.

Another embodiment of the present disclosure concerns a method for preparing poly alpha-1,3-1,6-glucan. This method comprises (a) contacting at least water, sucrose, and a glucosyltransferase enzyme that synthesizes poly alpha-1,3-1,6-glucan, whereby poly alpha-1,3-1,6-glucan is produced; (b) washing the poly alpha-1,3-1,6-glucan produced in step (a) to prepare a wet cake comprising poly alpha-1,3-1,6-glucan and residual water; and (c) removing the residual water from the wet cake; wherein the poly alpha-1,3-1,6-glucan resulting from step (c) can absorb aqueous liquid.

In another embodiment, the glucosyltransferase enzyme for producing poly alpha-1,3-1,6-glucan comprises an amino acid sequence that is at least 90% identical to SEQ ID NO:2, SEQ ID NO:4, SEQ ID NO:6, SEQ ID NO:8, or SEQ ID NO:10.

In another embodiment, step (c) of preparing poly alpha-1,3-1,6-glucan is performed by oven drying.

BRIEF DESCRIPTION OF THE DRAWINGS AND SEQUENCES

FIG. 1: Water-retention values (WRV) of poly alpha-1,3-glucan and poly alpha-1,3-1,6-glucan polymers in 1 wt % NaCl solution or deionized (DI) water. Note that these polymers are not water-soluble, and have not been cross-linked. Refer to Example 7.

Figure 2:
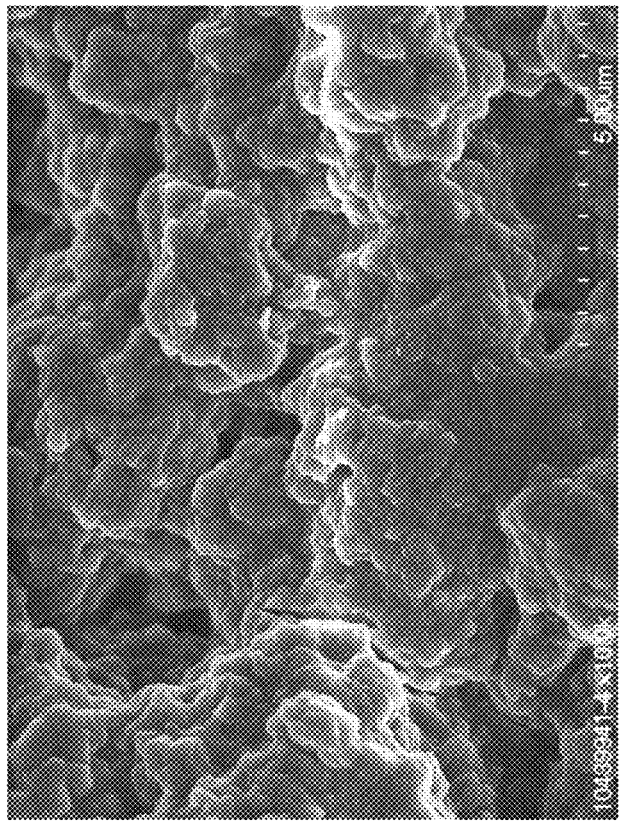
Figure 2:
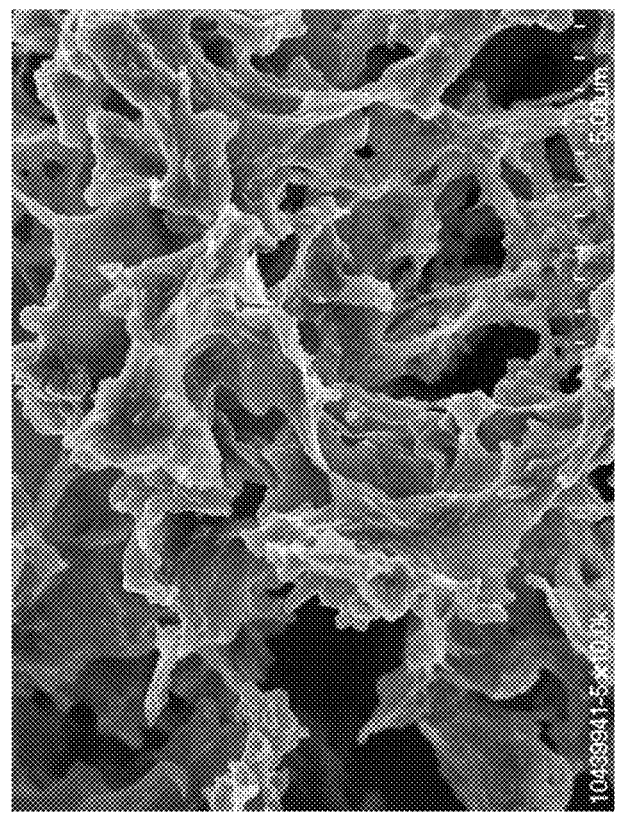

FIG. 2: Scanning electron micrograph (SEM) image of freeze-dried poly alpha-1,3-glucan wet cake (left) and oven-dried poly alpha-1,3-glucan wet cake (right). The small vertical lines of each scale provided in the bottom right portions of both images are spaced at 500-nm increments (distance from left-most bar to right-most bar is 5 microns). Refer to Example 7.

TABLE 1

Summary of Nucleic Acid and Protein SEQ ID Numbers

| Description | Nucleic acid SEQ ID NO. | Protein SEQ ID NO. |
|---|---|---|
| "4297 gtf", *Streptococcus oralis*. DNA codon-optimized for expression in *E. coli*. The first 228 amino acids of the protein are deleted compared to GENBANK Identification No. 7684297; a start methionine is included. | 1 | 2 (1348 aa) |
| "3298 gtf", *Streptococcus* sp. C150. The first 209 amino acids of the protein are deleted compared to GENBANK Identification No. 322373298; a start methionine is included. | 3 | 4 (1242 aa) |
| "0544 gtf", *Streptococcus mutans*. DNA codon-optimized for expression in *E. coli*. The first 164 amino acids of the protein are deleted compared to GENBANK Identification No. 290580544; a start methionine is included. | 5 | 6 (1313 aa) |
| "5618 gtf", *Streptococcus sanguinis*. DNA codon-optimized for expression in *E. coli*. The first 223 amino acids of the protein are deleted compared to GENBANK Identification No. 328945618; a start methionine is included. | 7 | 8 (1348 aa) |
| "2379 gtf", *Streptococcus salivarius*. DNA codon-optimized for expression in *E. coli*. The first 203 amino acids of the protein are deleted compared to GENBANK Identification No. 662379; a start methionine is included. | 9 | 10 (1247 aa) |

DETAILED DESCRIPTION

The disclosures of all cited patent and non-patent literature are incorporated herein by reference in their entirety.

Unless otherwise disclosed, the terms "a" and "an" as used herein are intended to encompass one or more (i.e., at least one) of a referenced feature.

Where present, all ranges are inclusive and combinable, except as otherwise noted. For example, when a range of "1 to 5" is recited, the recited range should be construed as including ranges "1 to 4", "1 to 3", "1-2", "1-2 & 4-5", "1-3 & 5", and the like.

The term "glucan" herein refers to a polysaccharide of D-glucose monomers that are linked by glucosidic linkages, which are a type of glycosidic linkage. An "alpha-glucan" herein refers to a glucan in which the constituent D-glucose monomers are alpha-D-glucose monomers.

The terms "glycosidic linkage", "glycosidic bond" and the like are used interchangeably herein and refer to the type of covalent bond that joins a carbohydrate molecule to another carbohydrate molecule. The terms "glucosidic linkage", "glucosidic bond" and the like are used interchangeably herein and refer to a glycosidic linkage between two glucose molecules. The term "alpha-1,3-glycosidic linkage" as used herein refers to the type of covalent bond that joins alpha-D-glucose molecules to each other through carbons 1 and 3 on adjacent alpha-D-glucose rings. The term "alpha-1,6-glycosidic linkage" as used herein refers to the type of covalent bond that joins alpha-D-glucose molecules to each other through carbons 1 and 6 on adjacent alpha-D-glucose rings. Herein, "alpha-D-glucose" will be referred to as "glucose." All glycosidic linkages disclosed herein are alpha-glucosidic linkages, except where otherwise noted.

The glycosidic linkage profile of a glucan polymers herein can be determined using any method known in the art. For example, a linkage profile can be determined using methods that use nuclear magnetic resonance (NMR) spectroscopy (e.g., $^{13}$C NMR or $^1$H NMR). These and other methods that can be used are disclosed in *Food Carbohydrates: Chemistry, Physical Properties, and Applications* (S. W. Cui, Ed., Chapter 3, S. W. Cui, Structural Analysis of Polysaccharides, Taylor & Francis Group LLC, Boca Raton, Fla., 2005), which is incorporated herein by reference.

The terms "poly alpha-1,3-glucan", "alpha-1,3-glucan polymer" and the like are used interchangeably herein. Poly alpha-1,3-glucan is a polymer comprising glucose monomeric units linked together by glucosidic linkages, wherein at least about 50% of the glucosidic linkages are alpha-1,3-glucosidic linkages. Poly alpha-1,3-glucan polymer can be synthesized, for example, by following the procedures disclosed in U.S. Appl. Publ. No. 2014/0179913, which is incorporated herein by reference.

The terms "poly alpha-1,3-1,6-glucan", "alpha-1,3-1,6-glucan polymer", "poly (alpha-1,3)(alpha-1,6) glucan" and the like are used interchangeably herein (note that the order of the linkage denotations "1,3" and "1,6" in these terms is of no moment). Poly alpha-1,3-1,6-glucan herein is a polymer comprising glucose monomeric units linked together by glucosidic linkages, wherein at least about 30% of the glucosidic linkages are alpha-1,3-glucosidic linkages, and at least about 30% of the glucosidic linkages are alpha-1,6-glucosidic linkages. Poly alpha-1,3-1,6-glucan is a type of polysaccharide containing a mixed glycosidic linkage content. The meaning of the term poly alpha-1,3-1,6-glucan in certain embodiments herein excludes "alternan," which is a glucan containing alpha-1,3 linkages and alpha-1,6 linkages that consecutively alternate with each other (U.S. Pat. No. 5,702,942, U.S. Pat. Appl. Publ. No. 2006/0127328). Alpha-1,3 and alpha-1,6 linkages that "consecutively alternate" with each other can be visually represented by . . . G-1,3-G-1,6-G-1,3-G-1,6-G-1,3-G-1,6-G-1,3-G- . . . , for example, where G represents glucose.

The "molecular weight" of a glucan polymers herein can be represented as number-average molecular weight ($M_n$) or as weight-average molecular weight ($M_w$), the units of which are in Daltons or grams/mole. Alternatively, molecular weight can be represented as $DP_w$ (weight average degree of polymerization) or $DP_n$ (number average degree of polymerization). Various means are known in the art for calculating these molecular weight measurements such as with high-pressure liquid chromatography (HPLC), size exclusion chromatography (SEC), or gel permeation chromatography (GPC).

The term "sucrose" herein refers to a non-reducing disaccharide composed of an alpha-D-glucose molecule and a beta-D-fructose molecule linked by an alpha-1,2-glycosidic bond. Sucrose is known commonly as table sugar.

The terms "glucosyltransferase", "glucosyltransferase enzyme", "gtf", "glucansucrase" and the like are used interchangeably herein. The activity of a glucosyltransferase enzyme herein catalyzes the reaction of sucrose substrate to make the products glucan (e.g., poly alpha-1,3-glucan or poly alpha-1,3-1,6-glucan) and fructose. Other products (byproducts) of a glucosyltransferase reaction can include glucose and various soluble oligosaccharides (e.g., DP2-DP7) including leucrose. Wild type forms of glucosyltransferase enzymes generally contain (in the N-terminal to C-terminal direction) a signal peptide, a variable domain, a catalytic domain, and a glucan-binding domain. A glucosyltransferase herein is classified under the glycoside hydrolase family 70 (GH70) according to the CAZy (Carbohydrate-Active EnZymes) database (Cantarel et al., *Nucleic Acids Res.* 37:D233-238, 2009).

The terms "enzymatic reaction", "glucosyltransferase reaction", "glucan synthesis reaction", "gtf reaction", "reaction composition" and the like are used interchangeably herein and generally refer to a reaction that initially comprises water, sucrose, at least one active glucosyltransferase enzyme, and optionally other components. Components that can be further present in a glucan synthesis reaction typically after it has commenced include fructose, glucose, soluble oligosaccharides (e.g., DP2-DP7) such as leucrose, and soluble and/or insoluble alpha-glucan product(s) of DP8 or higher (e.g., DP100 and higher). It would be understood that certain glucan products, such as poly alpha-1,3-glucan and poly alpha-1,3-1,6-glucan with a degree of polymerization (DP) of at least 8 or 9, are typically water-insoluble and thus are not dissolved in a glucan synthesis reaction, but rather may be present out of solution. It is in a glucan synthesis reaction where the step of contacting at least water, sucrose and a glucosyltransferase enzyme is performed. The term "under suitable reaction conditions" as used herein, refers to reaction conditions that support conversion of sucrose to glucan polymer (e.g., poly alpha-1,3-glucan or poly alpha-1,3-1,6-glucan) via glucosyltransferase enzyme activity. An enzymatic reaction herein is not believed to occur in nature.

The "percent dry solids" of a glucosyltransferase reaction refers to the wt % of all the sugars in a glucosyltransferase reaction. The percent dry solids of a gtf reaction can be calculated, for example, based on the amount of sucrose used to prepare the reaction.

The "yield" of glucan polymer (e.g., poly alpha-1,3-glucan or poly alpha-1,3-1,6-glucan) by a glucosyltransferase reaction herein represents the weight of glucan product expressed as a percentage of the weight of sucrose substrate that is converted in the reaction. For example, if 100 g of sucrose in a gtf reaction is converted to products, and 10 g of the products is insoluble glucan polymer, the yield of such polymer would be 10%. This yield calculation can be considered as a measure of selectivity of the reaction toward insoluble glucan polymer.

The terms "pore structures", "pores", "cells", "voids" and the like as used herein refer to small spaces located within an otherwise solid composition. Such small spaces are typically interconnected to some degree by narrow passages. An "open-cell pore structure" refers to a pore that is accessible from the outside of a composition having the open-cell pore structure. For example, an aqueous liquid applied to a composition having an open-cell pore structure can enter the open-cell pore. The opposite of an open-cell pore structure is a "closed-cell pore structure", which is a pore that is closed off from the outside of a composition having the closed-cell pore structure.

The term "pore size" as used herein can refer to any measurement (e.g. pore diameter or volume) useful for describing the size of a pore. The term "pore diameter" can in some aspects refer to the longest distance that can be measured between two internal wall surfaces of a pore. The term "average pore diameter" can in some aspects refer to an average of the diameters of at least 100, 500, 1000 or more pores comprised within a composition.

The term "absorb" as used herein refers to the action of taking up (soaking up) an aqueous liquid. A composition herein can absorb an aqueous liquid since it comprises open-cell pores, which allow aqueous liquid access to the inside of the pores. Absorption herein can be measured in terms of water retention value (WRV), or as g aqueous liquid/g glucan polymer (the maximum amount of aqueous liquid that can be soaked into and retained by a certain amount of glucan polymer), for example. WRV can be calculated with respect to any aqueous liquid herein using the following formula, for example: ((mass of wet polymer−mass of dry polymer)/mass of dry polymer)*100.

The terms "aqueous liquid", "aqueous fluid" and the like as used herein can refer water or a water solution. A "water solution" herein can comprise one or more dissolved salts, where the maximal total salt concentration can be about 3.5 wt % in some embodiments. Although aqueous liquids herein typically comprise water as the only solvent in the liquid, an aqueous liquid can optionally comprise one or more other solvents (e.g., polar organic solvent) that are miscible in water.

The term "not completely dried" as used to characterize a glucan polymer synthesized in a gtf reaction refers to polymer that has more than about 3 wt % water.

The terms "freeze-drying", lyophilization" and the like as used herein refer to a process in which a wet composition (e.g., glucan polymer wet cake herein) is rapidly frozen (freezing step), and then subjected to a high vacuum (to provide lower air pressure) to remove frozen water by sublimation (primary drying step). Freeze-drying herein can optionally comprise a secondary drying step in which the temperature is raised higher (and pressure typically lowered further) than in the primary drying phase.

A "slurry" of poly alpha-1,3-glucan or poly alpha-1,3-1,6-glucan herein refers to an aqueous mixture comprising the components of a gtf reaction such as insoluble glucan polymer product (e.g., poly alpha-1,3-glucan or poly alpha-1,3-1,6-glucan), sucrose, one or more glucosyltransferase enzymes, glucose and fructose. This composition is a slurry since the glucan polymer product is not dissolved therein.

A "wet cake" of poly alpha-1,3-glucan or poly alpha-1,3-1,6-glucan herein refers to glucan polymer product (e.g., poly alpha-1,3-glucan or poly alpha-1,3-1,6-glucan) that has been separated from a gtf reaction or slurry and washed with water or an aqueous solution. Glucan polymer product is not completely dried when preparing a wet cake. A wet cake preparation typically comprises at least one step of filtering the glucan polymer product.

The terms "percent by volume", "volume percent", "vol %", "v/v %" and the like are used interchangeably herein. The percent by volume of a solute in a solution can be determined using the formula: [(volume of solute)/(volume of solution)]×100%.

The terms "percent by weight", "weight percentage (wt %)", "weight-weight percentage (% w/w)" and the like are used interchangeably herein. Percent by weight refers to the percentage of a material on a mass basis as it is comprised in a composition, mixture, or solution.

The term "increased" as used herein can refer to a quantity or activity that is at least about 1%, 2%, 3%, 4%, 5%, 6%, 7%, 8%, 9%, 10%, 11%, 12%, 13%, 14%, 15%, 16%, 17%, 18%, 19%, 20%, 50%, 100%, or 200% more than the quantity or activity for which the increased quantity or activity is being compared. The terms "increased", "elevated", "enhanced", "greater than", "improved" and the like are used interchangeably herein.

The terms "sequence identity" or "identity" as used herein with respect to polynucleotide or polypeptide sequences refer to the nucleic acid residues or amino acid residues in two sequences that are the same when aligned for maximum correspondence over a specified comparison window. Thus, "percentage of sequence identity" or "percent identity"

refers to the value determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the results by 100 to yield the percentage of sequence identity. It would be understood that, when calculating sequence identity between a DNA sequence and an RNA sequence, T residues of the DNA sequence align with, and can be considered "identical" with, U residues of the RNA sequence. For purposes of determining "percent complementarity" of first and second polynucleotides, one can obtain this by determining (i) the percent identity between the first polynucleotide and the complement sequence of the second polynucleotide (or vice versa), for example, and/or (ii) the percentage of bases between the first and second polynucleotides that would create canonical Watson and Crick base pairs.

The Basic Local Alignment Search Tool (BLAST) algorithm, which is available online at the National Center for Biotechnology Information (NCBI) website, may be used, for example, to measure percent identity between or among two or more of the polynucleotide sequences (BLASTN algorithm) or polypeptide sequences (BLASTP algorithm) disclosed herein. Alternatively, percent identity between sequences may be performed using a Clustal algorithm (e.g., ClustalW, ClustalV, or Clustal-Omega). For multiple alignments using a Clustal method of alignment, the default values may correspond to GAP PENALTY=10 and GAP LENGTH PENALTY=10. Default parameters for pairwise alignments and calculation of percent identity of protein sequences using a Clustal method may be KTUPLE=1, GAP PENALTY=3, WINDOW=5 and DIAGONALS SAVED=5. For nucleic acids, these parameters may be KTUPLE=2, GAP PENALTY=5, WINDOW=4 and DIAGONALS SAVED=4. Alternatively still, percent identity between sequences may be performed using an EMBOSS algorithm (e.g., needle) with parameters such as GAP OPEN=10, GAP EXTEND=0.5, END GAP PENALTY=false, END GAP OPEN=10, END GAP EXTEND=0.5 using a BLOSUM matrix (e.g., BLOSUM62).

Various polypeptide amino acid sequences and polynucleotide sequences are disclosed herein as features of certain embodiments. Variants of these sequences that are at least about 70-85%, 85-90%, or 90%-95% identical to the sequences disclosed herein can be used or referenced. Alternatively, a variant amino acid sequence or polynucleotide sequence can have at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% identity with a sequence disclosed herein. The variant amino acid sequence or polynucleotide sequence has the same function/activity of the disclosed sequence, or at least about 80%, 81%, 82%, 83%, 84%, 85%, 86%, 87%, 88%, 89%, 90%, 91%, 92%, 93%, 94%, 95%, 96%, 97%, 98%, or 99% of the function/activity of the disclosed sequence. Any polypeptide amino acid sequence disclosed herein not beginning with a methionine can typically further comprise at least a start-methionine at the N-terminus of the amino acid sequence. Any polypeptide amino acid sequence disclosed herein beginning with a methionine can optionally be considered without this methionine residue (i.e., a polypeptide sequence can be referred to in reference to the position-2 residue to the C-terminal residue of the sequence).

All the amino acid residues at each amino acid position of the proteins disclosed herein are examples. Given that certain amino acids share similar structural and/or charge features with each other (i.e., conserved), the amino acid at each position of a protein herein can be as provided in the disclosed sequences or substituted with a conserved amino acid residue ("conservative amino acid substitution") as follows:

1. The following small aliphatic, nonpolar or slightly polar residues can substitute for each other: Ala (A), Ser (S), Thr (T), Pro (P), Gly (G);
2. The following polar, negatively charged residues and their amides can substitute for each other: Asp (D), Asn (N), Glu (E), Gln (Q);
3. The following polar, positively charged residues can substitute for each other: His (H), Arg (R), Lys (K);
4. The following aliphatic, nonpolar residues can substitute for each other: Ala (A), Leu (L), Ile (I), Val (V), Cys (C), Met (M); and
5. The following large aromatic residues can substitute for each other: Phe (F), Tyr (Y), Trp (W).

The term "isolated" as used herein refers to a polynucleotide, polypeptide, or glucan polymer that has been completely or partially purified. In some instances, the isolated polynucleotide, polypeptide, or glucan polymer is part of a greater composition, buffer system, or reagent mix. For example, isolated glucan polymer herein can be comprised within a personal care product, household product, medical product, or industrial product herein. Such a product does not occur in nature. Another example is an isolated glucosyltransferase enzyme or reaction. Glucan polymer compositions of the present disclosure are synthetic/man-made, and/or exhibit properties not believed to naturally occur.

Development of new glucan polysaccharide compositions is desirable given their potential utility in various applications, such as in aqueous liquid absorption.

Embodiments of the present disclosure concern a composition comprising a polymer selected from the group consisting of poly alpha-1,3-glucan and poly alpha-1,3-1,6-glucan, wherein the polymer comprises an open-cell pore structure with an average pore size of about 100 nm to about 3000 nm in diameter, and wherein the polymer can absorb aqueous liquid. Significantly, such compositions have an enhanced ability to absorb aqueous liquids/fluids, even though the compositions have not been subject to any chemical processing such as cross-linking, which is typically used to enhance the absorption capability of polysaccharides and other polymer materials. Also of significance, the disclosed compositions exhibit an ability to absorb saline solutions at about the same level of absorption of deionized water. In contrast, other types of materials that have shown an ability to absorb deionized water typically exhibit low saline solution absorption ability. The enhanced absorption capacity of the presently disclosed compositions, coupled with there being minimal or no chemical processing in their production, renders the disclosed compositions as being particularly useful in personal care products, for example.

A poly alpha-1,3-glucan or poly alpha-1,3-1,6-glucan polymer as comprised in a composition herein can absorb an aqueous liquid. An aqueous liquid can be water (e.g., deionized water) for instance. An aqueous liquid in certain other aspects can be an aqueous solution, such as a salt solution (saline solution). A salt solution can optionally comprise about, or at least about, 0.01, 0.025, 0.05, 0.075, 0.1, 0.25, 0.5, 0.75, 1.0, 1.25, 1.5, 1.75, 2.0, 2.5, 3.0, 3.5, 0.01-3.5, 0.5-3.5, 0.5-2.5, or 0.5-1.5 wt % of salt (such wt %'s typically refer to the total concentration of one or more salts). Examples of a salt that can be used in an aqueous solution herein include one or more sodium salts (e.g., NaCl, $Na_2SO_4$). Other non-limiting examples of salts include those having (i) an aluminum, ammonium, barium, calcium, chromium (II or III), copper (I or II), iron (II or III), hydrogen, lead (II), lithium, magnesium, manganese (II or III), mercury (I or II), potassium, silver, sodium strontium, tin (II or IV), or zinc cation, and (ii) an acetate, borate, bromate, bromide, carbonate, chlorate, chloride, chlorite, chromate, cyanamide, cyanide, dichromate, dihydrogen phosphate, ferricyanide, ferrocyanide, fluoride, hydrogen carbonate, hydrogen phosphate, hydrogen sulfate, hydrogen sulfide, hydrogen sulfite, hydride, hydroxide, hypochlorite, iodate, iodide, nitrate, nitride, nitrite, oxalate, oxide, perchlorate, permanganate, peroxide, phosphate, phosphide, phosphite, silicate, stannate, stannite, sulfate, sulfide, sulfite, tartrate, or thiocyanate anion. Thus, any salt having a cation from (i) above and an anion from (ii) above can be in an aqueous liquid as presently disclosed, for example.

In certain aspects, the absorption capacity of poly alpha-1,3-glucan or poly alpha-1,3-1,6-glucan polymer as comprised in a composition herein towards water is equal with, or similar to, the polymer's absorption capacity toward an aqueous solution herein (e.g., NaCl solution such as 1 wt % NaCl). All other conditions being the same or very similar, a poly alpha-1,3-glucan or poly alpha-1,3-1,6-glucan polymer herein can exhibit levels of water absorption and aqueous solution absorption that differ from each other by less than about 20%, 19%, 18%, 17%, 16%, 15%, 14%, 13%, 12%, 11%, 10%, 9%, 8%, 7%, 6%, 5%, 4%, 3%, 2%, or 1%, for example. The level of absorption can be measured by any means known in the art, such as with the protocol presently disclosed in Example 7 (below) regarding measuring WRV (water retention value).

Absorption of an aqueous liquid by a poly alpha-1,3-glucan or poly alpha-1,3-1,6-glucan polymer as comprised in a composition herein can be gauged by measuring the WRV of the composition, for example. WRV herein can be measured by any means known in the art, such as with the protocol presently disclosed in Example 7 (below). Briefly, WRV can be calculated using the following formula: ((mass of wet polymer−mass of dry polymer)/mass of dry polymer) *100. WRV can be measured with respect to any aqueous liquid as presently disclosed, for example. Thus, while the term WRV contains the word "water", it would be understood that a polymer WRV can be measured regarding any type of aqueous liquid disclosed herein, such as an aqueous solution (e.g., saline solution such as an NaCl solution).

A poly alpha-1,3-glucan or poly alpha-1,3-1,6-glucan polymer as comprised in a composition herein can have a WRV of at least about 150 in certain embodiments. WRV in other examples can be at least about 200, 250, 300, 350, 400, 450, 500, 500, 600, 650, 700, or 750.

Absorption herein can optionally be measured in terms of the maximum amount of aqueous liquid that can be soaked into and retained by a certain amount of glucan polymer (g aqueous liquid/g glucan polymer). Glucan polymer with an absorption capacity of at least 15 g aqueous liquid/g glucan polymer can be characterized as being superabsorbent in some aspects.

A poly alpha-1,3-glucan or poly alpha-1,3-1,6-glucan polymer as comprised in a composition herein can have an open-cell pore structure. Such a polymer can optionally be characterized as having open pores. The entire polymer, or a portion thereof (e.g., at least about 20%, 30%, 40%, 50%, 60%, 70%, 80%, 90%, 95% by volume), as comprised in a composition herein can be in a porous form (e.g., spongy appearance on a nano-scale level). Pores herein can be dispersed throughout the entire polymer or portion thereof in a matrix-like or sponge-like pattern in some cases. The cells of a polymer herein can be continuous, or semi-continuous (e.g., at least 20%, 30%, 40%, 50%, 60%, 70%, 80%, or 90% of the pores are continuous with at least one immediately adjacent pore), for example (any two pores can be characterized as being continuous with each other if there is an open passage connecting them). In some embodiments, a poly alpha-1,3-glucan or poly alpha-1,3-1,6-glucan polymer does not comprise closed-cell pore structures (i.e., pores that are completely closed off and not continuous with any adjacent pores), or has less than 80%, 70%, 60%, 50%, 40%, 30%, 20% or 10% of pores that are closed-cell pores.

Open-pore structures of a poly alpha-1,3-glucan or poly alpha-1,3-1,6-glucan polymer composition herein have an average pore size of about 100 nm to about 3000 nm in diameter. Such embodiments can optionally be characterized as having an average pore diameter of about 100 nm to about 3000 nm. The average pore diameter in some aspects can be at least about 100, 250, 500, 750, 1000, 1250, 1500, 1750, 2000, 2250, 2500, 2750, or 3000 nm, or can range from about 100-3000, 100-2500, 100-2000, 100-1500, 100-1000, 100-500, 500-3000, 500-2500, 500-2000, 500-1500, 500-1000, 1000-3000, 1000-2500, 1000-2000, 1000-1500, 1500-3000, 1500-2500, 1500-2000, 2000-3000, 2000-2500, or 2500-3000 nm. Pore diameter can optionally be considered as the longest distance that can be measured between two internal wall surfaces of a pore. Pore diameter can be measured, for instance, using a planar cross-section of a pore. Average pore diameter can be determined by any means known in the art. For example, average pore diameter can be calculated based on the diameters measured for at least 100, 500, or 1000 pores. The pores of a polymer composition as presently disclosed can be characterized, in some aspects, as being uniform in size (e.g., standard deviation of measured pore diameter of less than about 200, 150, 100, or 50 nm).

A poly alpha-1,3-glucan or poly alpha-1,3-1,6-glucan polymer as comprised in a composition herein can be, for example, a product of an enzymatic reaction comprising water, sucrose and a glucosyltransferase enzyme (i.e., a gtf reaction).

A glucosyltransferase enzyme suitable for an enzymatic reaction herein may be obtained from any microbial source, such as a bacteria or fungus. Examples of bacterial glucosyltransferase enzymes are those derived from a *Streptococcus* species, *Leuconostoc* species or *Lactobacillus* species. Examples of *Streptococcus* species include *S. salivarius, S. sobrinus, S. dentirousetti, S. downei, S. mutans, S. oralis, S. gallolyticus* and *S. sanguinis*. Examples of *Leuconostoc* species include *L. mesenteroides, L. amelibiosum, L. argentinum, L. carnosum, L. citreum, L. cremoris, L. dextranicum* and *L. fructosum*. Examples of *Lactobacillus* species include *L. acidophilus, L. delbrueckii, L. helveticus, L. salivarius, L. casei, L. curvatus, L. plantarum, L. sakei, L. brevis, L. buchneri, L. fermentum* and *L. reuteri*.

A glucosyltransferase enzyme in certain embodiments for producing poly alpha-1,3-1,6-glucan can comprise, or consist of, an amino acid sequence that is at least 90%, 91%, 92%, 93%, 94%, 95%, 96%, 97%, 98%, or 99% identical to, SEQ ID NO:2, SEQ ID NO:4, SEQ ID NO:6, SEQ ID NO:8, or SEQ ID NO:10, wherein the glucosyltransferase enzyme has activity. Alternatively, a glucosyltransferase enzyme can comprise, or consist of, SEQ ID NO:2, SEQ ID NO:4, SEQ ID NO:6, SEQ ID NO:8, or SEQ ID NO:10.

The amino acid sequence of a glucosyltransferase enzyme in certain embodiments for producing poly alpha-1,3-1,6-glucan can be encoded by the polynucleotide sequence provided in SEQ ID NO:1, SEQ ID NO:3, SEQ ID NO:5, SEQ ID NO:7, or SEQ ID NO:9, for example. Alternatively, such an amino acid sequence can be encoded by a polynucleotide sequence that is at least 90%, 91%, 92%, 93%, 94%, 95%, 96%, 97%, 98%, or 99% identical to SEQ ID NO:1, SEQ ID NO:3, SEQ ID NO:5, SEQ ID NO:7, or SEQ ID NO:9.

A glucosyltransferase enzyme in certain embodiments for producing poly alpha-1,3-glucan can comprise, or consist of, an amino acid sequence as disclosed in U.S. Patent Appl. Publ. No. 2014-0087431, for example, which is incorporated herein by reference.

Still further examples of glucosyltransferase enzymes can be any as disclosed herein and that include 1-300 (or any integer there between [e.g., 10, 15, 20, 25, 30, 35, 40, 45, or 50]) residues on the N-terminus and/or C-terminus. Such additional residues may be from a corresponding wild type sequence from which the glucosyltransferase enzyme is derived, or may be a heterologous sequence such as an epitope tag (at either N- or C-terminus) or a heterologous signal peptide (at N-terminus), for example. A glucosyltransferase enzyme herein typically lacks an N-terminal signal peptide.

A glucosyltransferase enzyme herein can be prepared by fermentation of an appropriately engineered microbial strain. Recombinant enzyme production by fermentation is well known in the art using microbial strains such as *E. coli, Bacillus* strains (e.g., *B. subtilis*), *Ralstonia eutropha, Pseudomonas fluorescens, Saccharomyces cerevisiae, Pichia pastoris, Hansenula polymorpha*, and species of *Aspergillus* (e.g., *A. awamori*) and *Trichoderma* (e.g., *T. reesei*) (e.g., see Adrio and Demain, *Biomolecules* 4:117-139, which is incorporated herein by reference). A nucleotide sequence encoding a glucosyltransferase enzyme amino acid sequence is typically linked to a heterologous promoter sequence to create an expression cassette for the enzyme. Such an expression cassette may be incorporated on a suitable plasmid or integrated into the microbial host chromosome, using methods well known in the art. The expression cassette may include a transcriptional terminator nucleotide sequence following the amino acid coding sequence. The expression cassette may also include, between the promoter sequence and amino acid coding sequence, a nucleotide sequence encoding a signal peptide that is designed to direct secretion of the glucosyltransferase enzyme. At the end of fermentation, cells may be ruptured accordingly and the glucosyltransferase enzyme can be isolated using methods such as precipitation, filtration, and/or concentration. Alternatively, a lysate comprising a glucosyltransferase can be used without further isolation. The activity of a glucosyltransferase enzyme can be confirmed by biochemical assay, such as measuring its conversion of sucrose to glucan polymer.

An activity of a glucosyltransferase enzyme herein is catalytic synthesis of a poly alpha-1,3-glucan (product) or poly alpha-1,3-1,6-glucan (product) in a reaction comprising sucrose (substrate). Such a glucan product can be as disclosed herein, for example. A glucosyltransferase enzyme in some aspects herein does not have, or has very little (less than 1%), dextransucrase, reuteransucrase, or alternansucrase activity.

A glucosyltransferase enzyme in certain embodiments does not occur in nature. For example, an enzyme herein is not believed to be one that is naturally secreted (i.e., mature form) from a microbe (from which the glucosyltransferase enzyme herein could possibly have been derived).

The temperature of a gtf reaction herein can be controlled, if desired. In certain embodiments, the temperature is between about 5° C. to about 50° C. The temperature in certain other embodiments is between about 20° C. to about 40° C. Alternatively, the temperature may be about 20, 21, 22, 23, 24, 25, 26, 27, 28, 29, 30, 31, 32, 33, 34, 35, 36, 37, 38, 39, or 40° C.

The initial concentration of sucrose in a gtf reaction solution herein can be about 20 g/L to about 400 g/L, for example. Alternatively, the initial concentration of sucrose can be about 75 g/L to about 175 g/L, or from about 50 g/L to about 150 g/L. Alternatively still, the initial concentration of sucrose can be about 40, 50, 60, 70, 80, 90, 100, 110, 120, 130, 140, 150, or 160 g/L (or any integer between 40 and 160 g/L), for example. "Initial concentration of sucrose" refers to the sucrose concentration in a gtf reaction just after all the reaction components have been added (at least water, sucrose, gtf enzyme).

Sucrose used in a glucosyltransferase reaction herein can be highly pure (≥99.5%) or be of any other purity or grade. For example, sucrose can have a purity of at least 99.0%, or can be reagent grade sucrose. As another example, incompletely refined sucrose can be used. Incompletely refined sucrose herein refers to sucrose that has not been processed to white refined sucrose. Thus, incompletely refined sucrose can be completely unrefined or partially refined. Examples of unrefined sucrose are "raw sucrose" ("raw sugar") and solutions thereof. Examples of partially refined sucrose have not gone through one, two, three, or more crystallization steps. The ICUMSA (International Commission for Uniform Methods of Sugar Analysis) of incompletely refined sucrose herein can be greater than 150, for example. Sucrose herein may be derived from any renewable sugar source such as sugar cane, sugar beets, cassava, sweet sorghum, or corn. Suitable forms of sucrose useful herein are crystalline form or non-crystalline form (e.g., syrup, cane juice, beet juice), for example. Additional suitable forms of incompletely refined sucrose are disclosed in U.S. Pat. Appl. Publ. No. 2015/0275256, which is incorporated herein by reference.

Methods of determining ICUMSA values for sucrose are well known in the art and disclosed by the International Commission for Uniform Methods of Sugar Analysis in *ICUMSA Methods of Sugar Analysis: Official and Tentative Methods Recommended by the International Commission for Uniform Methods of Sugar Analysis (ICUMSA)* (Ed. H. C. S. de Whalley, Elsevier Pub. Co., 1964), for example, which is incorporated herein by reference. ICUMSA can be measured, for example, by ICUMSA Method GS1/3-7 as described by R. J. McCowage, R. M. Urquhart and M. L. Burge (*Determination of the Solution Colour of Raw Sugars, Brown Sugars and Coloured Syrups at pH 7.0—Official*, Verlag Dr Albert Bartens, 2011 revision), which is incorporated herein by reference.

The pH of a gtf reaction solution in certain embodiments can be between about 4.0 to about 8.0. Alternatively, the pH can be about 4.0, 4.5, 5.0, 5.5, 6.0, 6.5, 7.0, 7.5, or 8.0. The pH can be adjusted or controlled by the addition or incorporation of a suitable buffer, including but not limited to: phosphate, tris, citrate, or a combination thereof. Buffer concentration in a gtf reaction solution can be from 0 mM to about 100 mM, or about 10, 20, or 50 mM, for example. A suitable amount of DTT (dithiothreitol, e.g., about 1.0 mM) can optionally be added to a reaction solution.

Examples of other conditions and components suitable for carrying out a glucosyltransferase reaction can be as disclosed in U.S. Patent Appl. Publ. No. 2014/0087431 (incorporated herein by reference), for producing poly alpha-1,3-glucan, or as disclosed in the below Examples, for producing poly alpha-1,3-1,6-glucan.

One or more different glucosyltransferase enzymes may be used in an enzymatic reaction to produce poly alpha-1,3-glucan or poly alpha-1,3-1,6-glucan polymer herein.

A poly alpha-1,3-glucan polymer as comprised in a composition herein can have, for example, at least 50% alpha-1,3 glucosidic linkages and a degree of polymerization of at least 100. In certain embodiments, a poly alpha-1,3-glucan has at least about 60%, 70%, 80%, 90%, 95%, 96%, 97%, 98%, 99%, or 100% (or any integer between 50% and 100%) glucosidic linkages that are alpha-1,3 linkages. Accordingly, poly alpha-1,3-glucan herein can have less than about 50%, 40%, 30%, 20%, 10%, 5%, 4%, 3%, 2%, 1%, or 0% (or any integer value between 0% and 50%) glucosidic linkages that are not alpha-1,3.

In some aspects, poly alpha-1,3-glucan polymer has no branch points or less than about 10%, 9%, 8%, 7%, 6%, 5%, 4%, 3%, 2%, or 1% branch points as a percent of the glucosidic linkages in the polymer. Examples of branch points include alpha-1,6 branch points, such as those that are present in mutan polymer.

Poly alpha-1,3-glucan in certain aspects herein can have a molecular weight in $DP_n$ or $DP_w$ of at least about 100. Alternatively, poly alpha-1,3-glucan herein can have a molecular weight in $DP_n$ or $DP_w$ of at least about 400. Alternatively still, poly alpha-1,3-glucan can have a molecular weight in $DP_n$ or $DP_w$ of at least about 100, 150, 200, 250, 300, 350, 400, 450, 500, 550, 600, 650, 700, 750, 800, 850, 900, 950, or 1000 (or any integer between 100 and 1000), for example.

Poly alpha-1,3-glucan herein is insoluble in water and other non-caustic aqueous liquids.

A poly alpha-1,3-1,6-glucan polymer as comprised in a composition herein can have, for example, (i) at least 30% alpha-1,3 glucosidic linkages, (ii) at least 30% alpha-1,6 glucosidic linkages, and (iii) a degree of polymerization of at least 1000, and wherein optionally the alpha-1,3 linkages and alpha-1,6 linkages do not consecutively alternate with each other.

At least 30% of the glucosidic linkages of poly alpha-1,3-1,6-glucan herein are alpha-1,3 linkages, and at least 30% of the glucosidic linkages are alpha-1,6 linkages, for example. Alternatively, the percentage of alpha-1,3 linkages can be at least 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, or 64%, for example. Alternatively still, the percentage of alpha-1,6 linkages can be at least 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, or 69%, for example.

Poly alpha-1,3-1,6-glucan herein can have any one of the aforementioned percentages of alpha-1,3 linkages and any one of the aforementioned percentages of alpha-1,6 linkages, just so long that the total of the percentages is not greater than 100%. For example, poly alpha-1,3-1,6-glucan can have (i) any one of 30%, 31%, 32%, 33%, 34%, 35%, 36%, 37%, 38%, 39%, or 40% (30%-40%) alpha-1,3 linkages and (ii) any one of 60%, 61%, 62%, 63%, 64%, 65%, 66%, 67%, 68%, or 69% (60%-69%) alpha-1,6 linkages, just so long that the total of the percentages is not greater than 100%. Non-limiting examples include poly alpha-1,3-1,6-glucan with 31% alpha-1,3 linkages and 67% alpha-1,6 linkages. Other examples of alpha-1,3 and alpha-1,6 linkage profiles are provided in Table 2. In certain embodiments, at least 60% of the glucosidic linkages of poly alpha-1,3-1,6-glucan herein are alpha-1,6 linkages.

Poly alpha-1,3-1,6-glucan in some aspects herein can have, for example, less than 10%, 9%, 8%, 7%, 6%, 5%, 4%, 3%, 2%, or 1% of glucosidic linkages other than alpha-1,3 and alpha-1,6. In another embodiment, poly alpha-1,3-1,6-glucan only has alpha-1,3 and alpha-1,6 linkages.

The backbone of a poly alpha-1,3-1,6-glucan herein can be linear/unbranched, for example. Alternatively, there can be branches in the poly alpha-1,3-1,6-glucan. A poly alpha-1,3-1,6-glucan in certain embodiments can thus have no branch points or less than about 30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3%, 2%, or 1% branch points as a percent of the glucosidic linkages in the polymer.

For the following discussion, consider that . . . G-1,3-G-1,6-G-1,3-G-1,6-G-1,3-G- . . . (where G represents glucose) represents a stretch of glucose monomeric units linked by consecutively alternating alpha-1,3 linkages and alpha-1,6 linkages. Poly alpha-1,3-1,6-glucan in some aspects herein comprises alpha-1,3 linkages and alpha-1,6 linkages that do not consecutively alternate with each other. Alternatively, poly alpha-1,3-1,6-glucan herein can comprise, for example, less than 2, 3, 4, 5, 6, 7, 8, 9, 10, or more glucose monomeric units that are linked consecutively with alternating alpha-1,3 and alpha-1,6 linkages.

Poly alpha-1,3-1,6-glucan in some aspects herein can have a $DP_w$ of at least about 1000. For example, the $DP_w$ of poly alpha-1,3-1,6-glucan can be at least about 10000. Alternatively, the $DP_w$ can be at least about 1000 to about 15000. Alternatively still, the $DP_w$ can be at least about 1000, 2000, 3000, 4000, 5000, 6000, 7000, 8000, 9000, 10000, 11000, 12000, 13000, 14000, or 15000 (or any integer between 1000 and 15000), for example.

In certain embodiments, poly alpha-1,3-1,6-glucan can have an $M_w$ of at least about 50000, 100000, 200000, 300000, 400000, 500000, 600000, 700000, 800000, 900000, 1000000, 1100000, 1200000, 1300000, 1400000, 1500000, or 1600000 (or any integer between 50000 and 1600000), for example. Poly alpha-1,3-1,6-glucan can alternatively have an $M_w$ of at least about 4000, 5000, 10000, 20000, 30000, or 40000, for example.

Poly alpha-1,3-1,6-glucan herein is insoluble in water and other non-caustic aqueous liquids.

In some aspects, a poly alpha-1,3-glucan or poly alpha-1,3-1,6-glucan polymer as produced by a glucosyltransferase enzymatic reaction is freeze-dried after its synthesis in the reaction. This freeze-drying represents the first time the polymer is dried. Such freeze-dried polymer can be comprised in a composition herein that absorbs aqueous liquid. It is believed that such freeze-dried poly alpha-1,3-glucan or poly alpha-1,3-1,6-glucan polymer retains the structure of the polymer as it existed, respectively, before being freeze-dried.

Freeze-dried poly alpha-1,3-glucan or poly alpha-1,3-1,6-glucan polymer herein can be prepared by freeze-drying a polymer wet cake isolated from a glucosyltransferase enzymatic reaction. Suitable conditions that can be employed for wet cake production and freeze-drying a wet cake are disclosed elsewhere herein.

Freeze-dried poly alpha-1,3-glucan or poly alpha-1,3-1,6-glucan polymer herein typically comprises less than about 3, 2, 1, 0.5, or 0.1 wt % water.

A poly alpha-1,3-glucan or poly alpha-1,3-1,6-glucan polymer as produced by a glucosyltransferase enzymatic reaction in some aspects herein is not completely dried after its synthesis in the reaction. Such never-dried polymer can be comprised in a composition herein that absorbs aqueous liquid. It is believed that such polymer has a structure that is the same as, or similar with, the structure of polymer herein that is freeze-dried after enzymatic synthesis. By never being "completely dried", it is meant that the polymer never has less than about 65, 64, 63, 62, 61, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, or 3 wt % water.

A composition comprising poly alpha-1,3-glucan or poly alpha-1,3-1,6-glucan polymer as presently disclosed can comprise about, or at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 99, 99.5, or 99.9 wt %, for example, of one or a combination of both polymers. Regarding some embodiments, such wt %'s can depend, in part, on the wt % of water associated with the polymer, if such has never been dried since its enzymatic synthesis. Dry compositions (e.g., freeze-dried glucan herein) in certain aspects can be in the form of powder, granules, microcapsules, flakes, or any other form of particulate matter. Other examples include larger compositions such as pellets, bars, kernels, beads, tablets, sticks, or other agglomerates. A dry composition herein typically has less than 3, 2, 1, 0.5, or 0.1 wt % water comprised therein. Poly alpha-1,3-glucan or poly alpha-1,3-1,6-glucan polymer as comprised in a composition of the present disclosure is not chemically cross-linked.

A composition comprising poly alpha-1,3-glucan or poly alpha-1,3-1,6-glucan polymer as presently disclosed can be in the form of, or comprised within, a personal care product, household product, medical product, or industrial product, for example. In this context, compositions in certain embodiments can be used as absorbent or superabsorbent materials. Examples of such materials include those that are hypoallergenic. A superabsorbent material herein has an absorption capacity with respect to an aqueous liquid herein of at least 15 g aqueous liquid/g glucan polymer, for example. A personal care product, household product, medical product, or industrial product in some embodiments can comprise an absorbent or superabsorbent material as presently disclosed. One particular advantage of a composition herein is that it is biodegradable and hence environmentally friendly.

Examples of personal care products and/or uses herein include absorbent personal hygiene products such as baby diapers, potty training pants, incontinence products (e.g., pads, adult diapers), and feminine hygiene products (e.g., sanitary napkins, tampons, interlabial products, panty liners).

Examples of industrial products and/or uses herein include telecommunication cable wrappings; food pads; agricultural and forestry applications such as for retaining water in soil and/or to release water to plant roots; firefighting devices; and cleanup of acidic or basic aqueous solutions spills.

Examples of medical products and/or uses herein include wound healing dressings such as bandages and surgical pads; phantoms for ultrasound-based imaging; hospital bed sheets; sanitary towels; controlled drug release devices; cell immobilization islets; three-dimensional cell culture substrates; bioactive scaffolds for regenerative medicine; stomach bulking devices; and disposal of controlled drugs.

Personal care products, household products, and/or medical products in some embodiments herein can absorb a bodily fluid such as urine, blood, blood serum, liquid fecal matter (e.g., diarrhea), bile, stomach acid/juice, vomit, amniotic fluid, breast milk, cerebrospinal fluid, exudate, lymph, mucus (e.g., nasal drainage, phlegm), peritoneal fluid, pleural fluid, pus, rheum, saliva, sputum, synovial fluid, sweat, and/or tears.

One particular advantage of a composition herein is that it is biodegradable and hence environmentally friendly.

Embodiments of the present disclosure also concern a method for preparing a polymer selected from the group consisting of poly alpha-1,3-glucan and poly alpha-1,3-1,6-glucan. This method comprises:

(a) contacting at least water, sucrose, and a glucosyltransferase enzyme, whereby poly alpha-1,3-glucan polymer or poly alpha-1,3-1,6-glucan polymer is produced;

(b) washing the polymer produced in step (a) to prepare a wet cake comprising polymer and residual water; and (c) removing the residual water from the wet cake such that the structure of the polymer is not substantially changed;

wherein the polymer resulting from step (c) comprises an open-cell pore structure with an average pore size of about 100 nm to about 3000 nm in diameter, and wherein the polymer can absorb aqueous liquid. Significantly, poly alpha-1,3-glucan and poly alpha-1,3-1,6-glucan polymers produced in this manner have an enhanced ability to absorb aqueous liquids, even though the polymers have not been subject to any chemical processing (e.g., cross-linking), which is typically used to enhance the absorption capability of polysaccharides and other polymer materials. Also of significance, polymers produced as above exhibit an ability to absorb saline solutions at about the same level of absorption of deionized water. In contrast, other types of materials that have shown an ability to absorb deionized water typically exhibit low saline solution absorption ability.

The contacting step in a method of preparing poly alpha-1,3-glucan or poly alpha-1,3-1,6-glucan polymer can comprise providing a glucosyltransferase enzymatic reaction as disclosed elsewhere herein (e.g., comprising any gtf enzyme and/or reaction conditions [e.g., time, temperature, pH, buffer concentration] disclosed herein). It would be understood that, as the glucosyltransferase enzyme synthesizes poly alpha-1,3-glucan or poly alpha-1,3-1,6-glucan, the reaction typically becomes a reaction mixture given that insoluble poly alpha-1,3-glucan or poly alpha-1,3-1,6-glucan falls out of solution. Contacting can be performed in any number of ways. For example, a desired amount of sucrose can first be dissolved in water (optionally, other components may also be added at this stage of preparation, such as buffer components), followed by addition of a glucosyltransferase. The solution may be kept still, or agitated via stirring or orbital shaking, for example. The reaction does not depend on the presence of any microbial cells.

Completion of a gtf reaction in certain embodiments can be determined visually (e.g., no more accumulation of poly alpha-1,3-glucan or poly alpha-1,3-1,6-glucan) and/or by measuring the amount of sucrose left in the reaction solution (residual sucrose), where a percent sucrose consumption of over about 90% can indicate reaction completion. Typically, a reaction of the disclosed process can take about 12, 18, 24, 30, 36, 48, 60, 72, 84, or 96 hours to complete. Reaction time may depend, for example, on certain parameters such as the amount of sucrose and glucosyltransferase enzyme used in the reaction.

A gtf enzymatic reaction at or near its completion can include, in addition to poly alpha-1,3-glucan or poly alpha-1,3-1,6-glucan product, various components such as residual sucrose, one or more gtf enzymes, glucose, fructose, leucrose, buffer, FermaSure®, soluble oligosaccharides, oligosaccharide primers, bacterial enzyme extract components, borates, sodium hydroxide, hydrochloric acid, cell lysate, proteins and/or nucleic acids. Minimally, the components of a gtf enzymatic reaction at or near completion can include, in addition to poly alpha-1,3-glucan or poly alpha-1,3-1,6-glucan product, sucrose, one or more gtf enzymes, glucose and fructose, for example. In another example, the components of a gtf enzymatic reaction can include, in addition to poly alpha-1,3-glucan or poly alpha-1,3-1,6-glucan, sucrose, one or more gtf enzymes, glucose, fructose, and soluble oligosaccharides such as leucrose (and optionally bacterial enzyme extract components).

The linkage profile and/or molecular weight of poly alpha-1,3-glucan or poly alpha-1,3-1,6-glucan produced in a gtf reaction herein can be any of those disclosed elsewhere herein, for example.

Regarding washing step (b) of a glucan preparation method herein, poly alpha-1,3-glucan or poly alpha-1,3-1,6-glucan product from a glucan production method is subjected to a washing process that renders a wet cake of the glucan product. Such washing can entail, for example, first separating insoluble poly alpha-1,3-glucan or poly alpha-1,3-1,6-glucan from the reaction contents by centrifugation or filtration; thus, a method herein typically comprises a separating step such as a filtering and/or centrifuging step. For example, glucan product (can manifest as a slurry in a reaction), can be collected on a funnel using a mesh screen over filter paper. Filtered glucan can be resuspended in water (e.g., deionized water) and filtered one or more times to remove soluble components such as sucrose, fructose and leucrose. As another example of washing, glucan product can be collected as a pellet via centrifugation, resuspended in water (e.g., deionized water), and re-pelleted and resuspended one or more additional times. Thus, glucan separation from a reaction (isolation) can comprise washing one, two, or more times with water, for example. A wash with water can use at least one-half reaction volume of water in two displacement washes (e.g., wash with at least one 1 L of water if the reaction volume was 2 L), for example. After washing with water (using filtering or centrifugation, for example), glucan polymer product can be subjected to (another) filtration step to render a wet cake comprising residual water and poly alpha-1,3-glucan or poly alpha-1,3-1,6-glucan. Residual water is water that remains in glucan polymer product after subjecting it to a filtration procedure, since filtering removes bulk excess water, but not all water from insoluble glucan product.

A wet cake is termed as "wet" given the retention of water (residual water) by the washed poly alpha-1,3-glucan or poly alpha-1,3-1,6-glucan. A glucan wet cake herein can comprise about 65, 64, 63, 62, 61, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, or 3 wt % water, for example. In other examples, a glucan wet cake herein can comprise about 10-60, 10-50, 10-40, 10-30, 10-20, 20-60, 20-50, 20-40, 20-30, 30-60, 30-50, 30-40, 40-60, 40-50, or 50-60 wt % water.

Filtering herein, such as for washing, can be performed by any means known in the art. For example, filtering can be done using gravity-, vacuum-, press-, or centrifugal-filtration. Filtering to produce a wet cake is typically performed using filtration in which a force (e.g., pressure) is applied (e.g., vacuum-, press-, or centrifugal-filtration). A filtration apparatus can employ any filtering components (e.g., filter paper, mesh screen) suitable for separating insoluble glucan product (solids) from liquids. Pressure that can be applied during a filtration step herein can be about 20-200, 20-150, 20-100, 20-80, 20-60, 20-40, 40-200, 40-150, 40-100, 40-80, 40-60, 60-200, 60-150, 60-100, or 60-80 psi or psig, for example.

All in all, poly alpha-1,3-glucan or poly alpha-1,3-1,6-glucan that is separated, washed and rendered as a wet cake as above is substantially isolated from an enzymatic reaction from which the glucan polymer was produced. Thus, for example, poly alpha-1,3-glucan or poly alpha-1,3-1,6-glucan is separated from at least fructose, glucose monomer, residual sucrose, and certain byproducts (e.g., leucrose, soluble oligosaccharides) present in an enzymatic reaction.

A method in certain embodiments for preparing poly alpha-1,3-glucan or poly alpha-1,3-1,6-glucan polymer comprises step (c) of removing residual water from glucan wet cake such that the structure of the polymer is not substantially changed/altered. For example, residual water is removed in a manner that substantially preserves the nano- and/or micro-structure (structure as observed on a nanometer or micrometer scale, respectively) of the polymer as it exists before removal of residual water therefrom. Substantial preservation of polymer structure in some embodiments can be with respect to average pore size. For example, the average pore diameter of polymer from which residual water has been removed can be within (plus or minus) at least about 15%, 14%, 13%, 12%, 11%, 10%, 9%, 8%, 7%, 6%, 5%, 4%, 3%, 2%, or 1% of the average pore diameter of the polymer as it had existed in wet cake before residual water removal. Average pore diameter can be measured as disclosed herein. In certain aspects, the WRV of polymer from which residual water has been removed can be within (plus or minus) at least about 15%, 14%, 13%, 12%, 11%, 10%, 9%, 8%, 7%, 6%, 5%, 4%, 3%, 2%, or 1% of the WRV of the polymer as it had existed in wet cake before residual water removal. WRV can be measured as disclosed herein, and can be with respect to any aqueous liquid as presently disclosed.

Removal of residual water (step c) can be performed in certain embodiments by freeze-drying the wet cake produced after washing poly alpha-1,3-glucan or poly alpha-1,3-1,6-glucan polymer produced in a glucosyltransferase reaction. Freeze-drying (lyophilization) can be performed following the procedure listed in the disclosed Examples, for instance. In some aspects, the freezing step in a lyophilization herein can be performed at a temperature of about −80° C., −70° C., −60° C., −50° C., −40° C., −30° C., −50 to −30° C., or about −45 to −35° C., and for a time of about 30-120, 30-90, or 30-60 minutes (e.g., ~60 minutes). A vacuum can be applied during the freezing, or after the freezing step, and can be held for about 15-60, 15-45, or 15-30 minutes (e.g., ~30 minutes), for example. A vacuum can be applied such that the pressure is less than about 400, 300, 200, 100, or 50 mTorr; pressure can be at about 150-250, 175-225, or about 200 mTorr in some cases. A vacuum can be applied over a 30-60 minute ramp/time period, for example. The primary drying phase of a lyophilization herein can be performed at a temperature of about −15 to −5° C. (e.g., about −10° C.), and for a time of about 24-96, 24-72, 24-48, 36-48, 40-50, 45, or 46 hours, for example. Primary drying is typically conducted under a vacuum as disclosed herein. Freeze-dried poly alpha-1,3-glucan or poly alpha-1,3-1,6-glucan polymer herein typically comprises less than about 3, 2, 1, 0.5, or 0.1 wt % water.

Removal of residual water (step c) in certain embodiments herein, such as when the polymer is poly alpha-1,3-glucan, does not comprise drying polymer at a temperature of at least about 60° C. (e.g., 60-100° C., 65° C.).

Poly alpha-1,3-glucan or poly alpha-1,3-1,6-glucan polymer resulting after removing residual water (step c) comprises an open-cell pore structure with an average pore size of about 100 nm to about 3000 nm in diameter, and wherein the polymer can absorb aqueous liquid. Any of the features disclosed elsewhere herein can characterize such a polymer, for example, such as features regarding pore structure (e.g., average pore diameter, pore diameter uniformity, open-cell composition, continuity of pores, closed-cell composition) and aqueous liquid absorption capacity (e.g., WRV, type of aqueous liquid that can be absorbed, capacity to absorb aqueous solution to similar extent as water).

In some embodiments—particularly those regarding poly alpha-1,3-glucan herein—the absorption capacity of glucan polymer resulting after removing residual water (step c) (e.g., performed by freeze-drying) is substantially higher compared to the absorption capacity of glucan polymer that is dried by means that do not preserve polymer structure (e.g., high temperature drying such as oven drying). For example, the absorption capacity (e.g., measured using WRV) of glucan polymer (e.g., poly alpha-1,3-glucan) dried in a manner preserving structure can be at least 2-fold, 3-fold, 4-fold, 5-fold, 6-fold, 7-fold, 8-fold, 9-fold, or 10-fold higher than the absorption capacity of otherwise same glucan polymer but that was dried by means not preserving polymer structure.

Embodiments of the present disclosure also concern a method for preparing poly alpha-1,3-1,6-glucan. This method comprises:
(a) contacting at least water, sucrose, and a glucosyltransferase enzyme that synthesizes poly alpha-1,3-1,6-glucan, whereby poly alpha-1,3-1,6-glucan is produced;
(b) washing the poly alpha-1,3-1,6-glucan produced in step (a) to prepare a wet cake comprising poly alpha-1,3-1,6-glucan and residual water; and
(c) removing the residual water from the wet cake;

wherein the poly alpha-1,3-1,6-glucan resulting from step (c) can absorb aqueous liquid. Significantly, poly alpha-1,3-1,6-glucan polymer produced in this manner has an enhanced ability to absorb aqueous liquids, even though the polymers have not been subject to any chemical processing (e.g., cross-linking), which is typically used to enhance the absorption capability of polysaccharides and other polymer materials. Also of significance, polymers produced as above exhibit an ability to absorb saline solutions at about the same level of absorption of deionized water. In contrast, other types of materials that have shown an ability to absorb deionized water typically exhibit low saline solution absorption ability.

The contacting step in a method of preparing poly alpha-1,3-1,6-glucan polymer can be as disclosed above, for example, regarding performing a gtf reaction. A glucosyltransferase enzyme in certain embodiments for producing poly alpha-1,3-1,6-glucan in step (a) can comprise, or consist of, an amino acid sequence that is at least 90%, 91%, 92%, 93%, 94%, 95%, 96%, 97%, 98%, or 99% identical to, SEQ ID NO:2, SEQ ID NO:4, SEQ ID NO:6, SEQ ID NO:8, or SEQ ID NO:10, wherein the glucosyltransferase enzyme has activity. Alternatively, a glucosyltransferase enzyme can comprise, or consist of, SEQ ID NO:2, SEQ ID NO:4, SEQ ID NO:6, SEQ ID NO:8, or SEQ ID NO:10.

The linkage profile and/or molecular weight of poly alpha-1,3-1,6-glucan produced in a gtf reaction herein can be any of those disclosed elsewhere herein, for example.

Washing step (b) in a method for preparing poly alpha-1,3-1,6-glucan, including wet cake preparation, can be as disclosed above with respect to washing poly alpha-1,3-glucan.

A method in certain embodiments for preparing poly alpha-1,3-1,6-glucan polymer comprises step (c) of removing residual water from glucan wet cake. Any of the features described above with regard to removing residual water from glucan wet cake such that the structure of the polymer is not substantially altered can likewise apply (e.g., freeze-drying).

In some embodiments, removing residual water from poly alpha-1,3-1,6-glucan wet cake (step c) can comprise drying polymer at a temperature of at least about 60° C. (e.g., 60-100° C., 65° C.). Such drying can be carried out for a time period of about 6, 12, 18, 24, 30, 36, 6-12, 6-18, 6-24, 12-18, or 12-24 hours, for example. Residual water can be removed by oven drying, for example.

Poly alpha-1,3-1,6-glucan polymer from which residual water has been removed typically comprises less than about 3, 2, 1, 0.5, or 0.1 wt % water.

Non-limiting examples of compositions and methods disclosed herein include:
1. A composition comprising a polymer selected from the group consisting of poly alpha-1,3-glucan and poly alpha-1,3-1,6-glucan, wherein the polymer comprises an open-cell pore structure with an average pore size of about 100 nm to about 3000 nm in diameter, and wherein the polymer can absorb aqueous liquid.
2. The composition of embodiment 1, wherein the polymer is a product of an enzymatic reaction comprising water, sucrose and a glucosyltransferase enzyme.
3. The composition of embodiment 2, and wherein the polymer is not completely dried after its production in the reaction.
4. The composition of embodiment 2, wherein the polymer is freeze-dried after its production in the reaction, and wherein the freeze-drying is the first time the polymer has been dried.
5. The composition of embodiment 4, wherein the polymer is poly alpha-1,3-glucan.
6. The composition of any one of embodiments 1-5, wherein the polymer has a water retention value (WRV) of at least about 150.
7. The composition of any one of embodiments 1-6, wherein the poly alpha-1,3-glucan has at least 50% alpha-1,3 glucosidic linkages and a degree of polymerization of at least 100.
8. The composition of any one of embodiments 1-4, 6, or 7, wherein the poly alpha-1,3-1,6-glucan has (i) at least 30% alpha-1,3 glucosidic linkages, (ii) at least 30% alpha-1,6 glucosidic linkages, and (iii) a degree of polymerization of at least 1000, and wherein optionally the alpha-1,3 linkages and alpha-1,6 linkages do not consecutively alternate with each other.

9. The composition of any one of embodiments 1-8, wherein the composition is a personal care product, household product, medical product, or industrial product.

10. A method for preparing a polymer selected from the group consisting of poly alpha-1,3-glucan and poly alpha-1,3-1,6-glucan, wherein the method comprises:
   (a) contacting at least water, sucrose, and a glucosyltransferase enzyme that synthesizes poly alpha-1,3-glucan or poly alpha-1,3-1,6-glucan polymer, whereby poly alpha-1,3-glucan or poly alpha-1,3-1,6-glucan polymer is produced;
   (b) washing the polymer produced in step (a) to prepare a wet cake comprising polymer and residual water; and
   (c) removing the residual water from the wet cake such that the structure of the polymer is not substantially changed;
   wherein the polymer resulting from step (c) comprises an open-cell pore structure with an average pore size of about 100 nm to about 3000 nm in diameter, and wherein the polymer can absorb aqueous liquid.

11. The method of embodiment 10, wherein step (c) is performed by freeze-drying the wet cake.

12. The method of embodiment 11, wherein the polymer is poly alpha-1,3-glucan.

13. A method for preparing poly alpha-1,3-1,6-glucan, wherein the method comprises:
   (a) contacting at least water, sucrose, and a glucosyltransferase enzyme that synthesizes poly alpha-1,3-1,6-glucan, whereby poly alpha-1,3-1,6-glucan is produced;
   (b) washing the poly alpha-1,3-1,6-glucan produced in step (a) to prepare a wet cake comprising poly alpha-1,3-1,6-glucan and residual water; and
   (c) removing the residual water from the wet cake;
   wherein the poly alpha-1,3-1,6-glucan resulting from step (c) can absorb aqueous liquid.

14. The method of embodiment 13, wherein the glucosyltransferase enzyme comprises an amino acid sequence that is at least 90% identical to SEQ ID NO:2, SEQ ID NO:4, SEQ ID NO:6, SEQ ID NO:8, or SEQ ID NO:10.

15. The method of embodiment 13 or 14, wherein step (c) is performed by oven drying.

EXAMPLES

The present disclosure is further exemplified in the following Examples. It should be understood that these Examples, while indicating certain preferred aspects herein, are given by way of illustration only. From the above discussion and these Examples, one skilled in the art can ascertain the essential characteristics of the disclosed embodiments, and without departing from the spirit and scope thereof, can make various changes and modifications to adapt the disclosed embodiments to various uses and conditions.

Abbreviations

The meanings of some of the abbreviations used herein are as follows: "g" means gram(s), "h" means hour(s), "mL" means milliliter(s), "psi" means pound(s) per square inch, "wt %" means weight percentage, "µm" means micrometer(s), "° C." means degrees Celsius, "mg" means milligram(s), "mm" means millimeter(s), "µL" means microliter(s), "mmol" means millimole(s), "min" means minute(s), "mol %" means mole percent, "M" means molar, "mM" means millimolar, "N" means normal, "rpm" means revolutions per minute, "w/v" means weight for volume, "MPa" means megaPascal(s), "LB means Luria broth, "nm means nanometer(s), "OD" means optical density, "IPTG" means isopropyl-beta-D-thio-galactoside, "xg" means gravitational force, "SDS-PAGE" means sodium dodecyl sulfate polyacrylamide electrophoresis, "DTT" means dithiothreitol, "BCA" means bicinchoninic acid, "DMAc" means N,N'-dimethyl acetamide, "DMSO" means dimethylsulfoxide, "NMR" means nuclear magnetic resonance, "SEC" means size exclusion chromatography, "DI water" means deionized water.

Materials

T10 dextran (D9260), IPTG, (cat#I6758), triphenyltetrazolium chloride, and BCA protein assay kit/reagents were obtained from the Sigma Co. (St. Louis, Mo.). BELLCO spin flasks were from the Bellco Co. (Vineland, N.J.). LB medium was from Becton, Dickinson and Company (Franklin Lakes, N.J.). Suppressor 7153 antifoam was obtained from Cognis Corporation (Cincinnati, Ohio). All other chemicals were obtained from commonly used suppliers of such chemicals.

Seed Medium

The seed medium used to grow starter cultures for the fermenters contained: yeast extract (AMBEREX 695, 5.0 grams per liter, g/L), $K_2HPO_4$ (10.0 g/L), $KH_2PO_4$ (7.0 g/L), sodium citrate dihydrate (1.0 g/L), $(NH_4)_2SO_4$ (4.0 g/L), $MgSO_4$ heptahydrate (1.0 g/L) and ferric ammonium citrate (0.10 g/L). The pH of the medium was adjusted to 6.8 using either 5N NaOH or $H_2SO_4$ and the medium was sterilized in the flask. Post-sterilization additions included glucose (20 mL/L of a 50% w/w solution) and ampicillin (4 mL/L of a 25 mg/mL stock solution).

Fermenter Medium

The growth medium used in the fermenter contained: $KH_2PO_4$ (3.50 g/L), $FeSO_4$ heptahydrate (0.05 g/L), $MgSO_4$ heptahydrate (2.0 g/L), sodium citrate dihydrate (1.90 g/L), yeast extract (AMBEREX 695, 5.0 g/L), Suppressor 7153 antifoam (0.25 mL/L), NaCl (1.0 g/L), $CaCl_2$ dihydrate (10 g/L), and NIT trace elements solution (10 mL/L). The NIT trace elements solution contained citric acid monohydrate (10 g/L), $MnSO_4$ hydrate (2 g/L), NaCl (2 g/L), $FeSO_4$ heptahydrate (0.5 g/L), $ZnSO_4$ heptahydrate (0.2 g/L), $CuSO_4$ pentahydrate (0.02 g/L) and $NaMoO_4$ dihydrate (0.02 g/L). Post-sterilization additions included glucose (12.5 g/L of a 50% w/w solution) and ampicillin (4 mL/L of a 25 mg/mL stock solution).

General Methods

Production of Recombinant Glucosyltransferase (Gtf) Enzymes in Fermentation

Production of a recombinant gtf enzyme in a fermenter was initiated by preparing a pre-seed culture of an E. coli strain expressing the gtf enzyme. A 10-mL aliquot of seed medium was added into a 125-mL disposable baffled flask and inoculated with a 1.0-mL aliquot of the E. coli strain in 20% glycerol. The culture was allowed to grow at 37° C. while shaking at 300 rpm for 3 hours.

A seed culture, which was used for starting growth for gtf fermentation, was prepared by charging a 2-L shake flask with 0.5 L of seed medium. 1.0 mL of the pre-seed culture was aseptically transferred into 0.5-L seed medium in the flask and cultivated at 37° C. and 300 rpm for 5 hours. The seed culture was transferred at an optical density 550 nm ($OD_{550}$)>2 to a 14-L fermenter (Braun, Perth Amboy, N.J.) containing 8 L of fermenter medium at 37° C.

The E. coli strain was allowed to grow in the fermenter medium. Glucose (50% w/w glucose solution containing 1% w/w $MgSO_4 \cdot 7H_2O$) was fed to this culture when its glucose concentration decreased to 0.5 g/L. The glucose feed was started at 0.36 grams feed per minute (g feed/min) and increased progressively each hour to 0.42, 0.49, 0.57, 0.66, 0.77, 0.90, 1.04, 1.21, 1.41 1.63, 1.92, and 2.2 g feed/min, respectively. The feed rate remained constant afterwards. Glucose concentration in the medium was monitored using an YSI glucose analyzer (YSI, Yellow Springs, Ohio). When glucose concentration exceeded 0.1 g/L, the feed rate was decreased or stopped temporarily. Induction of gtf enzyme expression, which was performed when cells reached an $OD_{550}$ of 70, was initiated by adding 9 mL of 0.5 M IPTG. The dissolved oxygen (DO) concentration was controlled at 25% of air saturation. The DO was controlled first by impeller agitation rate (400 to 1200 rpm) and later by aeration rate (2 to 10 standard liters per minute, slpm). Culture pH was controlled at 6.8 using $NH_4OH$ (14.5% w/v) and $H_2SO_4$ (20% w/v). Back pressure was maintained at 0.5 bars. At various intervals (20, 25 and 30 hours), 5 mL of Suppressor 7153 antifoam was added to the fermenter to suppress foaming. Cells were harvested by centrifugation 8 hours post IPTG addition and were stored at −80° C. as a cell paste.

The cell paste obtained from fermentation for each gtf enzyme was suspended at 150 g/L in 50 mM potassium phosphate buffer, pH 7.2, to prepare a slurry. The slurry was homogenized at 12,000 psi (Rannie-type machine, APV-1000 or APV 16.56) and the homogenate chilled to 4° C. With moderately vigorous stirring, 50 g of a floc solution (Sigma Aldrich no. 409138, 5% in 50 mM sodium phosphate buffer, pH 7.0) was added per liter of cell homogenate. Agitation was reduced to light stirring for 15 minutes. The cell homogenate was then clarified by centrifugation at 4500 rpm for 3 hours at 5-10° C. Supernatant, containing gtf enzyme, was concentrated (approximately 5×) with a 30 kiloDalton (kDa) cut-off membrane to render a gtf extract.

Determination of Gtf Enzymatic Activity

Gtf enzyme activity was confirmed by measuring the production of reducing sugars (fructose and glucose) in a gtf reaction solution. A reaction solution was prepared by adding a gtf extract (prepared as above) to a mixture containing sucrose (50 g/L), potassium phosphate buffer (pH 6.5, 50 mM), and dextran T10 (1 mg/mL); the gtf extract was added to 5% by volume. The reaction solution was then incubated at 22-25° C. for 24-30 hours, after which it was centrifuged. Supernatant (0.01 mL) was added to a mixture containing 1 N NaOH and 0.1% triphenyltetrazolium chloride (Sigma-Aldrich). The mixture was incubated for five minutes after which its $OD_{480nm}$ was determined using an ULTROSPEC spectrophotometer (Pharmacia LKB, New York, N.Y.) to gauge the presence of the reducing sugars fructose and glucose.

Determination of Glycosidic Linkages

Glycosidic linkages in glucan products synthesized by a gtf enzyme were determined by $^{13}C$ NMR (nuclear magnetic resonance) or $^1H$ NMR.

For $^{13}C$ NMR, dry glucan polymer (25-30 mg) was dissolved in 1 mL of deuterated DMSO containing 3% by weight of LiCl with stirring at 50° C. Using a glass pipet, 0.8 mL of the solution was transferred into a 5-mm NMR tube. A quantitative $^{13}C$ NMR spectrum was acquired using a Bruker Avance 500-MHz NMR spectrometer (Billerica, Mass.) equipped with a CPDUL cryoprobe at a spectral frequency of 125.76 MHz, using a spectral window of 26041.7 Hz. An inverse-gated decoupling pulse sequence using waltz decoupling was used with an acquisition time of 0.629 second, an inter-pulse delay of 5 seconds, and 6000 pulses. The time domain data was transformed using an exponential multiplication of 2.0 Hz.

For $^1H$ NMR, approximately 20 mg of a glucan polymer sample was weighed into a vial on an analytical balance. The vial was removed from the balance and 0.8 mL of deuterated DMSO (DMSO-d6), containing 3% by weight of LiCl, was added to the vial. The mixture was stirred with a magnetic stir bar and warmed to 90° C. until the glucan sample dissolved. The solution was allowed to cool to room temperature. While stirring at room temperature, 0.2 mL of a 20% by volume solution of trifluoroacetic acid (TFA) in DMSO-d6 was added to the polymer solution. The TFA was added in order to move all hydroxyl proton signals out of the region of the spectrum where carbohydrate ring proton signals occur. A portion, 0.8 mL, of the final solution was transferred, using a glass pipet, into a 5-mm NMR tube. A quantitative $^1H$ NMR spectrum was acquired using an NMR spectrometer with a proton frequency of 500 MHz or greater. The spectrum was acquired using a spectral window of 11.0 ppm and a transmitter offset of 5.5 ppm. A 90° pulse was applied for 32 pulses with an inter-pulse delay of 10 seconds and an acquisition time of 1.5 seconds. The time domain data were transformed using an exponential multiplication of 0.15 Hz.

Determination of Weight Average Degree of Polymerization ($DP_w$)

The $DP_w$ of a glucan product synthesized by a gtf enzyme was determined by SEC. Dry glucan polymer was dissolved in DMAc and 5% LiCl (0.5 mg/mL) with shaking overnight at 100° C. The SEC system used was an Alliance™ 2695 separation module from Waters Corporation (Milford, Mass.) coupled with three on-line detectors: a differential refractometer 2410 from Waters, a multiangle light scattering photometer Heleos™ 8+ from Wyatt Technologies (Santa Barbara, Calif.), and a differential capillary viscometer ViscoStar™ from Wyatt. The columns used for SEC were four styrene-divinyl benzene columns from Shodex (Japan) and two linear KD-806M, KD-802 and KD-801 columns to improve resolution at the low molecular weight region of a polymer distribution. The mobile phase was DMAc with 0.11% LiCl. The chromatographic conditions used were 50° C. in the column and detector compartments, 40° C. in the sample and injector compartment, a flow rate of 0.5 mL/min, and an injection volume of 100 μL. The software packages used for data reduction were Empower™ version 3 from Waters (calibration with broad glucan polymer standard) and Astra® version 6 from Wyatt (triple detection method with column calibration).

Example 1

Production of Gtf Enzyme 4297 (SEQ ID NO:2)

This Example describes preparing an N-terminally truncated version of a *Streptococcus oralis* gtf enzyme identified in GENBANK under GI number 7684297 (SEQ ID NO:2, encoded by SEQ ID NO:1; herein referred to as "4297").

A nucleotide sequence encoding gtf 4297 was synthesized using codons optimized for protein expression in *E. coli* (DNA2.0, Inc., Menlo Park, Calif.). The nucleic acid product (SEQ ID NO:1), encoding gtf 4297 (SEQ ID NO:2), was subcloned into pJexpress404® (DNA2.0, Inc.) to generate the plasmid construct identified as pMP70. This plasmid construct was used to transform *E. coli* MG1655 (ATCC™ 47076) cells to generate the strain identified as MG1655/pMP70.

Production of gtf 4297 by bacterial expression and determination of its enzymatic activity were performed following the procedures disclosed in the General Methods section. The linkage profile and $DP_w$ of glucan produced by 4297 are shown in Table 2 (see Example 6 below).

Example 2

Production of Gtf Enzyme 3298 (SEQ ID NO:4)

This Example describes preparing an N-terminally truncated version of a *Streptococcus* sp. C150 gtf enzyme identified in GENBANK under GI number 322373298 (SEQ ID NO:4, encoded by SEQ ID NO:3; herein referred to as "3298").

A nucleotide sequence encoding gtf 3298 was synthesized using codons optimized for protein expression in *E. coli* (DNA2.0, Inc.). The nucleic acid product (SEQ ID NO:3), encoding gtf 3298 (SEQ ID NO:4), was subcloned into pJexpress404® to generate the plasmid construct identified as pMP98. This plasmid construct was used to transform *E. coli* MG1655 (ATCC™ 47076) cells to generate the strain identified as MG1655/pMP98.

Production of gtf 3298 by bacterial expression and determination of its enzymatic activity were performed following the procedures disclosed in the General Methods section. The linkage profile and DP, of glucan produced by 3298 are shown in Table 2 (see Example 6 below).

Example 3

Production of Gtf Enzyme 0544 (SEQ ID NO:6)

This Example describes preparing an N-terminally truncated version of a *Streptococcus mutans* gtf enzyme identified in GENBANK under GI number 290580544 (SEQ ID NO:6, encoded by SEQ ID NO:5; herein referred to as "0544").

A nucleotide sequence encoding gtf 0544 was synthesized using codons optimized for protein expression in *E. coli* (DNA2.0, Inc.). The nucleic acid product (SEQ ID NO:5), encoding gtf 0544 (SEQ ID NO:6), was subcloned into pJexpress404® to generate the plasmid construct identified as pMP67. This plasmid construct was used to transform *E. coli* MG1655 (ATCC™ 47076) cells to generate the strain identified as MG1655/pMP67.

Production of gtf 0544 by bacterial expression and determination of its enzymatic activity were performed following the procedures disclosed in the General Methods section. The linkage profile and DP, of glucan produced by 0544 are shown in Table 2 (see Example 6 below).

Example 4

Production of Gtf Enzyme 5618 (SEQ ID NO:8)

This Example describes preparing an N-terminally truncated version of a *Streptococcus sanguinis* gtf enzyme identified in GENBANK under GI number 328945618 (SEQ ID NO:8, encoded by SEQ ID NO:7; herein referred to as "5618").

A nucleotide sequence encoding gtf 5618 was synthesized using codons optimized for protein expression in *E. coli* (DNA2.0, Inc.). The nucleic acid product (SEQ ID NO:7), encoding gtf 5618 (SEQ ID NO:8), was subcloned into pJexpress404® to generate the plasmid construct identified as pMP72. This plasmid construct was used to transform *E. coli* MG1655 (ATCC™ 47076) cells to generate the strain identified as MG1655/pMP72.

Production of gtf 5618 by bacterial expression and determination of its enzymatic activity were performed following the procedures disclosed in the General Methods section. The linkage profile and DP, of glucan produced by 5618 are shown in Table 2 (see Example 6 below).

Example 5

Production of Gtf Enzyme 2379 (SEQ ID NO:10)

This Example describes preparing an N-terminally truncated version of a *Streptococcus salivarius* gtf enzyme identified in GENBANK under GI number 662379 (SEQ ID NO:10, encoded by SEQ ID NO:9; herein referred to as "2379").

A nucleotide sequence encoding gtf 2379 was synthesized using codons optimized for protein expression in *E. coli* (DNA2.0, Inc.). The nucleic acid product (SEQ ID NO:9), encoding gtf 2379 (SEQ ID NO:10), was subcloned into pJexpress404® to generate the plasmid construct identified as pMP65. This plasmid construct was used to transform *E. coli* MG1655 (ATCC™ 47076) cells to generate the strain identified as MG1655/pMP65.

Production of gtf 2379 by bacterial expression and determination of its enzymatic activity were performed following the procedures disclosed in the General Methods section. The linkage profile and $DP_w$ of glucan produced by 2379 are shown in Table 2 (see Example 6 below).

Example 6

Production of Insoluble Glucan Polymer with Gtf Enzymes

This Example describes using the gtf enzymes prepared in the above Examples to synthesize glucan polymer.

Reactions were performed with each of the above gtf enzymes following the procedures disclosed in the General Methods section. Briefly, gtf reaction solutions were prepared comprising sucrose (50 g/L), potassium phosphate buffer (pH 6.5, 50 mM) and a gtf enzyme (2.5% extract by volume). After 24-30 hours at 22-25° C., insoluble glucan polymer product was harvested by centrifugation, washed three times with water, washed once with ethanol, and dried at 50° C. for 24-30 hours.

Following the procedures disclosed in the General Methods section, the glycosidic linkages in the insoluble glucan polymer product from each reaction were determined by $^{13}C$ NMR, and the $DP_w$ for each product was determined by SEC. The results of these analyses are shown in Table 2.

TABLE 2

Linkages and $DP_w$ of Poly Alpha-1,3-1,6-Glucan Produced by Various Gtf Enzymes

| Gtf | SEQ ID NO. | Glucan Alpha Linkages | | $DP_w$ |
|---|---|---|---|---|
| | | % 1,3 | % 1,6 | |
| 4297 | 2 | 31 | 67 | 10540 |
| 3298 | 4 | 50 | 50 | 1235 |
| 0544 | 6 | 62 | 36 | 3815 |
| 5618 | 8 | 34 | 66 | 3810 |
| 2379 | 10 | 37 | 63 | 1640 |

Thus, gtf enzymes capable of producing insoluble glucan polymer having a heterogeneous glycosidic linkage profile (alpha-1,3 and 1,6 linkages) and a $DP_w$ of at least 1000 were identified. These enzymes can be used to produce insoluble poly alpha-1,3-1,6-glucan suitable for preparing compositions that can absorb aqueous liquid, as demonstrated below in Example 7.

Example 7

Preparation of Glucan Polymer Compositions that can Absorb Aqueous Liquid

This Example describes preparation of compositions comprising glucan polymers with enhanced aqueous liquid absorption capability. Specifically, compositions comprising poly alpha-1,3-glucan or poly alpha-1,3-1,6-glucan prepared following various techniques were highly water-absorbent.

Poly alpha-1,3-glucan polymer was synthesized, and wet cake thereof was prepared, following the procedures disclosed in U.S. Appl. Publ. No. 2014/0179913 (see Example 12 therein, for example), which is incorporated herein by reference.

Poly alpha-1,3-1,6-glucan was synthesized following the enzymatic reaction procedure employed in Example 6 above. The poly alpha-1,3-1,6-glucan solids produced in the reaction were collected using a Buchner funnel fitted with a mesh screen over filter paper. The filtered poly alpha-1,3-1,6-glucan solids were resuspended in deionized water and filtered twice more as above to remove sucrose, fructose and other low molecular weight, soluble by-products. The resulting material was characterized as a wet cake.

Wet cakes of each glucan polymer were then subjected to either standard drying in an oven (overnight drying at 65° C.), or freeze-drying. Freeze-drying of wet cake was performed using a VirTis ADVANTAGE PLUS freeze dryer/lyophilizer, as follows. A shelf tray was used to place each sample in the instrument. Freezing was conducted at −40° C. for 1 hour, after which a vacuum was applied at 200 mTorr with a 30-minute ramp. Primary drying was then conducted at −10° C. for 45.5 hours.

The water retention values (WRV) of the oven-dried and freeze-dried poly alpha-1,3-glucan or poly alpha-1,3-1,6-glucan materials provided above were then measured. Specifically, for each sample, dried polymer (1 g) was immersed in 20 mL of deionized (DI) water, or water containing 1 wt % NaCl, and left to equilibrate for 2 hours. The solid material (appeared as slurry) was then transferred into a 50-mL FALCON tube containing a 0.45-micron PVDF filter insert on the top half of the tube. The Falcon tube was then centrifuged at 4500 rpm for 20 minutes in an EPPENDORF 5804 centrifuge with fixed rotor. The filter insert allowed removal/separation of bulk excess liquid from the wet material during centrifugation. The mass of the wet material was then measured on a balance, after which it was dried overnight in an oven at 60° C. The dry mass was then measured. WRV for each polymer/treatment was calculated using the following formula: ((mass of wet polymer−mass of dry polymer)/mass of dry polymer)*100. WRVs are listed in FIG. 1. WRV was also measured for an isolated poly alpha-1,3 glucan wet cake sample that had not been subjected to a first oven or freeze-drying step.

It was found that poly alpha-1,3-glucan that had been freeze-dried (FIG. 1, column 5) or that had never been dried (FIG. 1, column 6) had about a four-fold higher WRV compared to the WRV of poly alpha-1,3-glucan that had been oven-dried (FIG. 1, columns 1 and 2). Scanning electron micrograph (SEM) images of freeze-dried and oven-dried poly alpha-1,3-glucan (FIG. 2) indicate that the freeze-dried material has open-cell pore structure, whereas oven-dried material appears to have a closed structure. The increased WRV of freeze-dried poly alpha-1,3-glucan polymer is likely caused by physical entrapment of water via capillary forces in the porous structure. Notably, the WRVs of both freeze-dried and never-dried poly alpha-1,3-glucan were nearly the same. Hence, it is expected that any process (e.g., freeze-drying) capable of maintaining the open-cell structure present in originally synthesized, never dried poly alpha-1,3-glucan would be suitable at preparing polymer compositions with high water absorption capacity.

It was found that poly alpha-1,3-1,6-glucan that had been oven-dried exhibited high WRV (FIG. 1, columns 3 and 4). This WRV increased as the alpha-1,6 glucosidic linkage content increased: poly alpha-1,3-1,6-glucan with 70% alpha-1,6 linkages (FIG. 1, column 4) had higher WRV compared to poly alpha-1,3-1,6-glucan having 50% alpha-1,6 linkages (FIG. 1, column 3). It is important to note that all the polymers tested in FIG. 1, including the poly alpha-1,3-1,6-glucan polymers, were water-insoluble; this is in contrast to dextran polymers, which have a high alpha-1,6 glucosidic linkage content.

WRV measurements were generally unaffected by water salinity, as WRV measurements for the tested polymers were similar for both water-only and 1 wt % NaCl aqueous solution treatments. This result is notable, since other types of materials that have shown an ability to absorb deionized water typically exhibit low saline absorption ability.

Thus, compositions comprising poly alpha-1,3-glucan or poly alpha-1,3-1,6-glucan prepared following various techniques are able to absorb aqueous liquid. Such absorbency indicates that these compositions are likely suitable for use in various personal care items whose performance is based, in part, on aqueous liquid absorption (e.g., diapers, certain feminine hygiene products). In addition, it is notable that the enhanced WRV of these materials was achieved without the need of chemical modifications (e.g., cross-linking), which could otherwise render material less suitable for certain personal care applications (e.g., chemical processing can leave impurities that have been linked to skin inflammation).

What is claimed is:

1. A composition comprising a polymer that is poly alpha-1,3-glucan having at least 90% alpha-1,3 glucosidic linkages and a degree of polymerization of at least 100, wherein the polymer comprises an open-cell pore structure, wherein the polymer has not been chemically modified, wherein the polymer can absorb aqueous liquid, and wherein the composition is a personal care product, household product, medical product, or industrial product that absorbs aqueous liquid.

2. The composition of claim 1, wherein the polymer is an insoluble product of an enzymatic reaction comprising water, sucrose and a glucosyltransferase enzyme.

3. The composition of claim 2, and wherein the polymer is not completely dried after its production in said reaction.

4. The composition of claim 2, wherein the polymer is freeze-dried after its production in said reaction, and wherein said freeze-drying is the first time the polymer is dried.

5. The composition of claim 2, wherein residual water is removed from the polymer after its production in said reaction, wherein the residual water is removed in a manner that substantially preserves the nano-structure and/or micro-structure of the polymer as it existed before removal of residual water.

6. The composition of claim 1, wherein the poly alpha-1,3-glucan has at least 95% alpha-1,3 glucosidic linkages.

7. The composition of claim 6, wherein the poly alpha-1,3-glucan has at least 99% alpha-1,3 glucosidic linkages.

8. The composition of claim 5, wherein removal of the residual water does not comprise drying the polymer at a temperature of at least about 60° C.

9. The composition of claim 5, wherein removal of the residual water does not comprise oven drying the polymer.

10. The composition of claim 1, wherein the polymer has a water retention value (WRV) of at least about 150.

11. The composition of claim 1, wherein the composition is said personal care product.

12. The composition of claim 11, wherein the personal care product is a diaper, pad, or feminine hygiene product.

13. The composition of claim 1, wherein the composition is said medical product.

14. The composition of claim 13, wherein the medical product is a wound healing dressing.

15. The composition of claim 14, wherein the wound healing dressing is a bandage or surgical pad.

16. The composition of claim 1, wherein the composition is said industrial product.

17. The composition of claim 16, wherein the industrial product is selected from the group consisting of (i) telecommunication cable wrapping, (ii) food pad, (iii) fire-fighting device, (iv) product for cleanup of acidic or basic aqueous solutions spills, and (v) agricultural or forestry product for retaining water in soil and/or to release water to plant roots.

18. An absorption method that comprises contacting a composition according to claim 1 with an aqueous liquid-comprising composition, wherein the composition absorbs aqueous liquid from said liquid-comprising composition.

19. The absorption method of claim 18, wherein the aqueous liquid-comprising composition comprises urine, blood, blood serum, liquid fecal matter, bile, stomach acid/juice, vomit, amniotic fluid, breast milk, cerebrospinal fluid, exudate, lymph, mucus, peritoneal fluid, pleural fluid, pus, rheum, saliva, sputum, synovial fluid, sweat, or tears.

20. The absorption method of claim 19, wherein the aqueous liquid-comprising composition comprises urine or blood.

* * * * *

SEQUENCE LISTING

```
<160> NUMBER OF SEQ ID NOS: 10

<210> SEQ ID NO 1
<211> LENGTH: 4047
<212> TYPE: DNA
<213> ORGANISM: Streptococcus oralis

<400> SEQUENCE: 1
```

```
atgatcgacg gcaaaaacta ctacgtacag gatgatggca cggtaaagaa gaatttcgcg     60
gtagaactga atggtcgtat cctgtatttt gatgcagaaa ccggcgctct ggttgatagc    120
aacgagtatc agttccaaca gggtacgagc agcctgaaca atgaattttc tcagaagaac    180
gcattctatg gtacgaccga taaggatatt gagactgtgg atggctacct gaccgcagat    240
agctggtatc gcccgaaatt catcctgaag gatggcaaga cgtggaccgc gagcacggaa    300
acggatctgc gtccgctgtt gatggcatgg tggccggaca gcgtacccca aatcaactat    360
ctgaactaca tgaaccagca gggtctgggt gcgggtgcgt ttgagaacaa agtggagcag    420
gccctgctga cgggtgcaag ccaacaggta caacgcaaga tcgaagagaa gattggtaaa    480
gagggtgata ccaagtggct gcgcacccctg atgggtgcgt tcgtgaaaac gcaaccaaac    540
tggaatatca aaaccgagtc tgaaacgacc ggcacgaaaa aggaccatct gcaaggcggt    600
gcactgctgt atacgaacaa cgagaaatcc ccgcacgcgg acagcaaatt tcgtctgctg    660
aatcgtaccc cgaccagcca aaccggcacg ccgaagtatt tcatcgacaa gtctaacggt    720
ggctacgaat ttctgctggc gaacgatttt gacaatagca atcctgcggt acaagctgag    780
cagctgaatt ggctgcacta catgatgaac tttggcagca ttgttgcgaa tgatccgacc    840
gcgaatttcg acggcgttcg tgtggatgct gttgataacg tcaatgcgga cttgttgcaa    900
attgcaagcg attactttaa gagccgttac aaagtcggtg agagcgaaga agaagcgatc    960
aagcacctgt ccatcctgga agcatggagc gataacgacc cggactacaa caaagatacc   1020
aagggtgcac agttggcgat tgataacaaa ctgcgcctga gcctgctgta ctctttcatg   1080
cgtaatctga gcatccgtag cggtgttgaa ccgacgatta ccaatagcct gaatgaccgt   1140
tccagcgaaa agaagaacgg cgagcgtatg gcaaattaca tcttcgtgcg tgcccacgat   1200
agcgaggtcc aaacggtgat cgccgacatc attcgcgaaa acatcaatcc gaacaccgac   1260
ggcctgacgt ttacgatgga cgagctgaag caggcattca agatttacaa cgaggacatg   1320
cgcaaggcgg acaaaaagta cccagtttt aacattccta ccgcacacgc gctgatgctg   1380
tctaataagg attctattac ccgcgtgtac tatggtgatc tgtatactga cgatggtcag   1440
tacatggaga agaaaagccc gtatcacgat gcgattgacg ctctgctgcg tgcacgtatt   1500
aaatacgtcg cgggtggcca ggatatgaaa gtgacctata tgggcgtgcc gcgtgaagcg   1560
gataagtgga gctataacgg cattctgacc agcgtgcgct atggcacggg cgctaacgaa   1620
gccacggatg agggcactgc ggaaacgcgc acgcaaggta tggcagtgat tgcgagcaat   1680
aatccaaatc tgaaactgaa tgaatgggac aagttgcaag tcaacatggg tgcggcgcat   1740
aagaatcaat attaccgtcc ggttctgctg accactaagg acggtatcag ccgttatctg   1800
accgatgaag aagtgcctca gagcctgtgg aaaaagacgg acgcaaacgg tattctgacc   1860
ttcgacatga atgatattgc tggctacagc aacgtgcaag ttagcggtta cctggccgtc   1920 tgggtcccg tcggtgcgaa ggcggatcaa gatgcgcgca cgaccgcatc caagaagaaa   1980
aatgcgtcgg gtcaggtgta cgaaagcagc gcggctctgg atagccagct gatttacgaa   2040
ggtttcagca actttcaaga ctttgccact cgcgatgatc agtacacgaa caaggtcatt   2100
gcgaaaaacg tgaatctgtt caagaatggg ggtgtgacca gcttcgagct gccgccgcag   2160
tacgtgagca gccaagatgg cacctttctg gacagcatta tccaaaacgg ctatgcattt   2220
gaagaccgtt acgatatggc ggatgagcaag aataacaagt atggtagcct gaaagacctg   2280
ttgaacgcgc tgcgcgcact gcacagcgtc aacattcaag caatcgccga ttgggtgccg   2340
```

```
gaccaaattt acaacttgcc gggcaaagag gtggtgaccg caactcgtgt caacaactac    2400
ggcacctacc gtgagggtgc tgaaatcaaa gaaaagctgt atgtcgccaa tagcaagacc    2460
aacgaaaccg atttccaagg taaatacggt ggtgcgttcc tggatgagct gaaggcgaag    2520
tacccggaga ttttcgagcg tgtccaaatc agcaacggcc aaaagatgac taccgatgaa    2580
aagatcacca atggagcgcg aaatactttt aatggcacca atattctggg tcgtggcgcg    2640
tactatgtcc tgaaagattg ggccagcaat gattacctga cgaaccgtaa cggcgagatt    2700
gttttgccga agcaactggt taacaagaat agctataccg gctttgtcag cgacgcgaac    2760
ggcacgaagt tctattctac ctctggctac caggcgaaga acagcttcat tcaagacgaa    2820
aacggtaatt ggtattactt tgacaaacgt ggttatctgg ttacgggcgc acacgagatt    2880
gatggcaagc atgtctactt cctgaaaaac ggtatccaac tgcgtgacag catccgtgag    2940
gatgagaacg gtaatcaata ctattacgac cagaccggcg cacaagtgct gaaccgttac    3000
tacacgacgg acggtcagaa ttggcgctat ttcgatgcga aggtgttat ggcacgcggc    3060 ctggtaaaga ttggtgacgg ccaacagttt ttcgatgaaa acggttacca ggtcaagggc    3120
aagattgtta gcgcaaaaga cggcaagctg cgctactttg ataaagactc tggcaatgct    3180
gtcattaatc gtttcgcgca gggtgacaat ccgagcgact ggtactattt cggtgtggaa    3240
tttgctaaac tgacgggttt gcaaaagatc ggccagcaga cgctgtattt tgaccaagac    3300
ggtaagcaag tcaaaggtaa gatcgtaact ctgtcgacaa aaagcattcg ttacttcgat    3360
gccaacagcg gtgaaatggc ggttggcaag ttcgcggaag gtgcaaagaa tgagtggtat    3420
tatttcgata aaaccggcaa agcggttact ggtttgcaga aaattggtaa gcagaccctg    3480
tactttgacc aggacggtaa acaggttaaa ggcaaggttg tcacgctggc tgataaaagc    3540
atccgctact tcgacgcaga ctccggcgag atggcggtcg gtaagtttgc agagggtgcg    3600
aagaacgagt ggtactattt tgatcagact ggcaaggccg tgactggttt gcaaaagatt    3660
gacaagcaaa ccttgtactt cgaccaggac ggtaaacaag tcaagggtaa gattgtgacg    3720
ttgagcgaca agtcgatccg ttactttgat gctaatagcg gtgagatggc tactaacaaa    3780
ttcgtcgagg gctcgcagaa tgaatggtac tacttcgatc aagcgggtaa ggctgttacg    3840
ggcttgcaac aggtcggtca gcaaactctg tacttcaccc aggatggtaa gcaagtgaag    3900
ggtaaggtcg tggacgtgaa cggtgtttct cgttatttcg acgcaaactc cggtgacatg    3960
gctcgttcta aatggattca actggaagat ggcagctgga tgtatttcga ccgtgacggt    4020
cgtggccaga attttggccg taactaa                                       4047
```

<210> SEQ ID NO 2
<211> LENGTH: 1348
<212> TYPE: PRT
<213> ORGANISM: Streptococcus oralis

<400> SEQUENCE: 2

Met Ile Asp Gly Lys Asn Tyr Tyr Val Gln Asp Gly Thr Val Lys
1               5                   10                  15

Lys Asn Phe Ala Val Glu Leu Asn Gly Arg Ile Leu Tyr Phe Asp Ala
            20                  25                  30

Glu Thr Gly Ala Leu Val Asp Ser Asn Glu Tyr Gln Phe Gln Gln Gly
        35                  40                  45

Thr Ser Ser Leu Asn Asn Glu Phe Ser Gln Lys Asn Ala Phe Tyr Gly
    50                  55                  60

Thr Thr Asp Lys Asp Ile Glu Thr Val Asp Gly Tyr Leu Thr Ala Asp

```
                65                  70                  75                  80
        Ser Trp Tyr Arg Pro Lys Phe Ile Leu Lys Asp Gly Lys Thr Trp Thr
                            85                  90                  95
        Ala Ser Thr Glu Thr Asp Leu Arg Pro Leu Met Ala Trp Trp Pro
                    100                 105                 110
        Asp Lys Arg Thr Gln Ile Asn Tyr Leu Asn Tyr Met Asn Gln Gln Gly
                        115                 120                 125
        Leu Gly Ala Gly Ala Phe Glu Asn Lys Val Glu Gln Ala Leu Leu Thr
                    130                 135                 140
        Gly Ala Ser Gln Gln Val Gln Arg Lys Ile Glu Glu Lys Ile Gly Lys
        145                 150                 155                 160
        Glu Gly Asp Thr Lys Trp Leu Arg Thr Leu Met Gly Ala Phe Val Lys
                            165                 170                 175
        Thr Gln Pro Asn Trp Asn Ile Lys Thr Glu Ser Glu Thr Thr Gly Thr
                    180                 185                 190
        Lys Lys Asp His Leu Gln Gly Gly Ala Leu Leu Tyr Thr Asn Asn Glu
                        195                 200                 205
        Lys Ser Pro His Ala Asp Ser Lys Phe Arg Leu Leu Asn Arg Thr Pro
                    210                 215                 220
        Thr Ser Gln Thr Gly Thr Pro Lys Tyr Phe Ile Asp Lys Ser Asn Gly
        225                 230                 235                 240
        Gly Tyr Glu Phe Leu Leu Ala Asn Asp Phe Asp Asn Ser Asn Pro Ala
                            245                 250                 255
        Val Gln Ala Glu Gln Leu Asn Trp Leu His Tyr Met Met Asn Phe Gly
                        260                 265                 270
        Ser Ile Val Ala Asn Asp Pro Thr Ala Asn Phe Asp Gly Val Arg Val
                    275                 280                 285
        Asp Ala Val Asp Asn Val Asn Ala Asp Leu Leu Gln Ile Ala Ser Asp
                    290                 295                 300
        Tyr Phe Lys Ser Arg Tyr Lys Val Gly Glu Ser Glu Glu Ala Ile
        305                 310                 315                 320
        Lys His Leu Ser Ile Leu Glu Ala Trp Ser Asp Asn Asp Pro Asp Tyr
                            325                 330                 335
        Asn Lys Asp Thr Lys Gly Ala Gln Leu Ala Ile Asp Asn Lys Leu Arg
                    340                 345                 350
        Leu Ser Leu Leu Tyr Ser Phe Met Arg Asn Leu Ser Ile Arg Ser Gly
                        355                 360                 365
        Val Glu Pro Thr Ile Thr Asn Ser Leu Asn Asp Arg Ser Ser Glu Lys
                    370                 375                 380
        Lys Asn Gly Glu Arg Met Ala Asn Tyr Ile Phe Val Arg Ala His Asp
        385                 390                 395                 400
        Ser Glu Val Gln Thr Val Ile Ala Asp Ile Arg Glu Asn Ile Asn
                            405                 410                 415
        Pro Asn Thr Asp Gly Leu Thr Phe Thr Met Asp Glu Leu Lys Gln Ala
                    420                 425                 430
        Phe Lys Ile Tyr Asn Glu Asp Met Arg Lys Ala Asp Lys Lys Tyr Thr
                        435                 440                 445
        Gln Phe Asn Ile Pro Thr Ala His Ala Leu Met Leu Ser Asn Lys Asp
                    450                 455                 460
        Ser Ile Thr Arg Val Tyr Tyr Gly Asp Leu Tyr Thr Asp Asp Gly Gln
        465                 470                 475                 480
        Tyr Met Glu Lys Lys Ser Pro Tyr His Asp Ala Ile Asp Ala Leu Leu
                            485                 490                 495
```

```
Arg Ala Arg Ile Lys Tyr Val Ala Gly Gly Gln Asp Met Lys Val Thr
            500                 505                 510

Tyr Met Gly Val Pro Arg Glu Ala Asp Lys Trp Ser Tyr Asn Gly Ile
            515                 520                 525

Leu Thr Ser Val Arg Tyr Gly Thr Gly Ala Asn Glu Ala Thr Asp Glu
            530                 535                 540

Gly Thr Ala Glu Thr Arg Thr Gln Gly Met Ala Val Ile Ala Ser Asn
545                 550                 555                 560

Asn Pro Asn Leu Lys Leu Asn Glu Trp Asp Lys Leu Gln Val Asn Met
                565                 570                 575

Gly Ala Ala His Lys Asn Gln Tyr Tyr Arg Pro Val Leu Leu Thr Thr
            580                 585                 590

Lys Asp Gly Ile Ser Arg Tyr Leu Thr Asp Glu Glu Val Pro Gln Ser
            595                 600                 605

Leu Trp Lys Lys Thr Asp Ala Asn Gly Ile Leu Thr Phe Asp Met Asn
            610                 615                 620

Asp Ile Ala Gly Tyr Ser Asn Val Gln Val Ser Gly Tyr Leu Ala Val
625                 630                 635                 640

Trp Val Pro Val Gly Ala Lys Ala Asp Gln Asp Ala Arg Thr Thr Ala
            645                 650                 655

Ser Lys Lys Lys Asn Ala Ser Gly Gln Val Tyr Glu Ser Ser Ala Ala
            660                 665                 670

Leu Asp Ser Gln Leu Ile Tyr Glu Gly Phe Ser Asn Phe Gln Asp Phe
            675                 680                 685

Ala Thr Arg Asp Asp Gln Tyr Thr Asn Lys Val Ile Ala Lys Asn Val
            690                 695                 700

Asn Leu Phe Lys Glu Trp Gly Val Thr Ser Phe Glu Leu Pro Pro Gln
705                 710                 715                 720

Tyr Val Ser Ser Gln Asp Gly Thr Phe Leu Asp Ser Ile Ile Gln Asn
            725                 730                 735

Gly Tyr Ala Phe Glu Asp Arg Tyr Asp Met Ala Met Ser Lys Asn Asn
            740                 745                 750

Lys Tyr Gly Ser Leu Lys Asp Leu Leu Asn Ala Leu Arg Ala Leu His
            755                 760                 765

Ser Val Asn Ile Gln Ala Ile Ala Asp Trp Val Pro Asp Gln Ile Tyr
            770                 775                 780

Asn Leu Pro Gly Lys Glu Val Thr Ala Thr Arg Val Asn Asn Tyr
785                 790                 795                 800

Gly Thr Tyr Arg Glu Gly Ala Glu Ile Lys Glu Lys Leu Tyr Val Ala
            805                 810                 815

Asn Ser Lys Thr Asn Glu Thr Asp Phe Gln Gly Lys Tyr Gly Gly Ala
            820                 825                 830

Phe Leu Asp Glu Leu Lys Ala Lys Tyr Pro Glu Ile Phe Glu Arg Val
            835                 840                 845

Gln Ile Ser Asn Gly Gln Lys Met Thr Thr Asp Glu Lys Ile Thr Lys
            850                 855                 860

Trp Ser Ala Lys Tyr Phe Asn Gly Thr Asn Ile Leu Gly Arg Gly Ala
865                 870                 875                 880

Tyr Tyr Val Leu Lys Asp Trp Ala Ser Asn Asp Tyr Leu Thr Asn Arg
            885                 890                 895

Asn Gly Glu Ile Val Leu Pro Lys Gln Leu Val Asn Lys Asn Ser Tyr
            900                 905                 910
```

```
Thr Gly Phe Val Ser Asp Ala Asn Gly Thr Lys Phe Tyr Ser Thr Ser
            915                 920                 925

Gly Tyr Gln Ala Lys Asn Ser Phe Ile Gln Asp Glu Asn Gly Asn Trp
        930                 935                 940

Tyr Tyr Phe Asp Lys Arg Gly Tyr Leu Val Thr Gly Ala His Glu Ile
945                 950                 955                 960

Asp Gly Lys His Val Tyr Phe Leu Lys Asn Gly Ile Gln Leu Arg Asp
                965                 970                 975

Ser Ile Arg Glu Asp Glu Asn Gly Asn Gln Tyr Tyr Asp Gln Thr
            980                 985                 990

Gly Ala Gln Val Leu Asn Arg Tyr Tyr Thr Thr Asp Gly Gln Asn Trp
        995                 1000                1005

Arg Tyr Phe Asp Ala Lys Gly Val Met Ala Arg Gly Leu Val Lys
    1010                1015                1020

Ile Gly Asp Gly Gln Gln Phe Phe Asp Glu Asn Gly Tyr Gln Val
    1025                1030                1035

Lys Gly Lys Ile Val Ser Ala Lys Asp Gly Lys Leu Arg Tyr Phe
    1040                1045                1050

Asp Lys Asp Ser Gly Asn Ala Val Ile Asn Arg Phe Ala Gln Gly
    1055                1060                1065

Asp Asn Pro Ser Asp Trp Tyr Tyr Phe Gly Val Glu Phe Ala Lys
    1070                1075                1080

Leu Thr Gly Leu Gln Lys Ile Gly Gln Thr Leu Tyr Phe Asp
    1085                1090                1095

Gln Asp Gly Lys Gln Val Lys Gly Lys Ile Val Thr Leu Ser Asp
    1100                1105                1110

Lys Ser Ile Arg Tyr Phe Asp Ala Asn Ser Gly Glu Met Ala Val
    1115                1120                1125

Gly Lys Phe Ala Glu Gly Ala Lys Asn Glu Trp Tyr Tyr Phe Asp
    1130                1135                1140

Lys Thr Gly Lys Ala Val Thr Gly Leu Gln Lys Ile Gly Lys Gln
    1145                1150                1155

Thr Leu Tyr Phe Asp Gln Asp Gly Lys Gln Val Lys Gly Lys Val
    1160                1165                1170

Val Thr Leu Ala Asp Lys Ser Ile Arg Tyr Phe Asp Ala Asp Ser
    1175                1180                1185

Gly Glu Met Ala Val Gly Lys Phe Ala Glu Gly Ala Lys Asn Glu
    1190                1195                1200

Trp Tyr Tyr Phe Asp Gln Thr Gly Lys Ala Val Thr Gly Leu Gln
    1205                1210                1215

Lys Ile Asp Lys Gln Thr Leu Tyr Phe Asp Gln Asp Gly Lys Gln
    1220                1225                1230

Val Lys Gly Lys Ile Val Thr Leu Ser Asp Lys Ser Ile Arg Tyr
    1235                1240                1245

Phe Asp Ala Asn Ser Gly Glu Met Ala Thr Asn Lys Phe Val Glu
    1250                1255                1260

Gly Ser Gln Asn Glu Trp Tyr Tyr Phe Asp Gln Ala Gly Lys Ala
    1265                1270                1275

Val Thr Gly Leu Gln Gln Val Gly Gln Gln Thr Leu Tyr Phe Thr
    1280                1285                1290

Gln Asp Gly Lys Gln Val Lys Gly Lys Val Val Asp Val Asn Gly
    1295                1300                1305

Val Ser Arg Tyr Phe Asp Ala Asn Ser Gly Asp Met Ala Arg Ser
```

-continued

|  | 1310 |  |  | 1315 |  |  |  | 1320 |  |  |  |
| --- | --- | --- | --- | --- | --- | --- | --- | --- | --- | --- | --- |
| Lys | Trp | Ile | Gln | Leu | Glu | Asp | Gly | Ser | Trp | Met | Tyr | Phe | Asp | Arg |
|  |  |  | 1325 |  |  |  | 1330 |  |  |  | 1335 |

Asp Gly Arg Gly Gln Asn Phe Gly Arg Asn
        1340            1345

<210> SEQ ID NO 3
<211> LENGTH: 3729
<212> TYPE: DNA
<213> ORGANISM: Streptococcus sp. C150

<400> SEQUENCE: 3

| atgattaacg gtaaagagta ttatgtcgaa gatgacggca cggtccgtaa gaattacgtt | 60 |
| --- | --- |
| ttggaacgta acggcggcag ccaatacttc aatgcagaga ctggtgaact cagcaatcag | 120 |
| aaagattatc gcttcgataa gaacggcggc accggtagcg cggcagatag caccactaat | 180 |
| accaatgtta ccgtgaatgg tgataagaac gcgttttacg gtaccacgga gaaagacatc | 240 |
| gagttggtgg acggttactt cactgcgaac acttggtatc gcccgaaaga aattctgaaa | 300 |
| gacggcaagg aatggacggc gagcaccgag aatgataagc gtccgttgct gacggtttgg | 360 |
| tggccaagca aggcaatcca ggcgagctat ctgaactata gcgtgagga gggtctgggt | 420 |
| accaaccaaa ccttcacgag ctacagcagc caaacgcaaa tggatcaggc agccttagag | 480 |
| gttcaaaaac gtatcgaaga acgcattgca cgcgagggta taccgattg ctgcgtacc | 540 |
| accatcaaga acttcgttaa aacgcagccg ggttggaaca gcacctcaga gaatctggac | 600 |
| aactctgacc atctgcaggg tggcgccctg ctgtataaca atagcaaccg cacgtcctac | 660 |
| gcgaactctg actatcgctt gctgaatcgt acccctaccc aacaagatgg cacgcgtcgc | 720 |
| tacttcaagg acaattcttc tggcggtttc gagttttgc tggcgaatga catcgataac | 780 |
| agcaacccgg cagtgcaggc agaacaactg aattggctgc actacattat gaatattggc | 840 |
| agcctgacgg tggtagcga agatgagaat ttcgacggtg ttcgtgttga tgctgtggac | 900 |
| aacgttaatg cggacttgct gcaaatcgca tccgactact ttaaagcaaa atacggcgtg | 960 |
| gagaaaagcg aagaagaagc gattaagcat ctgtccatct tagaggcgtg gagccacaac | 1020 |
| gatgcgtatt acaatgaaga tactaagggc gcacagctgc cgatggatga tccgctgcgc | 1080 |
| ttggcgatgt ttttagctt tctgcgtccg attggtaatc gtagcggcct ggagccgttg | 1140 |
| atcacgaact cgctgaacga ccgtagcgag agcaaaaaga taccaagcg catggcgaac | 1200 |
| tataccttcg tgcgtgctca tgactctgag gtccagagcg ttatcggtca gattatcaag | 1260 |
| aacgaaatca atcctcagag cacgggtaac acgttcacgt tggatgaaat gaaaaaggct | 1320 |
| tttaagatct ataacgcgga catgcgcagc gcgaataaac gttacaccca atacaacatt | 1380 |
| ccgagcgcgt acgcttttat gctgaccaac aaggataccg ttccgcgtgt gtattatggt | 1440 |
| gacctgtaca cggacgatgg tcaatacatg gcacagaaat caccgtacca cgatgccatc | 1500 |
| agcaccctgc tgcaagcccg tattcgttac gctgctggcg ccaagatat gaagatgagc | 1560 |
| tatgtgggca gcggtaatac taacggctgg gacgcgtccg gtgtcctgac cagcgttcgc | 1620 |
| tatggtaaag gtcgaacaa tgcgagcgac gcaggcaccg ccgaaacccg caatcaaggc | 1680 |
| atggccgtga ttctgagcaa ccagccggca ctgcgtctga atagcaatct gaccatcaac | 1740 |
| atgggtgccg cgcatcgtaa tcaagcatat cgcccactgc tgctgaccac gagcaatggc | 1800 |
| gtggcgagct acctgaatga cggtgatgcc aacggtattg ttaagtatac cgacgcgaac | 1860 |
| ggttatctga cgttcaaccc gggtgagatc agcggcgttc gtaatgctca ggtcgacggt | 1920 |

```
tatttggcgg tttgggtccc gctgggcgca agcgagaacc aagacgtgcg tgttgccgcg    1980
agcaaaagca aaaacagcag cggtctggta tacgactcta gcgcggcact ggactcccaa    2040
gttatctatg aaggctttag caattttcag gatttcgtgc aggacccgtc ccagtatacc    2100
aacaagaaaa tcgccgagaa tgcaaatttg ttcaaatcct ggggcattac ctcgtttgaa    2160
tttgccccgc agtacgtgag ctccgacgat ggtaccttcc tggacagcgt cattcagaac    2220
ggctacgcgt tcagcgatcg ctacgatatt ggtatgagca agacaacaa gtacggcagc     2280 ctggcagatc tgaaagcggc gcttaagtcc ctgcacgccg tcggtatctc cgcgatcgca    2340
gactgggtcc cggaccagat ttacaatctg cctggtgatg aagtggtgac cgccacccgt    2400
gtgaacaatt acggtgaaac gaaagacggc gcgatcatcg accacagcct gtacgtcgcg    2460
aaaacccgca cgtttggtaa cgattatcaa ggtaagtacg gtggcgctta cctggatgaa    2520
ctcaagcgtc tgtatccgca gttttttcgac cgtgttcaga tcagcaccgg caagcgtctg   2580
accaccgatg agaagattac gaagtggtcc gcgaaataca tgaatggtac caacattctg    2640
gaccgtggta gcgagtatgt tctgaagaac ggcctgtcgg gttactatgg cacgaacggt    2700
ggcaaagttt ccctgccgaa agtcgtcggc tctaaccaga gcacgaacaa caataaccaa    2760
aacggtgatg gcagcggccg tttcgagaaa agctgggta gcgtgtatta tcgttacaat     2820
gacggccagc gtgcgcgtaa tgctttcatt aaagacaacg atggtaacgt ttactacttt    2880
gacaacactg gccgtatggc catcggtgaa aagacgattg atggtaagca gtacttcttc    2940
ctggcgaacg tgttcagct gcgtgacggt accgtcaga accgtcgcgg tcaggtcttt      3000
tactacgacg agaacggtat tatgagccag acgggtaagc cgtccccgaa gccagagcca    3060
aaaccggaca caatacgtt ttctcgcaat caattcattc agattggcaa taacgtctgg     3120
gcctattacg atggtaatgg taaaagagtg atcggtcgtc agaatatcaa tggtcaagaa    3180 ctgttttctcg ataacaacgg cgtccaagtc aagggtcgca ccgcccaagt ggacggcgtg   3240
acccgttact ttgacgctaa ttctggcgag atggcgcgta accgcttcgc agaagtggag    3300
ccgggtgtct gggcttactt caacaacgat ggtgccgcgg tgaccggtag ccagaacatt    3360
aatggccaga ccctgtattt cgaccagaat ggtcaccaag ttaaaggtgc cctggttacc    3420
gtcgatggca atctgcgcta ttacgacgcg aattcgggcg acctgtatcg caaccgcttc    3480
caagaagtca atgcagctg gtactatttt gatggtaacg gtaacgcagt caaaggcatg     3540
gtgaacatta acggtcagaa tctgctgttt gataatgatg gcaaacaagt gaaaggtcac    3600
ctggtccgcg ttaatggtgt cattcgttat tacgacccga atagcggtga gatggctgtt    3660
aatcgttggg tcgagatcag cagcggttgg tgggtgtact ttgatggcga gggtcgtggt    3720
caaatctaa                                                            3729
```

<210> SEQ ID NO 4
<211> LENGTH: 1242
<212> TYPE: PRT
<213> ORGANISM: Streptococcus sp. C150

<400> SEQUENCE: 4

```
Met Ile Asn Gly Lys Glu Tyr Tyr Val Glu Asp Asp Gly Thr Val Arg
1               5                   10                  15

Lys Asn Tyr Val Leu Glu Arg Asn Gly Gly Ser Gln Tyr Phe Asn Ala
            20                  25                  30

Glu Thr Gly Glu Leu Ser Asn Gln Lys Asp Tyr Arg Phe Asp Lys Asn
        35                  40                  45
```

```
Gly Gly Thr Gly Ser Ala Ala Asp Ser Thr Thr Asn Thr Asn Val Thr
         50                  55                  60

Val Asn Gly Asp Lys Asn Ala Phe Tyr Gly Thr Glu Lys Asp Ile
 65              70                  75                  80

Glu Leu Val Asp Gly Tyr Phe Thr Ala Asn Thr Trp Tyr Arg Pro Lys
                     85                  90                  95

Glu Ile Leu Lys Asp Gly Lys Glu Trp Thr Ala Ser Thr Glu Asn Asp
                100                 105                 110

Lys Arg Pro Leu Leu Thr Val Trp Trp Pro Ser Lys Ala Ile Gln Ala
            115                 120                 125

Ser Tyr Leu Asn Tyr Met Arg Glu Glu Gly Leu Gly Thr Asn Gln Thr
            130                 135                 140

Phe Thr Ser Tyr Ser Ser Gln Thr Gln Met Asp Gln Ala Ala Leu Glu
145                 150                 155                 160

Val Gln Lys Arg Ile Glu Arg Ile Ala Arg Glu Gly Asn Thr Asp
                165                 170                 175

Trp Leu Arg Thr Thr Ile Lys Asn Phe Val Lys Thr Gln Pro Gly Trp
            180                 185                 190

Asn Ser Thr Ser Glu Asn Leu Asp Asn Ser Asp His Leu Gln Gly Gly
            195                 200                 205

Ala Leu Leu Tyr Asn Asn Ser Asn Arg Thr Ser Tyr Ala Asn Ser Asp
210                 215                 220

Tyr Arg Leu Leu Asn Arg Thr Pro Thr Gln Gln Asp Gly Thr Arg Arg
225                 230                 235                 240

Tyr Phe Lys Asp Asn Ser Ser Gly Gly Phe Glu Phe Leu Leu Ala Asn
                245                 250                 255

Asp Ile Asp Asn Ser Asn Pro Ala Val Gln Ala Glu Gln Leu Asn Trp
            260                 265                 270

Leu His Tyr Ile Met Asn Ile Gly Ser Leu Thr Gly Gly Ser Glu Asp
            275                 280                 285

Glu Asn Phe Asp Gly Val Arg Val Asp Ala Val Asp Asn Val Asn Ala
            290                 295                 300

Asp Leu Leu Gln Ile Ala Ser Asp Tyr Phe Lys Ala Lys Tyr Gly Val
305                 310                 315                 320

Glu Lys Ser Glu Glu Glu Ala Ile Lys His Leu Ser Ile Leu Glu Ala
                325                 330                 335

Trp Ser His Asn Asp Ala Tyr Tyr Asn Glu Asp Thr Lys Gly Ala Gln
            340                 345                 350

Leu Pro Met Asp Asp Pro Leu Arg Leu Ala Met Val Phe Ser Phe Leu
            355                 360                 365

Arg Pro Ile Gly Asn Arg Ser Gly Leu Glu Pro Leu Ile Thr Asn Ser
370                 375                 380

Leu Asn Asp Arg Ser Glu Ser Lys Lys Asn Thr Lys Arg Met Ala Asn
385                 390                 395                 400

Tyr Thr Phe Val Arg Ala His Asp Ser Glu Val Gln Ser Val Ile Gly
                405                 410                 415

Gln Ile Ile Lys Asn Glu Ile Asn Pro Gln Ser Thr Gly Asn Thr Phe
            420                 425                 430

Thr Leu Asp Glu Met Lys Lys Ala Phe Lys Ile Tyr Asn Ala Asp Met
            435                 440                 445

Arg Ser Ala Asn Lys Arg Tyr Thr Gln Tyr Asn Ile Pro Ser Ala Tyr
450                 455                 460
```

```
Ala Phe Met Leu Thr Asn Lys Asp Thr Val Pro Arg Val Tyr Tyr Gly
465                 470                 475                 480

Asp Leu Tyr Thr Asp Asp Gly Gln Tyr Met Ala Gln Lys Ser Pro Tyr
            485                 490                 495

His Asp Ala Ile Ser Thr Leu Leu Gln Ala Arg Ile Arg Tyr Ala Ala
                500                 505                 510

Gly Gly Gln Asp Met Lys Met Ser Tyr Val Gly Ser Gly Asn Thr Asn
            515                 520                 525

Gly Trp Asp Ala Ser Gly Val Leu Thr Ser Val Arg Tyr Gly Lys Gly
530                 535                 540

Ala Asn Asn Ala Ser Asp Ala Gly Thr Ala Glu Thr Arg Asn Gln Gly
545                 550                 555                 560

Met Ala Val Ile Leu Ser Asn Gln Pro Ala Leu Arg Leu Asn Ser Asn
                565                 570                 575

Leu Thr Ile Asn Met Gly Ala Ala His Arg Asn Gln Ala Tyr Arg Pro
                580                 585                 590

Leu Leu Leu Thr Thr Ser Asn Gly Val Ala Ser Tyr Leu Asn Asp Gly
            595                 600                 605

Asp Ala Asn Gly Ile Val Lys Tyr Thr Asp Ala Asn Gly Tyr Leu Thr
610                 615                 620

Phe Asn Pro Gly Glu Ile Ser Gly Val Arg Asn Ala Gln Val Asp Gly
625                 630                 635                 640

Tyr Leu Ala Val Trp Val Pro Leu Gly Ala Ser Glu Asn Gln Asp Val
                645                 650                 655

Arg Val Ala Ala Ser Lys Ser Lys Asn Ser Ser Gly Leu Val Tyr Asp
                660                 665                 670

Ser Ser Ala Ala Leu Asp Ser Gln Val Ile Tyr Glu Gly Phe Ser Asn
            675                 680                 685

Phe Gln Asp Phe Val Gln Asp Pro Ser Gln Tyr Thr Asn Lys Lys Ile
            690                 695                 700

Ala Glu Asn Ala Asn Leu Phe Lys Ser Trp Gly Ile Thr Ser Phe Glu
705                 710                 715                 720

Phe Ala Pro Gln Tyr Val Ser Ser Asp Gly Thr Phe Leu Asp Ser
                725                 730                 735

Val Ile Gln Asn Gly Tyr Ala Phe Ser Asp Arg Tyr Asp Ile Gly Met
            740                 745                 750

Ser Lys Asp Asn Lys Tyr Gly Ser Leu Ala Asp Leu Lys Ala Ala Leu
            755                 760                 765

Lys Ser Leu His Ala Val Gly Ile Ser Ala Ile Ala Asp Trp Val Pro
770                 775                 780

Asp Gln Ile Tyr Asn Leu Pro Gly Asp Glu Val Val Thr Ala Thr Arg
785                 790                 795                 800

Val Asn Asn Tyr Gly Glu Thr Lys Asp Gly Ala Ile Ile Asp His Ser
                805                 810                 815

Leu Tyr Val Ala Lys Thr Arg Thr Phe Gly Asn Asp Tyr Gln Gly Lys
                820                 825                 830

Tyr Gly Gly Ala Tyr Leu Asp Glu Leu Lys Arg Leu Tyr Pro Gln Phe
            835                 840                 845

Phe Asp Arg Val Gln Ile Ser Thr Gly Lys Arg Leu Thr Thr Asp Glu
            850                 855                 860

Lys Ile Thr Lys Trp Ser Ala Lys Tyr Met Asn Gly Thr Asn Ile Leu
865                 870                 875                 880

Asp Arg Gly Ser Glu Tyr Val Leu Lys Asn Gly Leu Ser Gly Tyr Tyr
```

|     |     |     |     |     | 885 |     |     |     |     | 890 |     |     |     |     | 895 |     |
| --- | --- | --- | --- | --- | --- | --- | --- | --- | --- | --- | --- | --- | --- | --- | --- | --- |

Gly Thr Asn Gly Gly Lys Val Ser Leu Pro Lys Val Gly Ser Asn
                        900                 905                 910

Gln Ser Thr Asn Asn Asn Gln Asn Gly Asp Gly Ser Gly Arg Phe
        915                 920                 925

Glu Lys Ser Trp Gly Ser Val Tyr Tyr Arg Tyr Asn Asp Gly Gln Arg
    930                 935                 940

Ala Arg Asn Ala Phe Ile Lys Asp Asn Asp Gly Asn Val Tyr Tyr Phe
945                 950                 955                 960

Asp Asn Thr Gly Arg Met Ala Ile Gly Glu Lys Thr Ile Asp Gly Lys
                965                 970                 975

Gln Tyr Phe Phe Leu Ala Asn Gly Val Gln Leu Arg Asp Gly Tyr Arg
            980                 985                 990

Gln Asn Arg Arg Gly Gln Val Phe Tyr Tyr Asp Glu Asn Gly Ile Met
        995                 1000                1005

Ser Gln Thr Gly Lys Pro Ser Pro Lys Pro Glu Pro Lys Pro Asp
    1010                1015                1020

Asn Asn Thr Phe Ser Arg Asn Gln Phe Ile Gln Ile Gly Asn Asn
    1025                1030                1035

Val Trp Ala Tyr Tyr Asp Gly Asn Gly Lys Arg Val Ile Gly Arg
    1040                1045                1050

Gln Asn Ile Asn Gly Gln Glu Leu Phe Phe Asp Asn Asn Gly Val
    1055                1060                1065

Gln Val Lys Gly Arg Thr Ala Gln Val Asp Gly Val Thr Arg Tyr
    1070                1075                1080

Phe Asp Ala Asn Ser Gly Glu Met Ala Arg Asn Arg Phe Ala Glu
    1085                1090                1095

Val Glu Pro Gly Val Trp Ala Tyr Phe Asn Asn Asp Gly Ala Ala
    1100                1105                1110

Val Thr Gly Ser Gln Asn Ile Asn Gly Gln Thr Leu Tyr Phe Asp
    1115                1120                1125

Gln Asn Gly His Gln Val Lys Gly Ala Leu Val Thr Val Asp Gly
    1130                1135                1140

Asn Leu Arg Tyr Tyr Asp Ala Asn Ser Gly Asp Leu Tyr Arg Asn
    1145                1150                1155

Arg Phe Gln Glu Val Asn Gly Ser Trp Tyr Tyr Phe Asp Gly Asn
    1160                1165                1170

Gly Asn Ala Val Lys Gly Met Val Asn Ile Asn Gly Gln Asn Leu
    1175                1180                1185

Leu Phe Asp Asn Asp Gly Lys Gln Val Lys Gly His Leu Val Arg
    1190                1195                1200

Val Asn Gly Val Ile Arg Tyr Tyr Asp Pro Asn Ser Gly Glu Met
    1205                1210                1215

Ala Val Asn Arg Trp Val Glu Ile Ser Ser Gly Trp Trp Val Tyr
    1220                1225                1230

Phe Asp Gly Glu Gly Arg Gly Gln Ile
    1235                1240

<210> SEQ ID NO 5
<211> LENGTH: 3942
<212> TYPE: DNA
<213> ORGANISM: Streptococcus mutans

<400> SEQUENCE: 5

```
atgattgacg gcaaatacta ctactatgac aacaacggca aagtacgcac caatttcacg    60
ttgatcgcgg acggtaaaat cctgcatttt gatgaaactg gcgcgtacac cgacactagc   120
attgataccg tgaacaagga tattgtcacg acgcgtagca acctgtataa gaaatacaat   180
caagtgtatg atcgcagcgc gcagagcttc gagcatgttg atcactacct gacggcggaa   240
tcttggtacc gtccgaaata cattctgaaa gatggcaaga cctggaccca gagcaccgag   300
aaggacttcc gtcctctgct gatgacctgg tggccgagcc aggaaacgca gcgccagtat   360
gtcaacttca tgaacgccca gttgggtatc aacaaaacgt acgacgacac cagcaatcag   420
ctgcaattga acatcgctgc tgcaacgatc aagcaaaga tcgaagccaa atcacgacg    480
ctgaagaaca ccgattggct gcgtcaaacg atcagcgcgt cgtcaaaaac ccaaagcgct   540
tggaatagcg acagcgaaaa gccgtttgat gaccatctgc aaaacggtgc ggttctgtat   600
gataacgaag gtaaattgac gccgtatgcc aatagcaact atcgtattct gaaccgcacg   660
ccgaccaacc agaccggtaa gaaggacccg cgttataccg ccgacaacac gatcggcggc   720
tacgagtttc tgctggccaa cgacgtggat aatagcaacc cggtggttca ggccgagcag   780
ctgaactggc tgcacttcct gatgaacttt ggtaatatct acgcaaacga ccctgacgct   840
aacttcgact ccatccgcgt tgacgctgtc gataatgtgg acgccgatct gttacagatc   900
gcgggtgact atctgaaagc ggcaaagggc atccataaga atgacaaagc ggcgaacgac   960
cacctgtcca ttctgaagc gtggagcgac aatgacactc cgtatctgca tgatgatggc  1020
gacaacatga ttaacatgga taacaaactg cgcctgagcc tgctgttctc cctggcgaaa  1080
ccgctgaatc agcgtagcgg tatgaacccg ttgattacga acagcctggt caaccgtact  1140
gatgataatg ccgaaacggc ggcagtgcca agctactctt ttatccgtgc ccacgatagc  1200
gaggtccagg attgattcg tgatatcatt aaggctgaga ttaacccgaa cgtcgtcggt  1260
tacagcttca cgatggaaga gattaagaag gcatttgaga tctacaataa ggacctgttg  1320
gccacggaga agaagtatac ccactataac accgcattga gctacgcgtt gctgctgacg  1380
aacaagagca gcgtgccgcg tgtctactat ggtgatatgt ttacggacga tggtcaatac  1440
atggcccaca gaccattaa ctacgaggca atcgaaaccc tgctgaaagc acgtatcaag  1500
tacgtgtccg gtggtcaggc tatgcgcaac cagcaagtgg gtaattcgga gatcatcacc  1560
agcgtgcgtt acggtaaagg tgcgctgaag gcgatggata cgggtgaccg cactacccgt  1620
acctctggtg tggcggtcat tgagggcaac aacccgagct gcgcctgaa ggcttctgat  1680
cgtgtggttg tgaatatggg tgcggcccac aaaaatcaag cctatcgccc gctgctgttg  1740
acgaccgata acggcattaa ggcctatcac agcgaccaag aagcggcagg cctggtgcgt  1800
tacaccaacg accgtggcga actgatcttt accgcagccg acattaaggg ctacgcaaat  1860
ccgcaagtta gcggctacct gggcgtctgg gtccctgttg gcgcagcagc tgatcaggac  1920
gttcgtgttg cggcgagcac cgcgccaagc acggacggca agagcgttca ccagaacgcg  1980
gctctggaca gccgtgtgat gttcgagggt ttctcgaact ccaggcatt tgctaccaag  2040
aaagaagagt ataccaatgt ggtcatcgct aagaatgtgg ataagttcgc ggagtggggt  2100
gtcaccgatt tcgagatggc tccgcaatac gtttctagca ccgacggtag cttttttggat  2160
agcgtgattc aaaacggtta tgcttttacc gaccgttacg acctgggcat cagcaagccg  2220
aacaaatatg gcaccgcgga cgatctggtt aaagcgatta aggcattgca cagcaaaggc  2280
atcaaagtta tggcggattg ggttccggac cagatgtatg ccctgccgga aaagaggtt  2340
gtgacggcaa cccgtgttga caaatacggt acgccggtag ctggcagcca gatcaaaaac  2400
```

```
acgctgtacg tggtcgatgg taaatctagc ggtaaggacc agcaggcgaa gtacggtggt    2460
gccttcctgg aagagctgca agcgaagtat ccggaactgt tcgcgcgcaa acagattagc    2520
accggtgttc cgatggaccc gagcgtcaag attaagcaat ggagcgcaaa atacttcaac    2580
ggcacgaata tcctgggtcg tggtgctggt tacgtgctga agatcaggc aaccaacacc     2640 tactttaaca tcagcgacaa taaagagatc aatttcctgc aaagacgtt gctgaaccag     2700 gattctcaag ttggctttag ctacgacggt aagggctatg tgtactacag cacctcgggc    2760
taccaggcta aaacacgtt catcagcgag ggtgacaagt ggtattactt cgacaataac     2820
ggttatatgg ttaccggcgc acagagcatt aatggtgtga actattactt cctgccgaat    2880
ggtttacagc tgcgtgatgc gattctgaaa aatgaggacg tacgtacgc gtattatggc     2940 aatgatggtc gccgctacga gaatggctat tatcagttta tgagcggtgt ttggcgccat    3000
ttcaataatg gcgagatgtc cgttggtctg accgtcattg acggtcaagt tcaatacttt    3060
gacgagatgg gttaccaggc gaaaggcaaa ttcgttacca ccgcggatgg taagatccgt    3120
tacttcgata gcagagcgg caatatgtat cgtaatcgtt tcattgagaa cgaagagggc    3180
aaatggctgt acctgggtga ggacggcgcg gcagtcaccg tagccagac gatcaatggt    3240 cagcacctgt attttcgtgc taacggcgtt caggttaagg gtgagttcgt gaccgatcgt    3300
catgccgcca tctcttatta cgacggcaac agcggtgatc agatccgcaa ccgtttcgtc    3360
cgcaatgcgc aaggccagtg gttttacttt gacaacaatg gctatgcagt aactggtgct    3420
cgtacgatca acgccagca cctgtatttc cgcgcgaacg tgttcaggt aaaaggtgag    3480 tttgttacgg accgccacgg ccgcattagc tattatgatg gtaatagcgg tgaccaaatt    3540
cgcaatcgtt tcgtgcgtaa tgcacagggg cagtggttct acttcgacaa taatggttat    3600
gcagtcacgg gtgcacgtac cattaacggc caacacctgt actttcgcgc caatggtgtg    3660
caagtgaaag gcgaatttgt tactgatcgt tatggtcgta tcagctacta tgatggcaat    3720
tctggcgacc aaattcgcaa tcgctttgtt cgtaacgccc aaggtcaatg gttctatttc    3780
gacaacaacg ttacgcggt gaccggtgcc cgcacgatta atggtcaaca cttgtacttc    3840
cgtgccaacg gtgtccaggt gaagggtgaa tttgtgaccg accgctatgg tcgcatttct    3900
tactacgacg caaattccgg tgaacgcgtc cgtatcaatt aa                       3942
```

<210> SEQ ID NO 6
<211> LENGTH: 1313
<212> TYPE: PRT
<213> ORGANISM: Streptococcus mutans

<400> SEQUENCE: 6

```
Met Ile Asp Gly Lys Tyr Tyr Tyr Asp Asn Asn Gly Lys Val Arg
1               5                   10                  15

Thr Asn Phe Thr Leu Ile Ala Asp Gly Lys Ile Leu His Phe Asp Glu
            20                  25                  30

Thr Gly Ala Tyr Thr Asp Thr Ser Ile Asp Thr Val Asn Lys Asp Ile
        35                  40                  45

Val Thr Thr Arg Ser Asn Leu Tyr Lys Lys Tyr Asn Gln Val Tyr Asp
    50                  55                  60

Arg Ser Ala Gln Ser Phe Glu His Val Asp His Tyr Leu Thr Ala Glu
65                  70                  75                  80

Ser Trp Tyr Arg Pro Lys Tyr Ile Leu Lys Asp Gly Lys Thr Trp Thr
                85                  90                  95
```

-continued

```
Gln Ser Thr Glu Lys Asp Phe Arg Pro Leu Leu Met Thr Trp Trp Pro
             100                 105                 110

Ser Gln Glu Thr Gln Arg Gln Tyr Val Asn Phe Met Asn Ala Gln Leu
        115                 120                 125

Gly Ile Asn Lys Thr Tyr Asp Asp Thr Ser Asn Gln Leu Gln Leu Asn
    130                 135                 140

Ile Ala Ala Ala Thr Ile Gln Ala Lys Ile Glu Ala Lys Ile Thr Thr
145                 150                 155                 160

Leu Lys Asn Thr Asp Trp Leu Arg Gln Thr Ile Ser Ala Phe Val Lys
                165                 170                 175

Thr Gln Ser Ala Trp Asn Ser Asp Ser Glu Lys Pro Phe Asp Asp His
            180                 185                 190

Leu Gln Asn Gly Ala Val Leu Tyr Asp Asn Glu Gly Lys Leu Thr Pro
        195                 200                 205

Tyr Ala Asn Ser Asn Tyr Arg Ile Leu Asn Arg Thr Pro Thr Asn Gln
    210                 215                 220

Thr Gly Lys Lys Asp Pro Arg Tyr Thr Ala Asp Asn Thr Ile Gly Gly
225                 230                 235                 240

Tyr Glu Phe Leu Leu Ala Asn Asp Val Asp Asn Ser Asn Pro Val Val
                245                 250                 255

Gln Ala Glu Gln Leu Asn Trp Leu His Phe Leu Met Asn Phe Gly Asn
            260                 265                 270

Ile Tyr Ala Asn Asp Pro Asp Ala Asn Phe Asp Ser Ile Arg Val Asp
        275                 280                 285

Ala Val Asp Asn Val Asp Ala Asp Leu Leu Gln Ile Ala Gly Asp Tyr
    290                 295                 300

Leu Lys Ala Ala Lys Gly Ile His Lys Asn Asp Lys Ala Ala Asn Asp
305                 310                 315                 320

His Leu Ser Ile Leu Glu Ala Trp Ser Asp Asn Asp Thr Pro Tyr Leu
                325                 330                 335

His Asp Asp Gly Asp Asn Met Ile Asn Met Asp Asn Lys Leu Arg Leu
            340                 345                 350

Ser Leu Leu Phe Ser Leu Ala Lys Pro Leu Asn Gln Arg Ser Gly Met
        355                 360                 365

Asn Pro Leu Ile Thr Asn Ser Leu Val Asn Arg Thr Asp Asp Asn Ala
    370                 375                 380

Glu Thr Ala Ala Val Pro Ser Tyr Ser Phe Ile Arg Ala His Asp Ser
385                 390                 395                 400

Glu Val Gln Asp Leu Ile Arg Asp Ile Ile Lys Ala Glu Ile Asn Pro
                405                 410                 415

Asn Val Val Gly Tyr Ser Phe Thr Met Glu Glu Ile Lys Lys Ala Phe
            420                 425                 430

Glu Ile Tyr Asn Lys Asp Leu Leu Ala Thr Glu Lys Lys Tyr Thr His
        435                 440                 445

Tyr Asn Thr Ala Leu Ser Tyr Ala Leu Leu Thr Asn Lys Ser Ser
    450                 455                 460

Val Pro Arg Val Tyr Tyr Gly Asp Met Phe Thr Asp Asp Gly Gln Tyr
465                 470                 475                 480

Met Ala His Lys Thr Ile Asn Tyr Glu Ala Ile Glu Thr Leu Leu Lys
                485                 490                 495

Ala Arg Ile Lys Tyr Val Ser Gly Gln Ala Met Arg Asn Gln Gln
        500                 505                 510

Val Gly Asn Ser Glu Ile Ile Thr Ser Val Arg Tyr Gly Lys Gly Ala
```

```
            515                 520                 525
Leu Lys Ala Met Asp Thr Gly Asp Arg Thr Arg Thr Ser Gly Val
530                 535                 540

Ala Val Ile Glu Gly Asn Asn Pro Ser Leu Arg Leu Lys Ala Ser Asp
545                 550                 555                 560

Arg Val Val Val Asn Met Gly Ala Ala His Lys Asn Gln Ala Tyr Arg
                565                 570                 575

Pro Leu Leu Leu Thr Thr Asp Asn Gly Ile Lys Ala Tyr His Ser Asp
                580                 585                 590

Gln Glu Ala Ala Gly Leu Val Arg Tyr Thr Asn Asp Arg Gly Glu Leu
                595                 600                 605

Ile Phe Thr Ala Ala Asp Ile Lys Gly Tyr Ala Asn Pro Gln Val Ser
        610                 615                 620

Gly Tyr Leu Gly Val Trp Val Pro Val Gly Ala Ala Asp Gln Asp
625                 630                 635                 640

Val Arg Val Ala Ala Ser Thr Ala Pro Ser Thr Asp Gly Lys Ser Val
                645                 650                 655

His Gln Asn Ala Ala Leu Asp Ser Arg Val Met Phe Glu Gly Phe Ser
                660                 665                 670

Asn Phe Gln Ala Phe Ala Thr Lys Lys Glu Glu Tyr Thr Asn Val Val
        675                 680                 685

Ile Ala Lys Asn Val Asp Lys Phe Ala Glu Trp Gly Val Thr Asp Phe
        690                 695                 700

Glu Met Ala Pro Gln Tyr Val Ser Ser Thr Asp Gly Ser Phe Leu Asp
705                 710                 715                 720

Ser Val Ile Gln Asn Gly Tyr Ala Phe Thr Asp Arg Tyr Asp Leu Gly
                725                 730                 735

Ile Ser Lys Pro Asn Lys Tyr Gly Thr Ala Asp Asp Leu Val Lys Ala
                740                 745                 750

Ile Lys Ala Leu His Ser Lys Gly Ile Lys Val Met Ala Asp Trp Val
        755                 760                 765

Pro Asp Gln Met Tyr Ala Leu Pro Glu Lys Glu Val Val Thr Ala Thr
770                 775                 780

Arg Val Asp Lys Tyr Gly Thr Pro Val Ala Gly Ser Gln Ile Lys Asn
785                 790                 795                 800

Thr Leu Tyr Val Val Asp Gly Lys Ser Ser Gly Lys Asp Gln Gln Ala
                805                 810                 815

Lys Tyr Gly Gly Ala Phe Leu Glu Glu Leu Gln Ala Lys Tyr Pro Glu
                820                 825                 830

Leu Phe Ala Arg Lys Gln Ile Ser Thr Gly Val Pro Met Asp Pro Ser
        835                 840                 845

Val Lys Ile Lys Gln Trp Ser Ala Lys Tyr Phe Asn Gly Thr Asn Ile
        850                 855                 860

Leu Gly Arg Gly Ala Gly Tyr Val Leu Lys Asp Gln Ala Thr Asn Thr
865                 870                 875                 880

Tyr Phe Asn Ile Ser Asp Asn Lys Glu Ile Asn Phe Leu Pro Lys Thr
                885                 890                 895

Leu Leu Asn Gln Asp Ser Gln Val Gly Phe Ser Tyr Asp Gly Lys Gly
                900                 905                 910

Tyr Val Tyr Tyr Ser Thr Ser Gly Tyr Gln Ala Lys Asn Thr Phe Ile
                915                 920                 925

Ser Glu Gly Asp Lys Trp Tyr Tyr Phe Asp Asn Asn Gly Tyr Met Val
                930                 935                 940
```

Thr Gly Ala Gln Ser Ile Asn Gly Val Asn Tyr Tyr Phe Leu Pro Asn
945                 950                 955                 960

Gly Leu Gln Leu Arg Asp Ala Ile Leu Lys Asn Glu Asp Gly Thr Tyr
            965                 970                 975

Ala Tyr Tyr Gly Asn Asp Gly Arg Arg Tyr Glu Asn Gly Tyr Tyr Gln
        980                 985                 990

Phe Met Ser Gly Val Trp Arg His Phe Asn Asn Gly Glu Met Ser Val
        995                 1000                1005

Gly Leu Thr Val Ile Asp Gly Gln Val Gln Tyr Phe Asp Glu Met
1010                1015                1020

Gly Tyr Gln Ala Lys Gly Lys Phe Val Thr Ala Asp Gly Lys
1025                1030                1035

Ile Arg Tyr Phe Asp Lys Gln Ser Gly Asn Met Tyr Arg Asn Arg
1040                1045                1050

Phe Ile Glu Asn Glu Glu Gly Lys Trp Leu Tyr Leu Gly Glu Asp
1055                1060                1065

Gly Ala Ala Val Thr Gly Ser Gln Thr Ile Asn Gly Gln His Leu
1070                1075                1080

Tyr Phe Arg Ala Asn Gly Val Gln Val Lys Gly Glu Phe Val Thr
1085                1090                1095

Asp Arg His Gly Arg Ile Ser Tyr Tyr Asp Gly Asn Ser Gly Asp
1100                1105                1110

Gln Ile Arg Asn Arg Phe Val Arg Asn Ala Gln Gly Gln Trp Phe
1115                1120                1125

Tyr Phe Asp Asn Asn Gly Tyr Ala Val Thr Gly Ala Arg Thr Ile
1130                1135                1140

Asn Gly Gln His Leu Tyr Phe Arg Ala Asn Gly Val Gln Val Lys
1145                1150                1155

Gly Glu Phe Val Thr Asp Arg His Gly Arg Ile Ser Tyr Tyr Asp
1160                1165                1170

Gly Asn Ser Gly Asp Gln Ile Arg Asn Arg Phe Val Arg Asn Ala
1175                1180                1185

Gln Gly Gln Trp Phe Tyr Phe Asp Asn Asn Gly Tyr Ala Val Thr
1190                1195                1200

Gly Ala Arg Thr Ile Asn Gly Gln His Leu Tyr Phe Arg Ala Asn
1205                1210                1215

Gly Val Gln Val Lys Gly Glu Phe Val Thr Asp Arg Tyr Gly Arg
1220                1225                1230

Ile Ser Tyr Tyr Asp Gly Asn Ser Gly Asp Gln Ile Arg Asn Arg
1235                1240                1245

Phe Val Arg Asn Ala Gln Gly Gln Trp Phe Tyr Phe Asp Asn Asn
1250                1255                1260

Gly Tyr Ala Val Thr Gly Ala Arg Thr Ile Asn Gly Gln His Leu
1265                1270                1275

Tyr Phe Arg Ala Asn Gly Val Gln Val Lys Gly Glu Phe Val Thr
1280                1285                1290

Asp Arg Tyr Gly Arg Ile Ser Tyr Tyr Asp Ala Asn Ser Gly Glu
1295                1300                1305

Arg Val Arg Ile Asn
1310

<210> SEQ ID NO 7
<211> LENGTH: 4047

```
<212> TYPE: DNA
<213> ORGANISM: Streptococcus sanguinis

<400> SEQUENCE: 7
atgattgatg gtaaaaagta ttacgtacag gacgacggca cggttaagaa gaatttcgcg      60
gttgagctga atggcaagat cctgtacttc gatgcagaga ctggtgcgtt gattgacagc     120
gcggagtatc aattccaaca aggcaccagc agcctgaata atgagttcac tcaaaagaac     180
gccttttacg gtacgaccga taaggatgtg gaaaccattg atggttactt gaccgccgat     240
tcctggtatc gtccgaagtt cattctgaaa gatggcaaaa cctggacggc gagcacggaa     300
attgacttgc gtccgttgtt gatggcgtgg tggccggaca acagaccca ggttagctac      360
ctgaattaca tgaaccagca aggcttgggt gcaggcgcct tcgaaaacaa agtagagcag     420
gcaattctga ccggtgcgtc ccaacaggta caacgtaaaa tcgaagaacg catcggtaaa     480
gagggtgata ccaagtggct gcgtaccctg atgggtgcat ttgtaaagac ccagccgaac     540
tggaacatta agaccgagtc cgaaaccact ggcacgaata agatcatct gcaaggtggc      600
gcactgctgt atagcaattc cgacaagacg agccatgcca actctaagta ccgtatcctg     660
aaccgcaccc cgaccaacca aacgggcacg ccgaaatact ttattgacaa gagcaatggt     720
ggttatgaat ttctgctggc gaatgacttt gacaatagca atccggcagt gcaagcggaa     780
cagctgaact ggttgcactt tatgatgaat tttggctcca tcgttgcaaa tgatccgacg     840
gccaacttcg acggcgtccg cgttgacgct gtggataacg tgaatgcgga tctgttgcaa     900
attgcgagcg actatttcaa gagccgctat aaagtcggcg aaagcgaaga gaggccatt       960
aagcacctgt ccatcctgga agcgtggagc gacaacgacc cggactacaa caaggatact    1020
aaaggtgccc aactgccgat cgacaacaaa ctgcgtctga gcctgctgta ctccttcatg    1080
cgtaagctga gcatccgtag cggcgtcgag ccgaccatca ccaactctct gaatgatcgc    1140
agcacgagaa gaagaatgg tgagcgtatg gcaaactata tcttcgttcg tgcacatgat    1200
agcgaggtgc aaacggtcat cgccgacatt atccgtgaga catcaatcc gaataccgac    1260
ggcctgacgt tcacgatgga tgaactgaag caggccttta aaatttacaa tgaggatatg    1320
cgtaaagccg acaaaaagta cacgcagttc aatatcccga ccgcgcacgc gctgatgctg    1380
agcaacaaag attctatcac ccgcgtttac tacggtgacc tgtatacgga tgacggtcag    1440
tatatggaaa agaaaagccc gtatcacgac gccattgacg ctctgctgcg tgcgcgtatc    1500
aaatatgttg cgggtggtca ggacatgaag gtgacctata tgggcgtgcc gcgtgaggca    1560
gataaatgga gctataacgg catcctgacc agcgttcgtt atggtacggg tgccaacgag    1620
gcaaccgacg agggtacggc agaaacccgt acccagggca tggccgtcat tgccagcaac    1680
aatccgaacc tgaaactgaa cgagtgggac aagttgcagg tcaacatggg tgcagctcac    1740
aaaaaccaat actatcgtcc ggtgctgctg accaccaagg acggcatctc gcgctacctg    1800
accgacgaag aagtccccgca gagcctgtgg aaaaagaccg atgcgaacgg catcttgacg    1860
tttgacatga atgatattgc gggttacagc aacgtccaag tgagcggtta tctggccgtc    1920
tgggttcctg tgggtgcgaa ggcggaccag gacgctcgtg ttacggcatc taagaagaaa    1980
aatgcctctg gcaagtttta cgaaagcagc gcagccctgg actcccagct gatctatgag    2040
ggcttcagca attttcagga ctttgccacc cgtgacgacc agtacactaa caaggttatc    2100
gcgaaaaacg tcaatctgtt taagagtgg ggcgtcacca gcttcgaatt gccgccacag      2160
tatgtgagca gccaagacgg tacgttcctg gatagcatca tccagaatgg ttatgcattc    2220
```

```
gaagatcgct atgatatggc gatgagcaaa acaataagt acggtagctt gaacgacctg    2280
ttgaacgcct tgcgtgcact gcatagcgtg aatatccaag cgattgcgga ttgggtgccg    2340
gaccagattt acaatctgcc gggtaaagaa gttgtcactg caacccgtgt taacaattat    2400
ggcacgtatc gtgagggtag cgagattaaa gagaacctgt acgttgctaa caccaaaacc    2460
aatggtacgg actaccaagg taagtatggt ggtgcgttct tggacgagct gaaagccaaa    2520
taccctgaga ttttgagcg cgtccaaatc agcaacggcc agaagatgac caccgacgag    2580
aagattacga atggtccgc caaacacttt aacggcacga acattctggg tcgtggtgcg    2640
tattatgtgc tgaaagactg ggcgagcaac gagtacctga ataacaaaaa tggcgagatg    2700
gttctgccga agcagctggt taataaaaat gcatataccg gcttcgtcag cgacgcgagc    2760
ggcaccaaat actattctac cagcggctat caggctcgta atagctttat tcaagatgaa    2820
aatggtaatt ggtactactt caataaccgt ggttatttgg tgacgggtgc acaggaaatc    2880
gacggtaagc aactgtattt cctgaaaaac ggcattcagc tgcgtgattc tctgcgtgag    2940
gacgaaaacg gcaaccagta ttactatgat aagacgggtg cgcaagttct gaatcgttat    3000
tacactacgg acggccaaaa ttggcgctac ttcgacgtta aaggcgtcat ggcccgtggt    3060
ctggtcacga tgggtggtaa ccaacaattc tttgaccaaa acggttacca ggttaaaggc    3120
aaaattgcgc gtgcaaaaga cggtaaactg cgttacttcg ataaagacag cggtaatgcg    3180
gcagctaacc gtttcgccca aggcgataac cctagcgact ggtactattt cggtgcagat    3240
ggtgttgcgg ttacgggcct gcaaaaggtt ggtcagcaaa ctctgtactt tgatcaggac    3300
ggcaagcagg tgaaaggtaa agttgttacc ttggcggaca aaagcattcg ttatttcgat    3360
gcaaacagcg gcgagatggc ggtgaacaag tttgtggaag gtgctaagaa cgtgtggtac    3420
tacttcgatc aagcaggcaa agcggtgacc ggcctgcaaa ccatcaataa acaagtgctg    3480
tatttcgacc aggatggtaa acaagtcaaa ggtaaggtgg tcacgctggc tgataagtct    3540
atccgctact tcgacgcgaa cagcggtgag atggcagtgg gcaaattcgc cgaaggcgca    3600
aagaatgagt ggtattactt tgaccaggcg ggcaaggctg ttaccggtct gcaaaagatc    3660
ggccaacaga cgctgtattt cgaccagaac ggtaaacagg ttaagggtaa agtggtcacc    3720
ctggcggata agagcatccg ctatttcgac gctaactctg gcgaaatggc aagcaataag    3780
ttcgttgagg gtgccaaaaa tgaatggtac tatttcgatc aggctggcaa ggcagtgacg    3840
ggtctgcaac aaattggcca gcagaccctg tattttgacc agaatggcaa acaggtgaag    3900
ggtaagattg tgtatgttaa tggtgcgaat cgctactttg atgccaatag cggtgaaatg    3960
gcgcgtaaca gtggattca gctggaagat ggcagctgga tgtattttga ccgcaatggt    4020
cgtggtcgtc gtttcggttg gaactaa                                        4047
```

<210> SEQ ID NO 8
<211> LENGTH: 1348
<212> TYPE: PRT
<213> ORGANISM: Streptococcus sanguinis

<400> SEQUENCE: 8

```
Met Ile Asp Gly Lys Lys Tyr Tyr Val Gln Asp Gly Thr Val Lys
1               5                   10                  15

Lys Asn Phe Ala Val Glu Leu Asn Gly Lys Ile Leu Tyr Phe Asp Ala
                20                  25                  30

Glu Thr Gly Ala Leu Ile Asp Ser Ala Glu Tyr Gln Phe Gln Gln Gly
            35                  40                  45
```

```
Thr Ser Ser Leu Asn Asn Glu Phe Thr Gln Lys Asn Ala Phe Tyr Gly
    50                  55                  60

Thr Thr Asp Lys Asp Val Glu Thr Ile Asp Gly Tyr Leu Thr Ala Asp
65                  70                  75                  80

Ser Trp Tyr Arg Pro Lys Phe Ile Leu Lys Asp Gly Lys Thr Trp Thr
                85                  90                  95

Ala Ser Thr Glu Ile Asp Leu Arg Pro Leu Leu Met Ala Trp Trp Pro
            100                 105                 110

Asp Lys Gln Thr Gln Val Ser Tyr Leu Asn Tyr Met Asn Gln Gln Gly
        115                 120                 125

Leu Gly Ala Gly Ala Phe Glu Asn Lys Val Glu Gln Ala Ile Leu Thr
    130                 135                 140

Gly Ala Ser Gln Gln Val Gln Arg Lys Ile Glu Glu Arg Ile Gly Lys
145                 150                 155                 160

Glu Gly Asp Thr Lys Trp Leu Arg Thr Leu Met Gly Ala Phe Val Lys
                165                 170                 175

Thr Gln Pro Asn Trp Asn Ile Lys Thr Glu Ser Glu Thr Thr Gly Thr
            180                 185                 190

Asn Lys Asp His Leu Gln Gly Gly Ala Leu Leu Tyr Ser Asn Ser Asp
        195                 200                 205

Lys Thr Ser His Ala Asn Ser Lys Tyr Arg Ile Leu Asn Arg Thr Pro
    210                 215                 220

Thr Asn Gln Thr Gly Thr Pro Lys Tyr Phe Ile Asp Lys Ser Asn Gly
225                 230                 235                 240

Gly Tyr Glu Phe Leu Leu Ala Asn Asp Phe Asn Ser Asn Pro Ala
                245                 250                 255

Val Gln Ala Glu Gln Leu Asn Trp Leu His Phe Met Met Asn Phe Gly
        260                 265                 270

Ser Ile Val Ala Asn Asp Pro Thr Ala Asn Phe Asp Gly Val Arg Val
    275                 280                 285

Asp Ala Val Asp Asn Val Asn Ala Asp Leu Leu Gln Ile Ala Ser Asp
    290                 295                 300

Tyr Phe Lys Ser Arg Tyr Lys Val Gly Glu Ser Glu Glu Ala Ile
305                 310                 315                 320

Lys His Leu Ser Ile Leu Glu Ala Trp Ser Asp Asn Asp Pro Asp Tyr
                325                 330                 335

Asn Lys Asp Thr Lys Gly Ala Gln Leu Pro Ile Asp Asn Lys Leu Arg
            340                 345                 350

Leu Ser Leu Leu Tyr Ser Phe Met Arg Lys Leu Ser Ile Arg Ser Gly
        355                 360                 365

Val Glu Pro Thr Ile Thr Asn Ser Leu Asn Asp Arg Ser Thr Glu Lys
    370                 375                 380

Lys Asn Gly Glu Arg Met Ala Asn Tyr Ile Phe Val Arg Ala His Asp
385                 390                 395                 400

Ser Glu Val Gln Thr Val Ile Ala Asp Ile Arg Glu Asn Ile Asn
                405                 410                 415

Pro Asn Thr Asp Gly Leu Thr Phe Thr Met Asp Glu Leu Lys Gln Ala
            420                 425                 430

Phe Lys Ile Tyr Asn Glu Asp Met Arg Lys Ala Asp Lys Lys Tyr Thr
        435                 440                 445

Gln Phe Asn Ile Pro Thr Ala His Ala Leu Met Leu Ser Asn Lys Asp
    450                 455                 460

Ser Ile Thr Arg Val Tyr Tyr Gly Asp Leu Tyr Thr Asp Asp Gly Gln
```

```
            465                 470                 475                 480
Tyr Met Glu Lys Lys Ser Pro Tyr His Asp Ala Ile Asp Ala Leu Leu
                    485                 490                 495

Arg Ala Arg Ile Lys Tyr Val Ala Gly Gly Gln Asp Met Lys Val Thr
                    500                 505                 510

Tyr Met Gly Val Pro Arg Glu Ala Asp Lys Trp Ser Tyr Asn Gly Ile
                    515                 520                 525

Leu Thr Ser Val Arg Tyr Gly Thr Gly Ala Asn Glu Ala Thr Asp Glu
                    530                 535                 540

Gly Thr Ala Glu Thr Arg Thr Gln Gly Met Ala Val Ile Ala Ser Asn
545                 550                 555                 560

Asn Pro Asn Leu Lys Leu Asn Glu Trp Asp Lys Leu Gln Val Asn Met
                    565                 570                 575

Gly Ala Ala His Lys Asn Gln Tyr Tyr Arg Pro Val Leu Leu Thr Thr
                    580                 585                 590

Lys Asp Gly Ile Ser Arg Tyr Leu Thr Asp Glu Val Pro Gln Ser
                    595                 600                 605

Leu Trp Lys Lys Thr Asp Ala Asn Gly Ile Leu Thr Phe Asp Met Asn
                    610                 615                 620

Asp Ile Ala Gly Tyr Ser Asn Val Gln Val Ser Gly Tyr Leu Ala Val
625                 630                 635                 640

Trp Val Pro Val Gly Ala Lys Ala Asp Gln Asp Ala Arg Val Thr Ala
                    645                 650                 655

Ser Lys Lys Lys Asn Ala Ser Gly Gln Val Tyr Glu Ser Ser Ala Ala
                    660                 665                 670

Leu Asp Ser Gln Leu Ile Tyr Glu Gly Phe Ser Asn Phe Gln Asp Phe
                    675                 680                 685

Ala Thr Arg Asp Asp Gln Tyr Thr Asn Lys Val Ile Ala Lys Asn Val
                    690                 695                 700

Asn Leu Phe Lys Glu Trp Gly Val Thr Ser Phe Glu Leu Pro Pro Gln
705                 710                 715                 720

Tyr Val Ser Ser Gln Asp Gly Thr Phe Leu Asp Ser Ile Ile Gln Asn
                    725                 730                 735

Gly Tyr Ala Phe Glu Asp Arg Tyr Asp Met Ala Met Ser Lys Asn Asn
                    740                 745                 750

Lys Tyr Gly Ser Leu Asn Asp Leu Leu Asn Ala Leu Arg Ala Leu His
                    755                 760                 765

Ser Val Asn Ile Gln Ala Ile Ala Asp Trp Val Pro Asp Gln Ile Tyr
770                 775                 780

Asn Leu Pro Gly Lys Glu Val Val Thr Ala Thr Arg Val Asn Asn Tyr
785                 790                 795                 800

Gly Thr Tyr Arg Glu Gly Ser Glu Ile Lys Glu Asn Leu Tyr Val Ala
                    805                 810                 815

Asn Thr Lys Thr Asn Gly Thr Asp Tyr Gln Gly Lys Tyr Gly Gly Ala
                    820                 825                 830

Phe Leu Asp Glu Leu Lys Ala Lys Tyr Pro Glu Ile Phe Glu Arg Val
                    835                 840                 845

Gln Ile Ser Asn Gly Gln Lys Met Thr Thr Asp Glu Lys Ile Thr Lys
                    850                 855                 860

Trp Ser Ala Lys His Phe Asn Gly Thr Asn Ile Leu Gly Arg Gly Ala
865                 870                 875                 880

Tyr Tyr Val Leu Lys Asp Trp Ala Ser Asn Glu Tyr Leu Asn Asn Lys
                    885                 890                 895
```

-continued

Asn Gly Glu Met Val Leu Pro Lys Gln Leu Val Asn Lys Asn Ala Tyr
            900                 905                 910
Thr Gly Phe Val Ser Asp Ala Ser Gly Thr Lys Tyr Tyr Ser Thr Ser
            915                 920                 925
Gly Tyr Gln Ala Arg Asn Ser Phe Ile Gln Asp Glu Asn Gly Asn Trp
            930                 935                 940
Tyr Tyr Phe Asn Asn Arg Gly Tyr Leu Val Thr Gly Ala Gln Glu Ile
945                 950                 955                 960
Asp Gly Lys Gln Leu Tyr Phe Leu Lys Asn Gly Ile Gln Leu Arg Asp
                965                 970                 975
Ser Leu Arg Glu Asp Glu Asn Gly Asn Gln Tyr Tyr Asp Lys Thr
            980                 985                 990
Gly Ala Gln Val Leu Asn Arg Tyr Tyr Thr Thr Asp Gly Gln Asn Trp
            995                 1000                1005
Arg Tyr Phe Asp Val Lys Gly Val Met Ala Arg Gly Leu Val Thr
            1010                1015                1020
Met Gly Gly Asn Gln Gln Phe Phe Asp Gln Asn Gly Tyr Gln Val
            1025                1030                1035
Lys Gly Lys Ile Ala Arg Ala Lys Asp Gly Lys Leu Arg Tyr Phe
            1040                1045                1050
Asp Lys Asp Ser Gly Asn Ala Ala Ala Asn Arg Phe Ala Gln Gly
            1055                1060                1065
Asp Asn Pro Ser Asp Trp Tyr Tyr Phe Gly Ala Asp Gly Val Ala
            1070                1075                1080
Val Thr Gly Leu Gln Lys Val Gly Gln Gln Thr Leu Tyr Phe Asp
            1085                1090                1095
Gln Asp Gly Lys Gln Val Lys Gly Lys Val Val Thr Leu Ala Asp
            1100                1105                1110
Lys Ser Ile Arg Tyr Phe Asp Ala Asn Ser Gly Glu Met Ala Val
            1115                1120                1125
Asn Lys Phe Val Glu Gly Ala Lys Asn Val Trp Tyr Tyr Phe Asp
            1130                1135                1140
Gln Ala Gly Lys Ala Val Thr Gly Leu Gln Thr Ile Asn Lys Gln
            1145                1150                1155
Val Leu Tyr Phe Asp Gln Gly Lys Gln Val Lys Gly Lys Val
            1160                1165                1170
Val Thr Leu Ala Asp Lys Ser Ile Arg Tyr Phe Asp Ala Asn Ser
            1175                1180                1185
Gly Glu Met Ala Val Gly Lys Phe Ala Glu Gly Ala Lys Asn Glu
            1190                1195                1200
Trp Tyr Tyr Phe Asp Gln Ala Gly Lys Ala Val Thr Gly Leu Gln
            1205                1210                1215
Lys Ile Gly Gln Gln Thr Leu Tyr Phe Asp Gln Asn Gly Lys Gln
            1220                1225                1230
Val Lys Gly Lys Val Val Thr Leu Ala Asp Lys Ser Ile Arg Tyr
            1235                1240                1245
Phe Asp Ala Asn Ser Gly Glu Met Ala Ser Asn Lys Phe Val Glu
            1250                1255                1260
Gly Ala Lys Asn Glu Trp Tyr Tyr Phe Asp Gln Ala Gly Lys Ala
            1265                1270                1275
Val Thr Gly Leu Gln Gln Ile Gly Gln Gln Thr Leu Tyr Phe Asp
            1280                1285                1290

```
Gln Asn Gly Lys Gln Val Lys Gly Lys Ile Val Tyr Val Asn Gly
    1295                1300                1305

Ala Asn Arg Tyr Phe Asp Ala Asn Ser Gly Glu Met Ala Arg Asn
    1310                1315                1320

Lys Trp Ile Gln Leu Glu Asp Gly Ser Trp Met Tyr Phe Asp Arg
    1325                1330                1335

Asn Gly Arg Gly Arg Arg Phe Gly Trp Asn
    1340                1345

<210> SEQ ID NO 9
<211> LENGTH: 3744
<212> TYPE: DNA
<213> ORGANISM: Streptococcus salivarius

<400> SEQUENCE: 9
atgccaagcc acattaagac catcaacggc aaacaatact acgtggagga tgacggtacg      60
attcgcaaga attacgtcct ggagcgtatc ggtggcagcc aatactttaa tgcagaaacc     120
ggtgaactgt ctaatcagaa agagtatcgt ttcgacaaaa atggtggtac tggtagcagc     180
gcggacagca cgaacaccaa cgtgactgtg aacggtgaca aaacgcgatt ttacggtacc     240
acggacaaag acattgagct ggtcgacggc tatttcaccg cgaacacctg gtatcgcccg     300
aaagaaatcc tgaaagacgg caaagaatgg accgccagca cggagaacga taaacgcccg     360
ctgctgaccg tctggtggcc tagcaaagca atccaggcgt cttatctgaa ctacatgaaa     420
gagcaaggcc tgggtaccaa ccaaacgtac acgagcttct ccagccaaac ccaaatggat     480
caagcagccc tggaagtgca aaagcgtatt gaagagcgca tcgcacgcga gggcaatacc     540
gactggctgc gcacgaccat caagaacttc gtgaaaaccc aacggggttg aacagcacc     600 tctgaaaatc tggacaataa tgatcatctg caaggtggcg ccctgctgta caataacgac     660
tcccgcacga gccacgcgaa cagcgactat cgcctgctga atcgtacgcc gaccagccag     720
accggcaaac acaatccgaa atacaccaaa gataccagca tggtggtttt cgaatttctg     780
ctggcgaacg acatcgataa ctctaatccg gcggttcaag cagagcaact gaactggctg     840
cattacatta tgaacatcgg taccatcacg ggcggttctg aggatgaaaa cttcgacggc     900
gttcgtgttg acgctgtgga taatgtgaat gcggatctgc tgcaaatcgc gagcgactat     960
ttcaaagcaa atacggtgc tgatcaaagc caagatcagg cgatcaaaca cttgagcatc    1020
ctggaagcgt ggtcccataa cgacgcctac tataacgaag ataccaaagg cgcgcagttg    1080
ccgatggatg atccgatgca cctggctctg gtctactcgc tgctgcgtcc gatcggcaat    1140
cgcagcggtg tggaaccgct gatttccaac agcctgaatg accgtagcga gtccggtaag    1200
aacagcaaac gtatggcgaa ctacgcgttc gtacgcgcgc atgatagcga ggtgcaatcg    1260
attattggcc agatcatcaa aaacgagatc aatccgcaaa gcaccggtaa tacgttcacc    1320
ctggatgaga tgaagaaagc gtttgagatt tacaacaagg atatgcgtag cgcgaataag    1380
cagtatacgc agtacaacat cccgagcgcg tatgcgttga tgctgaccca aggataccgtt    1440 ccgcgtg tgtattacgg tgatatgtat acggacgacg tcagtacat ggcgcaaaag         1500 agcccatact atgatgcgat cgaaacgctg ctgaaaggtc gcatccgcta tgccgcaggt    1560
ggtcaggaca tgaaggtcaa ctatattggt tacggtaaca ctaacggctg ggatgctgcg    1620
ggcgtgctga ccagcgtacg ttatggcacg ggcgcaaata cgccagcga tacgggtacc    1680 gccgaaacgc gtaatcaagg tatggcagtg attgttagca ccaaccggc gctgcgtctg    1740 actagcaatt tgaccattaa catgggtgcc gcacaccgta atcaggctta ccgtccgctg    1800
```

```
ctgctgacga ccaacgatgg cgtcgcgacc tatttgaacg atagcgatgc gaatggtatc    1860
gttaagtaca ccgacggtaa tggtaatctg accttctccg caaacgagat tcgtggcatc    1920
cgtaacccgc aagttgatgg ctatctggcc gtctgggttc cggtaggtgc gtcggagaat    1980
caggatgttc gtgtggcgcc gagcaaagag aagaacagct ccggtctggt ttacgagagc    2040
aatgctgccc tggatagcca agttatctac gaaggcttca gcaacttcca ggacttcgtt    2100
cagaatccga gccagtatac caacaaaaag attgcagaga atgcaaattt gttcaaatcc    2160
tggggtatta ccagctttga atttgcgccg cagtacgtga gctcggatga tggtagcttc    2220
ctggacagcg ttattcagaa cggttatgcg tttacggacc gctacgacat ggtatgagc    2280 aaagacaaca aatatggttc gctggcggat ttgaaggcag cactgaagag cttgcatgcc    2340
gttggtatta gcgcaatcgc ggattgggtt cctgatcaga tctacaatct gccaggcgac    2400
gaggtcgtca ccgcaacccg cgttaacaac tacggcgaaa ccaaagatgg tgcaatcatt    2460
gatcactctt tgtacgcggc caaaacccgt acttttggta acgactacca gggtaagtat    2520
ggtggtgcgt tcctggacga gctgaaacgt ctgtatccgc agatctttga ccgcgttcag    2580
atttctaccg gtaagcgcat gaccacggac gagaagatca cccaatggtc tgcaaagtat    2640
atgaacggta cgaacatctt ggaccgtggc tctgaatacg ttttgaagaa tggtctgaat    2700
ggttactatg caccaatggt tgcaaaagtt tcgctgccga agttgtggg tagcaatcaa    2760 agcacgaatg gcgacaatca aaacggcgac ggtagcggca gtttgaaaaa gcgtctgttc    2820
agcgtgcgtt accgttataa caatggccag tacgcgaaaa atgcctttat caaagataac    2880
gacggcaatg tttactattt cgacaatagc ggtcgtatgg ctgtcggtga aaaacgatt    2940 gacggcaagc agtacttctt cctggctaat ggcgttcagc tgcgtgacgg ctaccgtcaa    3000
aatcgtcgcg gtcaggtgtt ttactacgac cagaatggtg tgctgaacgc aaacggtaaa    3060
caagacccga agcctgacaa caataacaat gcgagcggcc gtaatcaatt cgtccagatc    3120
ggtaacaacg tgtgggcgta ttatgatggc aatggtaaac gtgtcaccgg tcaccagaac    3180
atcaacggtc aggagttgtt tttcgataac acggtgtcc aggttaaggg tcgtacggtg    3240
aatgagaacg gtgcaattcg ctactatgac gcgaatagcg gtgagatggc acgcaatcgt    3300
ttcgcggaga ttgaaccggg cgtctgggca tactttaaca atgacggcac cgcagtgaag    3360
ggttctcaga atatcaatgg tcaagacctg tacttcgacc agaacggtcg tcaggtcaag    3420
ggtgcgctgg ccaatgttga tgcaacctg cgctattacg acgttaacag cggtgagctg    3480
taccgtaatc gtttccacga aatcgacgg agctggtatt actttgatgg taacggtaat    3540
gcggtgaagg gtatggtcaa tatcaacggc caaaatctgt tgtttgacaa taacggcaaa    3600
cagattaagg gtcatctggt ccgcgtcaac ggcgtcgtgc gctattttga tccgaactct    3660
ggtgaaatgg cggttaatcg ttgggttgag gtgagcccag ttggtgggt ttactttgac    3720 ggtgaaggtc gtggtcagat ctaa                                          3744
```

<210> SEQ ID NO 10
<211> LENGTH: 1247
<212> TYPE: PRT
<213> ORGANISM: Streptococcus salivarius

<400> SEQUENCE: 10

Met Pro Ser His Ile Lys Thr Ile Asn Gly Lys Gln Tyr Tyr Val Glu
1               5                   10                  15

Asp Asp Gly Thr Ile Arg Lys Asn Tyr Val Leu Glu Arg Ile Gly Gly

-continued

```
                20                  25                  30
Ser Gln Tyr Phe Asn Ala Glu Thr Gly Glu Leu Ser Asn Gln Lys Glu
            35                  40                  45
Tyr Arg Phe Asp Lys Asn Gly Thr Gly Ser Ser Ala Asp Ser Thr
    50                  55                  60
Asn Thr Asn Val Thr Val Asn Gly Asp Lys Asn Ala Phe Tyr Gly Thr
65                  70                  75                  80
Thr Asp Lys Asp Ile Glu Leu Val Asp Gly Tyr Phe Thr Ala Asn Thr
                85                  90                  95
Trp Tyr Arg Pro Lys Glu Ile Leu Lys Asp Gly Lys Glu Trp Thr Ala
            100                 105                 110
Ser Thr Glu Asn Asp Lys Arg Pro Leu Leu Thr Val Trp Trp Pro Ser
            115                 120                 125
Lys Ala Ile Gln Ala Ser Tyr Leu Asn Tyr Met Lys Glu Gln Gly Leu
            130                 135                 140
Gly Thr Asn Gln Thr Tyr Thr Ser Phe Ser Ser Gln Thr Gln Met Asp
145                 150                 155                 160
Gln Ala Ala Leu Glu Val Gln Lys Arg Ile Glu Glu Arg Ile Ala Arg
                165                 170                 175
Glu Gly Asn Thr Asp Trp Leu Arg Thr Thr Ile Lys Asn Phe Val Lys
            180                 185                 190
Thr Gln Pro Gly Trp Asn Ser Thr Ser Glu Asn Leu Asp Asn Asn Asp
            195                 200                 205
His Leu Gln Gly Gly Ala Leu Leu Tyr Asn Asn Asp Ser Arg Thr Ser
            210                 215                 220
His Ala Asn Ser Asp Tyr Arg Leu Leu Asn Arg Thr Pro Thr Ser Gln
225                 230                 235                 240
Thr Gly Lys His Asn Pro Lys Tyr Thr Lys Asp Thr Ser Asn Gly Gly
            245                 250                 255
Phe Glu Phe Leu Leu Ala Asn Asp Ile Asp Asn Ser Asn Pro Ala Val
            260                 265                 270
Gln Ala Glu Gln Leu Asn Trp Leu His Tyr Ile Met Asn Ile Gly Thr
            275                 280                 285
Ile Thr Gly Gly Ser Glu Asp Glu Asn Phe Asp Gly Val Arg Val Asp
            290                 295                 300
Ala Val Asp Asn Val Asn Ala Asp Leu Leu Gln Ile Ala Ser Asp Tyr
305                 310                 315                 320
Phe Lys Ala Lys Tyr Gly Ala Asp Gln Ser Gln Asp Gln Ala Ile Lys
            325                 330                 335
His Leu Ser Ile Leu Glu Ala Trp Ser His Asn Asp Ala Tyr Tyr Asn
            340                 345                 350
Glu Asp Thr Lys Gly Ala Gln Leu Pro Met Asp Asp Pro Met His Leu
            355                 360                 365
Ala Leu Val Tyr Ser Leu Leu Arg Pro Ile Gly Asn Arg Ser Gly Val
            370                 375                 380
Glu Pro Leu Ile Ser Asn Ser Leu Asn Asp Arg Ser Glu Ser Gly Lys
385                 390                 395                 400
Asn Ser Lys Arg Met Ala Asn Tyr Ala Phe Val Arg Ala His Asp Ser
            405                 410                 415
Glu Val Gln Ser Ile Ile Gly Gln Ile Ile Lys Asn Glu Ile Asn Pro
            420                 425                 430
Gln Ser Thr Gly Asn Thr Phe Thr Leu Asp Glu Met Lys Lys Ala Phe
            435                 440                 445
```

```
Glu Ile Tyr Asn Lys Asp Met Arg Ser Ala Asn Lys Gln Tyr Thr Gln
    450                 455                 460

Tyr Asn Ile Pro Ser Ala Tyr Ala Leu Met Leu Thr His Lys Asp Thr
465                 470                 475                 480

Val Pro Arg Val Tyr Tyr Gly Asp Met Tyr Thr Asp Asp Gly Gln Tyr
                485                 490                 495

Met Ala Gln Lys Ser Pro Tyr Tyr Asp Ala Ile Glu Thr Leu Leu Lys
                500                 505                 510

Gly Arg Ile Arg Tyr Ala Ala Gly Gly Gln Asp Met Lys Val Asn Tyr
                515                 520                 525

Ile Gly Tyr Gly Asn Thr Asn Gly Trp Asp Ala Ala Gly Val Leu Thr
530                 535                 540

Ser Val Arg Tyr Gly Thr Gly Ala Asn Ser Ala Ser Asp Thr Gly Thr
545                 550                 555                 560

Ala Glu Thr Arg Asn Gln Gly Met Ala Val Ile Val Ser Asn Gln Pro
                565                 570                 575

Ala Leu Arg Leu Thr Ser Asn Leu Thr Ile Asn Met Gly Ala Ala His
                580                 585                 590

Arg Asn Gln Ala Tyr Arg Pro Leu Leu Leu Thr Thr Asn Asp Gly Val
                595                 600                 605

Ala Thr Tyr Leu Asn Asp Ser Asp Ala Asn Gly Ile Val Lys Tyr Thr
                610                 615                 620

Asp Gly Asn Gly Asn Leu Thr Phe Ser Ala Asn Glu Ile Arg Gly Ile
625                 630                 635                 640

Arg Asn Pro Gln Val Asp Gly Tyr Leu Ala Val Trp Val Pro Val Gly
                645                 650                 655

Ala Ser Glu Asn Gln Asp Val Arg Val Ala Pro Ser Lys Glu Lys Asn
                660                 665                 670

Ser Ser Gly Leu Val Tyr Glu Ser Asn Ala Ala Leu Asp Ser Gln Val
                675                 680                 685

Ile Tyr Glu Gly Phe Ser Asn Phe Gln Asp Phe Val Gln Asn Pro Ser
                690                 695                 700

Gln Tyr Thr Asn Lys Lys Ile Ala Glu Asn Ala Asn Leu Phe Lys Ser
705                 710                 715                 720

Trp Gly Ile Thr Ser Phe Glu Phe Ala Pro Gln Tyr Val Ser Ser Asp
                725                 730                 735

Asp Gly Ser Phe Leu Asp Ser Val Ile Gln Asn Gly Tyr Ala Phe Thr
                740                 745                 750

Asp Arg Tyr Asp Ile Gly Met Ser Lys Asp Asn Lys Tyr Gly Ser Leu
                755                 760                 765

Ala Asp Leu Lys Ala Ala Leu Lys Ser Leu His Ala Val Gly Ile Ser
770                 775                 780

Ala Ile Ala Asp Trp Val Pro Asp Gln Ile Tyr Asn Leu Pro Gly Asp
785                 790                 795                 800

Glu Val Val Thr Ala Thr Arg Val Asn Asn Tyr Gly Glu Thr Lys Asp
                805                 810                 815

Gly Ala Ile Ile Asp His Ser Leu Tyr Ala Ala Lys Thr Arg Thr Phe
                820                 825                 830

Gly Asn Asp Tyr Gln Gly Lys Tyr Gly Gly Ala Phe Leu Asp Glu Leu
                835                 840                 845

Lys Arg Leu Tyr Pro Gln Ile Phe Asp Arg Val Gln Ile Ser Thr Gly
850                 855                 860
```

-continued

```
Lys Arg Met Thr Thr Asp Glu Lys Ile Thr Gln Trp Ser Ala Lys Tyr
865                 870                 875                 880

Met Asn Gly Thr Asn Ile Leu Asp Arg Gly Ser Glu Tyr Val Leu Lys
            885                 890                 895

Asn Gly Leu Asn Gly Tyr Tyr Gly Thr Asn Gly Gly Lys Val Ser Leu
        900                 905                 910

Pro Lys Val Val Gly Ser Asn Gln Ser Thr Asn Gly Asp Asn Gln Asn
        915                 920                 925

Gly Asp Gly Ser Gly Lys Phe Glu Lys Arg Leu Phe Ser Val Arg Tyr
    930                 935                 940

Arg Tyr Asn Asn Gly Gln Tyr Ala Lys Asn Ala Phe Ile Lys Asp Asn
945                 950                 955                 960

Asp Gly Asn Val Tyr Tyr Phe Asp Asn Ser Gly Arg Met Ala Val Gly
                965                 970                 975

Glu Lys Thr Ile Asp Gly Lys Gln Tyr Phe Phe Leu Ala Asn Gly Val
            980                 985                 990

Gln Leu Arg Asp Gly Tyr Arg Gln Asn Arg Arg Gly Gln Val Phe Tyr
        995                 1000                1005

Tyr Asp Gln Asn Gly Val Leu Asn Ala Asn Gly Lys Gln Asp Pro
1010                1015                1020

Lys Pro Asp Asn Asn Asn Ala Ser Gly Arg Asn Gln Phe Val
1025                1030                1035

Gln Ile Gly Asn Asn Val Trp Ala Tyr Tyr Asp Gly Asn Gly Lys
1040                1045                1050

Arg Val Thr Gly His Gln Asn Ile Asn Gly Gln Glu Leu Phe Phe
1055                1060                1065

Asp Asn Asn Gly Val Gln Val Lys Gly Arg Thr Val Asn Glu Asn
1070                1075                1080

Gly Ala Ile Arg Tyr Tyr Asp Ala Asn Ser Gly Glu Met Ala Arg
1085                1090                1095

Asn Arg Phe Ala Glu Ile Glu Pro Gly Val Trp Ala Tyr Phe Asn
1100                1105                1110

Asn Asp Gly Thr Ala Val Lys Gly Ser Gln Asn Ile Asn Gly Gln
1115                1120                1125

Asp Leu Tyr Phe Asp Gln Asn Gly Arg Gln Val Lys Gly Ala Leu
1130                1135                1140

Ala Asn Val Asp Gly Asn Leu Arg Tyr Tyr Asp Val Asn Ser Gly
1145                1150                1155

Glu Leu Tyr Arg Asn Arg Phe His Glu Ile Asp Gly Ser Trp Tyr
1160                1165                1170

Tyr Phe Asp Gly Asn Gly Asn Ala Val Lys Gly Met Val Asn Ile
1175                1180                1185

Asn Gly Gln Asn Leu Leu Phe Asp Asn Asn Gly Lys Gln Ile Lys
1190                1195                1200

Gly His Leu Val Arg Val Asn Gly Val Val Arg Tyr Phe Asp Pro
1205                1210                1215

Asn Ser Gly Glu Met Ala Val Asn Arg Trp Val Glu Val Ser Pro
1220                1225                1230

Gly Trp Trp Val Tyr Phe Asp Gly Glu Gly Arg Gly Gln Ile
1235                1240                1245
```